US010925937B1

(12) United States Patent
Gruber et al.

(10) Patent No.: US 10,925,937 B1
(45) Date of Patent: Feb. 23, 2021

(54) VACCINES FOR USE IN TREATING JUVENILE DISORDERS ASSOCIATED WITH INFLAMMATION

(71) Applicant: Siwa Corporation, Chicago, IL (US)

(72) Inventors: Lewis S. Gruber, Chicago, IL (US); Misty S. Gruber, Chicago, IL (US)

(73) Assignee: Siwa Corporation, Chicago, IL (US)

( * ) Notice: Subject to any disclaimer, the term of this patent is extended or adjusted under 35 U.S.C. 154(b) by 0 days.

(21) Appl. No.: 15/863,741

(22) Filed: Jan. 5, 2018

Related U.S. Application Data

(60) Provisional application No. 62/443,442, filed on Jan. 6, 2017.

(51) Int. Cl.
*A61K 47/64* (2017.01)
*A61K 39/00* (2006.01)

(52) U.S. Cl.
CPC ........ *A61K 39/0005* (2013.01); *A61K 47/643* (2017.08); *A61K 47/646* (2017.08)

(58) Field of Classification Search
None
See application file for complete search history.

(56) References Cited

U.S. PATENT DOCUMENTS

| | | |
|---|---|---|
| 4,217,344 A | 8/1980 | Vanlerberghe et al. |
| 4,900,747 A | 2/1990 | Vlassara et al. |
| 4,911,928 A | 3/1990 | Wallach |
| 4,917,951 A | 4/1990 | Wallach |
| 4,965,288 A | 10/1990 | Palfreyman |
| 5,494,791 A | 2/1996 | Cohen |
| 5,518,720 A | 5/1996 | Cohen |
| 5,601,526 A | 2/1997 | Chapelon et al. |
| 5,620,479 A | 4/1997 | Diederich |
| 5,664,570 A | 9/1997 | Bishop |
| 5,693,762 A | 12/1997 | Queen et al. |
| 5,702,704 A | 12/1997 | Bucala |
| 5,766,590 A | 6/1998 | Founds et al. |
| 5,811,075 A | 9/1998 | Vlassara et al. |
| 5,817,771 A | 10/1998 | Bayley et al. |
| 5,984,882 A | 11/1999 | Rosenschein et al. |
| 6,067,859 A | 5/2000 | Kas et al. |
| 6,090,382 A | 7/2000 | Salfeld et al. |
| 6,176,842 B1 | 1/2001 | Tachibana et al. |
| 6,245,318 B1 | 6/2001 | Klibanov et al. |
| 6,309,355 B1 | 10/2001 | Cain et al. |
| 6,380,165 B1 | 4/2002 | Al-Abed et al. |
| 6,387,373 B1 | 5/2002 | Wright et al. |
| 6,410,598 B1 | 6/2002 | Vitek |
| 6,670,136 B2 | 12/2003 | Schmidt et al. |
| 6,676,963 B1 | 1/2004 | Lanza et al. |
| 6,818,215 B2 | 11/2004 | Smith et al. |
| 6,821,274 B2 | 11/2004 | McHale et al. |
| 7,033,574 B1 | 4/2006 | Schneider et al. |
| 7,101,838 B2 | 9/2006 | Stern et al. |
| 7,256,273 B2 | 8/2007 | Basi et al. |
| 7,347,855 B2 | 3/2008 | Eshel et al. |
| 7,358,226 B2 | 4/2008 | Dayton et al. |
| 7,367,988 B1 | 5/2008 | Litovitz |
| 7,470,521 B2 | 12/2008 | O'Keefe |
| 7,751,057 B2 | 7/2010 | Oldenburg et al. |
| 7,815,570 B2 | 10/2010 | Eshel et al. |
| 8,318,164 B2 | 11/2012 | Warne |
| 8,323,651 B2 | 12/2012 | Gu et al. |
| 8,343,420 B2 | 1/2013 | Cioanta et al. |
| 8,398,977 B2 | 3/2013 | Bleck et al. |
| 8,721,571 B2 | 5/2014 | Gruber |
| 9,161,810 B2 | 10/2015 | Gruber |
| 9,320,919 B2 | 4/2016 | Gruber |
| 9,649,376 B2 | 5/2017 | Gruber |
| 9,993,535 B2 | 6/2018 | Gruber |
| 10,226,531 B2 | 3/2019 | Gruber |
| 10,584,180 B2 | 3/2020 | Gruber |
| 10,858,449 B1 | 12/2020 | Gruber |
| 2002/0122799 A1 | 9/2002 | Stern et al. |
| 2002/0193784 A1 | 12/2002 | McHale et al. |
| 2003/0073138 A1 | 4/2003 | Kientsch-Engel et al. |
| 2003/0170173 A1 | 9/2003 | Klaveness et al. |
| 2003/0229283 A1 | 12/2003 | Craig et al. |
| 2004/0039416 A1 | 2/2004 | Myhr |
| 2004/0141922 A1 | 7/2004 | Klaveness et al. |
| 2004/0142391 A1 | 7/2004 | Schmidt |
| 2004/0208826 A1 | 10/2004 | Schneider et al. |

(Continued)

FOREIGN PATENT DOCUMENTS

| | | |
|---|---|---|
| AU | 2009/248945 | 5/2014 |
| AU | 2015318036 | 6/2020 |

(Continued)

OTHER PUBLICATIONS

Mashitah et al., Diabetes Metab Syndr Obes. Aug. 4, 2015;8:347-355 (Year: 2015).*
Zhu et al., Cardiovasc Diabetol. Nov. 13, 2014;13:151 (Year: 2014).*
Haslbeck et al., Acta Neuropathol. Sep. 2005;110(3):247-254 (Year: 2005).*
Sternberg et al., Immunol Invest. 2011;40(2):197-205 Abstract Only (Year: 2011).*
Miyata et al., Biochem Biophys Res Commun 1998; 244: 45-49 (Year: 1998).*
Mulrennan et al., Sci Rep. Mar. 10, 2015;5:8931 (Year: 2015).*
Weber et al, Brain Res. Apr. 27, 1998;791(1-2):11-17 (Year: 1998).*
6, Jun. 14, 2012, U.S. Appl. No. 12/994,421, US.
19, Jul. 21, 2009, PCT/US2009/44951, WO.
6, Dec. 2, 2010, PCT/US2009/44951, WO.

(Continued)

*Primary Examiner* — Daniel C Gamett
(74) *Attorney, Agent, or Firm* — Evan Law Group LLC

(57) ABSTRACT

Various juvenile disorders associated with inflammation may be treated or prevented by immunizing a subject in need thereof against AGE-modified proteins or peptides of a cell. Immunizing a subject includes administering a vaccine that comprises an AGE antigen. Vaccines against AGE-modified proteins or peptides contain an AGE antigen, an adjuvant, optional preservatives and optional excipients.

22 Claims, No Drawings

(56) References Cited

U.S. PATENT DOCUMENTS

| | | |
|---|---|---|
| 2004/0210042 A1 | 10/2004 | Tsuchida |
| 2004/0229830 A1 | 11/2004 | Tachibana et al. |
| 2005/0084538 A1 | 4/2005 | Dayton et al. |
| 2005/0283098 A1 | 12/2005 | Conston et al. |
| 2006/0078501 A1 | 4/2006 | Goertz et al. |
| 2006/0122543 A1 | 6/2006 | Mayer et al. |
| 2006/0188883 A1 | 8/2006 | Murray et al. |
| 2007/0059247 A1 | 3/2007 | Lindner et al. |
| 2007/0065415 A1 | 3/2007 | Kleinsek et al. |
| 2007/0065443 A1 | 3/2007 | Tobia |
| 2007/0078290 A1 | 4/2007 | Esenaliev |
| 2007/0083120 A1 | 4/2007 | Cain et al. |
| 2007/0128117 A1 | 6/2007 | Bettinger et al. |
| 2007/0129633 A1 | 6/2007 | Lee et al. |
| 2007/0225242 A1 | 9/2007 | Erler |
| 2008/0019986 A1 | 1/2008 | Stern et al. |
| 2008/0051680 A1 | 2/2008 | Luebcke |
| 2008/0063603 A1 | 3/2008 | Schneider et al. |
| 2008/0139942 A1 | 6/2008 | Gaud et al. |
| 2008/0160506 A1 | 7/2008 | Liu et al. |
| 2009/0022659 A1 | 1/2009 | Olson et al. |
| 2009/0076390 A1 | 3/2009 | Lee et al. |
| 2009/0306552 A1 | 12/2009 | Furuzono et al. |
| 2010/0028359 A1 | 2/2010 | Gu et al. |
| 2010/0226932 A1 | 9/2010 | Smith et al. |
| 2010/0249038 A1 | 9/2010 | Logsdon |
| 2011/0105961 A1 | 5/2011 | Gruber |
| 2011/0319499 A1 | 12/2011 | Semba et al. |
| 2012/0130287 A1 | 5/2012 | Gruber |
| 2012/0156134 A1 | 6/2012 | Squires |
| 2012/0183534 A1 | 7/2012 | Gruber |
| 2013/0058921 A1 | 3/2013 | Van Rhee |
| 2013/0131006 A1 | 5/2013 | Lee et al. |
| 2013/0243785 A1 | 9/2013 | Gruber |
| 2013/0288980 A1 | 10/2013 | De Keizer et al. |
| 2014/0234339 A1 | 8/2014 | Ohlsen |
| 2014/0234343 A1 | 8/2014 | Lee et al. |
| 2014/0303526 A1 | 10/2014 | Gruber |
| 2015/0376279 A1 | 12/2015 | Hansen |
| 2016/0101299 A1 | 4/2016 | Gruber |
| 2016/0152697 A1 | 6/2016 | Gruber |
| 2016/0175413 A1 | 6/2016 | Gruber |
| 2016/0193358 A1 | 7/2016 | Algate |
| 2016/0215043 A1 | 7/2016 | Gruber |
| 2016/0339019 A1 | 11/2016 | Laberge et al. |
| 2016/0340418 A1 | 11/2016 | Baron |
| 2017/0216435 A1 | 8/2017 | Gruber |
| 2017/0240632 A1 | 8/2017 | Thomas |
| 2017/0247472 A1 | 8/2017 | Gruber |
| 2018/0044411 A1 | 2/2018 | Gruber |
| 2018/0111982 A2 | 4/2018 | Gruber |
| 2018/0298087 A1 | 10/2018 | Gruber |
| 2018/0312577 A1 | 11/2018 | Gruber |
| 2018/0326026 A1 | 11/2018 | Gruber |
| 2019/0031781 A1 | 1/2019 | Gruber |
| 2019/0119371 A1 | 4/2019 | Gruber |
| 2019/0328873 A1 | 10/2019 | Gruber |
| 2019/0328876 A1 | 10/2019 | Gruber |
| 2020/0055957 A1 | 2/2020 | Gruber |
| 2020/0150131 A1 | 5/2020 | Gruber |
| 2020/0231706 A1 | 7/2020 | Gruber |

FOREIGN PATENT DOCUMENTS

| | | |
|---|---|---|
| CN | 201580056616.3 | 4/2020 |
| DE | 102008009461 | 8/2009 |
| EP | 0 259 893 | 3/1988 |
| EP | 1 219 639 | 7/2002 |
| EP | 1 415 997 | 5/2004 |
| EP | 1 867 659 | 12/2007 |
| EP | 2 294 178 | 7/2014 |
| EP | 15772116.8 | 3/2020 |
| EP | 19210193.9 | 5/2020 |
| IL | 251210 | 6/2020 |
| IL | 258397 | 6/2020 |
| JP | 09178740 | 7/1997 |
| JP | 11246599 | 9/1999 |
| JP | 2003/160599 | 6/2003 |
| JP | 2006-249015 | 9/2006 |
| JP | 2007-163407 | 6/2007 |
| JP | 2017-515740 | 1/2020 |
| JP | 2018-543120 | 3/2020 |
| JP | 2018-519727 | 5/2020 |
| JP | 2018-543120 | 5/2020 |
| JP | 2019-230026 | 12/2020 |
| RU | 2 270 029 | 1/2006 |
| RU | 2018110885 | 1/2020 |
| RU | 2017113349 | 3/2020 |
| RU | 2018132998 | 5/2020 |
| WO | 1993/13421 | 7/1993 |
| WO | 1995/20979 | 8/1995 |
| WO | 1996/20958 | 7/1996 |
| WO | 1997/07803 | 3/1997 |
| WO | 1997/49429 | 12/1997 |
| WO | 1999/07893 | 2/1999 |
| WO | 1999/14587 | 3/1999 |
| WO | 1999/64463 | 12/1999 |
| WO | 2000/20458 | 4/2000 |
| WO | 2001/00245 | 1/2001 |
| WO | 2004/011460 | 2/2004 |
| WO | 2004/016229 | 2/2004 |
| WO | 2004/076677 | 9/2004 |
| WO | 2006/012415 | 2/2006 |
| WO | 2006/017647 | 2/2006 |
| WO | 2006/040597 | 4/2006 |
| WO | 2009/136382 | 11/2009 |
| WO | 2009/143411 | 11/2009 |
| WO | 2010/005531 | 1/2010 |
| WO | 2012/047629 | 4/2012 |
| WO | 2012/071269 | 5/2012 |
| WO | 2012/135616 | 10/2012 |
| WO | WO-2012135616 A1 * | 10/2012 ......... A61K 39/0005 |
| WO | 2013/009785 | 1/2013 |
| WO | 2013/043161 | 3/2013 |
| WO | 2013/070468 | 5/2013 |
| WO | 2014/136114 | 9/2014 |
| WO | 2015/112835 | 7/2015 |
| WO | 2015/116740 | 8/2015 |
| WO | 2016/044252 | 3/2016 |
| WO | 2017/065837 | 4/2017 |
| WO | 2017/143073 | 8/2017 |
| WO | 2017/181116 | 10/2017 |
| WO | 2017/222535 | 12/2017 |
| WO | 2018/191718 | 10/2018 |
| WO | 2018/204679 | 11/2018 |
| WO | 2020/023532 | 1/2020 |
| WO | 2020/041625 | 2/2020 |

OTHER PUBLICATIONS

13, Apr. 26, 2012, PCT/US2011/053399, WO.
3, Jul. 2, 2012, U.S. Appl. No. 12/951,768, US.
21, Mar. 30, 2012, U.S. Appl. No. 12/951,768, US.
12, Jun. 13, 2012, PCT/US2011/061387, WO.
13, Jun. 27, 2012, PCT/US12/31446, WO.
5, May 14, 2012, 200980118817.6, CN.
9, Nov. 8, 2011, 09 751 639.7, EP.
6, Jun. 12, 2012, 09 751 639.7, EP.
3, Jul. 20, 2012, U.S. Appl. No. 12/994,421, US.
4, Jul. 13, 2012, 10-2012-7026063, KR.
27, Sep. 10, 2012, U.S. Appl. No. 12/994,421, US.
9, Nov. 5, 2012, U.S. Appl. No. 12/951,768, US.
4, Nov. 8, 2012, 2009248945, AU.
4, Aug. 20, 2012, 209513, IL.
6, Jan. 3, 2013, 09 751 639.7, EP.
10, Feb. 26, 2013, U.S. Appl. No. 12/994,421, US.
5, Dec. 25, 2012, 2010152693, RU.
3, Mar. 21, 2013, U.S. Appl. No. 12/951,768, US.
5, Feb. 28, 2013, 200980118817.6, CN.
10, Feb. 28, 2013, 10-2010-7026063, KR.
3, Mar. 27, 2013, U.S. Appl. No. 12/951,768, US.
3, Apr. 15, 2013, 2009248945, AU.

(56) References Cited

OTHER PUBLICATIONS

3, May 21, 2013, U.S. Appl. No. 12/994,421, US.
9, Apr. 23, 2013, 2010152693, RU.
7, May 30, 2013, PCT/US2011/061387, WO.
3, May 22, 2013, 209513, IL.
3, Jul. 18, 2013, U.S. Appl. No. 12/994,421, US.
5, Jul. 26, 2013, 09751639.7, EP.
7, Apr. 2, 2013, 11776932.3, WO.
4, Jul. 16, 2013, 2010/012473, MX.
14, Jul. 29, 2013, U.S. Appl. No. 12/951,768, US.
5, Sep. 30, 2013, 10-2010-7026063, KR.
3, Nov. 15, 2013, U.S. Appl. No. 12/951,768, US.
6, Oct. 10, 2013, PCT/US2012/031446, WO.
8, Nov. 19, 2013, 2011-511734, JP.
8, Oct. 10, 2013, 200980118817.6, CN.
15, Dec. 20, 2013, U.S. Appl. No. 12/951,768, US.
7, Dec. 23, 2013, 10-2010-7026063, KR.
6, Jan. 23, 2014, 09751639.7, EP.
3, Feb. 4, 2014, 2009248945, AU.
11, Mar. 18, 2014, 2010/012473, MX.
5, May 7, 2014, 200980118817.6, CN.
3, May 25, 2014, 209513, IL.
7, May 26, 2014, 2010152693, RU.
3, Jun. 17, 2014, 2010/012473, MX.
3, Jun. 20, 2014, 2,724,886, CA.
8, Jun. 22, 2014, 10-2013-7028228, KR.
3, Jul. 29, 2014, 10-2010-7026063, KR.
9, Jul. 29, 2014, 10-2012-7026483, KR.
6, Sep. 3, 2014, U.S. Appl. No. 13/332,976, US.
30, Sep. 9, 2014, U.S. Appl. No. 14/247,081, US.
6, Sep. 12, 2014, U.S. Appl. No. 14170802.4, EP.
7, Oct. 8, 2014, 200980118817.6, CN.
51, Nov. 18, 2014, U.S. Appl. No. 13/332,976, US.
34, Nov. 18, 2014, U.S. Appl. No. 12/994,421, US.
3, Dec. 2, 2014, 209513, IL.
8, Dec. 3, 2014, 2011-511734, JP.
3, Jan. 13, 2015, U.S. Appl. No. 14/247,081, US.
5, Feb. 2, 2015, U.S. Appl. No. 14/247,081, US.
10, Dec. 16, 2014, 2010152693, RU.
3, Feb. 5, 2015, 2,724,886, CA.
6, Feb. 27, 2015, 10-2012-7026483, KR.
5, Mar. 13, 2015, U.S. Appl. No. 12/994,421, US.
6, Mar. 13, 2015, U.S. Appl. No. 13/332,976, US.
44, Mar. 27, 2015, U.S. Appl. No. 12/994,421, US.
25, Apr. 1, 2015, U.S. Appl. No. 13/332,976, US.
4, Mar. 26, 2015, 200980118817.6, CN.
3, Apr. 23, 2015, U.S. Appl. No. 13/332,976, US.
3, May 1, 2015, U.S. Appl. No. 13/332,976, US.
4, Apr. 27, 2015, 10-2013-7028228, KR.
29, May 6, 2015, U.S. Appl. No. 14/247,081, US.
7, Apr. 20, 2015, 10-2015-7007520, KR.
18, Jun. 11, 2015, U.S. Appl. No. 13/332,976, US.
3, Jul. 10, 2015, U.S. Appl. No. 14/247,081, US.
11, Jul. 21, 2015, U.S. Appl. No. 14/278,081, US.
8, Jun. 22, 2015, 2015-076575, JP.
3, Jun. 5, 2015, 2011332143, AU.
3, Jun. 22, 2015, 2014202548, AU.
5, Jul. 17, 2015, 14170802.4, EP.
54, Sep. 10, 2015, U.S. Appl. No. 13/876,157, US.
4, Sep. 2, 2015, U.S. Appl. No. 12/994,421, US.
5, Sep. 8, 2015, 2,724,886, CA.
7, Jul. 27, 2015, MX/a/2013/013310, MX.
4, Nov. 27, 2015, 10-2015-7007520, KR.
5, Dec. 10, 2015, 14170802.4, EP.
3, Jan. 8, 2016, 2014202548, AU.
2, Jan. 11, 2016, 2011332143, AU.
7, Jan. 12, 2016, 2015-076575, JP.
35, Jan. 19, 2016, U.S. Appl. No. 12/994,421, US.
2, Jan. 25, 2016, 2011332143, AU.
8, Mar. 30, 2016, U.S. Appl. No. 13/876,157, US.
17, Mar. 31, 2016, PCT/US2015/050154, WO.
7, Apr. 6, 2016, MX/a/2013/013310, MX.
5, Apr. 14, 2016, 2,724,886, CA.
8, Apr. 28, 2016, 2014202548, AU.
5, Jun. 20, 2016, 2014202548, AU.
13, Jun. 15, 2016, 201510303227.8, CN.
4, Aug. 24, 2016, 2016204196, AU.
4, Apr. 14, 2016, 240242, IL.
8, Jul. 19, 2016, 2016-098558, JP.
9, Jul. 13, 2016, 2015114990, RU.
15, Oct. 17, 2016, U.S. Appl. No. 13/876,157, US.
5, Oct. 26, 2016, 2,818,647, CA.
6, Sep. 22, 2016, U.S. Appl. No. 14/974,095, US.
16, Dec. 30, 2016, 201510303227.8, CN.
8, Dec. 29, 2016, 4875/KOLNP/2010, IN.
9, Jan. 5, 2017, U.S. Appl. No. 13/876,157, US.
16, Dec. 2, 2016, PCT/US2016/039076, WO.
16, Aug. 10, 2016, PCT/US2016/034880, WO.
8, Feb. 21, 2017, 16198527.0, EP.
6, Mar. 23, 2017, 11776932.3, EP.
4, Feb. 20, 2017, 2,724,886, CA.
1, May 1, 2017, 2,724,886, CA.
4, Jan. 23, 2017, 240242, IL.
9, Dec. 19, 2016, 2016-098558, JP.
9, Feb. 15, 2017, MX/a/2013/013310, MX.
6, Jan. 27, 2017, 2015114990, RU.
4, Apr. 19, 2017, 2,818,647, CA.
45, Feb. 13, 2017, U.S. Appl. No. 14/974,095, US.
20, May 17, 2017, PCT/US2017/018185, WO.
8, Jun. 13, 2017, U.S. Appl. No. 14/974,561, US.
10, Mar. 30, 2017, PCT/US2015/050154, WO.
5, Jun. 27, 2017, U.S. Appl. No. 14/974,095, US.
2, Nov. 24, 2016, 14170802.4, EP.
3, May 10, 2017, 2017113349, RU.
14, May 15, 2017, 201510303227.8, CN.
5, May 29, 2017, 248652, IL.
4, Aug. 8, 2017, 2015114990, RU.
12, Aug. 23, 2017, 11776932.3, EP.
25, Sep. 22, 2017, U.S. Appl. No. 14/974,095, US.
16, Sep. 29, 2017, PCT/US2017/027773, WO.
4, Oct. 13, 2017, 2,818,647, CA.
14, Oct. 18, 2017, 2015114990, RU.
67, Nov. 15, 2017, U.S. Appl. No. 14/974,561, US.
4, Nov. 29, 2017, 2,818,647, CA.
7, Nov. 30, 2017, U.S. Appl. No. 14/932,200, US.
3, Jan. 11, 2018, U.S. Appl. No. 14/974,095, US.
19, Jan. 30, 2018, U.S. Appl. No. 14/974,095, US.
5, Feb. 8, 2018, U.S. Appl. No. 14/974,561, US.
81, Feb. 21, 2018, U.S. Appl. No. 14/932,200, US.
17, Mar. 16, 2018, 11776932.3, EP.
7, Apr. 30, 2018, 2017-086871, JP.
4, May 11, 2018, U.S. Appl. No. 14/974,095, US.
7, May 14, 2018, U.S. Appl. No. 14/920,737, US.
27, May 21, 2018, U.S. Appl. No. 15/511,731, US.
51, May 21, 2018, U.S. Appl. No. 15/489,624, US.
12, May 29, 2018, U.S. Appl. No. 14/974,561, US.
1, Jun. 22, 2018, 2,818,647, CA.
1, Jul. 20, 2018, 2,818,647, CA.
11, Aug. 30, 2018, PCT/US2017/018185, WO.
40, Sep. 5, 2018, U.S. Appl. No. 14/932,200, US.
51, Sep. 12, 2018, U.S. Appl. No. 14/920,737, US.
7, Sep. 14, 2018, 15772116.8, EP.
21, Sep. 25, 2018, U.S. Appl. No. 14/974,561, US.
13, Oct. 23, 2018, U.S. Appl. No. 15/489,624, US.
8, Oct. 25, 2018, PCT/US2017/027773, WO.
18, Nov. 15, 2018, U.S. Appl. No. 15/511,731, US.
6, Nov. 28, 2018, U.S. Appl. No. 15/720,912, US.
9, Dec. 6, 2018, 2017113349, RU.
10, Dec. 13, 2018, U.S. Appl. No. 14/932,200, US.
2, Jan. 11, 2019, 17708098.3, EP.
6, Jan. 23, 2019, U.S. Appl. No. 15/489,624, US.
5, Feb. 4, 2019, U.S. Appl. No. 15/863,811, US.
5, Feb. 6, 2019, U.S. Appl. No. 14/974,561, US.

(56) References Cited

OTHER PUBLICATIONS

5, Feb. 11, 2019, U.S. Appl. No. 15/863,784, US.
3, Feb. 14, 2019, U.S. Appl. No. 15/511,731, US.
12, Mar. 4, 2019, U.S. Appl. No. 14/920,737, US.
20, Mar. 12, 2019, U.S. Appl. No. 14/974,561, US.
55, Mar. 26, 2019, U.S. Appl. No. 15/720,912, US.
144, Feb. 25, 2019, 17708098.3, EP.
9, Dec. 25, 2018, PCT/US2016/039076, WO.
5, Mar. 20, 2019, U.S. Appl. No. 15/863,828, US.
5, Mar. 31, 2019, 2017086871, JP.
14, Apr. 8, 2019, 2017113349, RU.
3, Jun. 7, 2019, U.S. Appl. No. 14/932,200, US.
9, Jul. 1, 2019, 2017-515740, JP.
24, Aug. 15, 2019, U.S. Appl. No. 14/920,737, US.
15, Jun. 19, 2019, 18184822.7, EP.
15, Jun. 27, 2019, U.S. Appl. No. 15/511,731, US.
144, Jul. 19, 2019, 17708098.3, EP.
14, Sep. 25, 2019, U.S. Appl. No. 15/863,811, US.
3, Apr. 14, 2016, 14170802.4, EP.
3, Sep. 8, 2017, 11776932.3, EP.
3, Jan. 19, 2018, 11776932.3, EP.
3, Feb. 7, 2018, 11776932.3, EP.
3, Jan. 30, 2019, 15772116.8, EP.
4, Aug. 30, 2019, 17737078.0, EP.
U.S. Appl. No. 10/358,502, filed Jul. 2019, Gruber.
International Search Report dated Jul. 21, 2009 for PCT application No. PCT/US2009/44951.
Lindsey, J.B. et al., "Receptor for advanced glycation end-products (RAGE) and soluble RAGE (sRAGE): Cardiovascular implications", Diabetes Vascular Disease Research, vol. 6, No. 1, pp. 7-14, (2009).
Ando, K. et al., "Membrane proteins of human erythrocytes are modified by advanced glycation end products during aging in the circulation", Biochemical and Biophysical Research Communications, vol. 258, pp. 123-127, (1999).
Jandeleit-Dahm, K. et al., "The AGE/RAGE axis in diabetes-accelerated atherosclerosis", Clinical and Experimental Pharmacology and Physiology, vol. 35, pp. 329-334, (2008).
Sakata, N. et al., "Immunohistochemical localization of different epitopes of advanced glycation end products in human atherosclerotic lesions", Atherosclerosis, vol. 141, pp. 61-75, (1998).
Karachalias, N. et al., "Accumulation of fructosyl-lysine and advanced glycation end products in the kidney, retina and peripheral nerve of streptozotocin-induced diabetic rats", Biochemical Society Transactions, vol. 31, pp. 1423-1425, (2003).
Aroian, R. et al., "Pore-forming toxins and cellular non-immune defenses (CNIDs)", Current Opinion in Microbiology, vol. 10, pp. 57-61, (2007).
Dobson, J., "A twist on tumour targeting", Nature Materials, vol. 9, pp. 95-96, (2010).
Gutensohn, K. et al., "Extracorporeal plateletpheresis induces the interaction of activated platelets with white blood cells", Vox Sanguinis, vol. 78, No. 2, pp. 101-105, (2000).
Horiuchi, S. et al., "Immunochemical approach to characterize advanced glycation end products of the maillard reaction", The Journal of Biological Chemistry, vol. 266, No. 12, pp. 7329-7332, (1991).
Soetanto, K. et al., "Fundamental examination of cattle red blood cells damage with ultrasound exposure microscopic system (UEMS)", Japanese Journal of Applied Physics, vol. 37, part 1, No. 5B, pp. 3070-3073, (1998).
Harja, E. et al., "Vascular and inflammatory stresses mediate atherosclerosis via RAGE and its ligands in apoE-/-mice", The Journal of Clinical Investigation, vol. 118, No. 1, pp. 183-194, (2008).
Carstensen, E.L. et al., "Lysis of erythrocytes by exposure to cw ultrasound", Ultrasound in Medicine and Biology, vol. 19, No. 2, pp. 147-165, (1993).

Miller, M.W. et al., "Comparative sensitivity of human erythrocytes and lymphocytes to sonolysis by 1-MHz ultrasound", Ultrasound in Medicine and Biology, vol. 23, No. 4, pp. 635-638, (1997).
Iwata, H. et al., "Effect of carbonyl compounds on red blood cells deformability", Biochemical and Biophysical Research Communications vol. 321, pp. 700-706, (2004).
Schmitt, A. et al., "The binding of advanced glycation end products to cell surfaces can be measured using bead-reconstituted cellular membrane proteins", Biochimica et Biophysica Acta, vol. 1768, pp. 1389-1399, (2007).
Self-Medlin, Y. et al., "Glucose promotes membrane cholesterol crystalline domain formation by lipid peroxidation", Biochimica et Biophysica Acta, vol. 1788, pp. 1398-1403, (2009).
Singh, N. et al., "The PPAR-γ activator, rosiglitazone, inhibits actin polymerisation in monocytes: involvement of Akt and intracellular calcium", Biochemical and Biophysical Research Communications, vol. 333, pp. 455-462, (2005).
Li, Y-M. et al., "Effects of high glucose on mesenchymal stem cell proliferation and differentiation", Biochemical and Biophysical Research Communications, vol. 363, pp. 209-215, (2007).
Takata, K. et al., "Endocytic uptake of nonenzymatically glycosylated proteins is mediated by a scavenger receptor for aldehyde-modified proteins", The Journal of Biological Chemistry, vol. 263, No. 29, pp. 14819-14825, (1988).
Mi, Y. et al., "Apoptosis in leukemia cells is accompanied by alterations in the levels and localization of nucleolin", Journal of Biological Chemistry, vol. 278, pp. 8572-8579, (2003).
Christian, S. et al., "Nucleolin expressed at the cell surface is a marker of endothelial cells in angiogenic blood vessels", Journal of Cell Biology, vol. 163, No. 4, pp. 871-878, (2003).
Loo, T.W. et al., "Identification of residues in the drug translocation pathway of the human multidrug resistance P-glycoprotein by arginine mutagenesis", Journal of Biological Chemistry, vol. 284, No. 36, pp. 24074-24087, (2009).
Brundin, P. et al., "Prion-like transmission of protein aggregates in neurodegenerative diseases", Nature Reviews Molecular Cell Biology, vol. 11, No. 4, pp. 301-307, (2010).
Perez, C. et al., "Translational control of the abundance of cytoplasmic poly(A) binding protein in human cytomegalovirus-infected cells", Journal of Virology, vol. 85, No. 1, pp. 156-164, (2011).
Persson, J. et al., "Interleukin-lbeta and tumour necrosis factor-alpha impede neutral lipid turnover in macrophage-derived foam cells", BMC Immunology, vol. 9, No. 70, pp. 1-11, (2008).
Vergne, I. et al., "Cell biology of mycobacterium tuberculosis phagosome", Annu. Rev. Cell Dev. Biology, vol. 20, pp. 367-394, (2004).
Moskowitz, S.M. et al., "The role of *pseudomonas* lipopolysaccharide in cystic fibrosis airway Infection", Subcell Biochemistry, vol. 53, pp. 241-253, (2010).
Hall-Stoodley, L. et al., "Direct detection of bacterial biofilms on the middle-ear mucosa of children with chronic otitis media", JAMA, vol. 296, No. 2, pp. 202-211, (2006).
Franke-Fayard, B. et al., "Sequestration and tissue accumulation of human malaria parasites: Can we learn anything from rodent models of malaria?", PLoS Pathogens, vol. 6, issue 9, pp. 1-10, e1001032, (2010).
Zhang, S. et al., "Delineation of diverse macrophage activation programs in response to intracellular parasites and cytokines", PLoS Neglected Tropical Diseases, vol. 4, No. 3, e648 (2010).
Ma, Y. et al., "NS3 helicase domains involved in infectious intracellular hepatitis C virus particle assembly", Journal of Virology, vol. 82, No. 15, pp. 7624-7639, (2008).
Korant, B.D. et al., "Inhibition by zinc of rhinovirus protein cleavage: interaction of zinc with capsid polypeptides", Journal of Virology, vol. 18, No. 1, pp. 298-306, (1976).
Ameli, S. et al., "Effect of immunization with homologous LDL and oxidized LDL on early atherosclerosis in hypercholesterolemic rabbits", Arteriosclerosis, Thrombosis, and Vascular Biology, vol. 16, pp. 1074-1079, (1996).
Nilsson, J. et al., "Inflammation and immunity in diabetic vascular complications", Current Opinion in Lipidology, vol. 19, issue 5, pp. 519-524, (2008).

(56) References Cited

OTHER PUBLICATIONS

Schiopu, A. et al., "Recombinant antibodies to an oxidized low-density lipoprotein epitope induce rapid regression of atherosclerosis in apobec-1$^{-/-}$/low-density lipoprotein receptor$^{-/-}$mice", Journal of the American College of Cardiology, vol. 50, No. 24, pp. 2313-2318, (2007).
Schiopu, A. et al., "Recombinant human antibodies against aldehyde-modified apolipoprotein B-100 peptide sequences inhibit atherosclerosis", Circulation, vol. 110, pp. 2047-2052, (2004).
Bassirat, M. et al., "Short- and long-term modulation of microvascular responses in streptozotocin-induced diabetic rats by glycosylated products", Journal of Diabetes and its Complications, vol. 24, pp. 64-72, (2010).
Ge, J. et al., "Advanced glycosylation end products might promote atherosclerosis through inducing the immune maturation of dendritic cells", Arteriosclerosis, Thrombosis, and Vascular Biology, vol. 25, pp. 2157-2163, (2005).
Gugliucci, A. et al., "Circulating advanced glycation peptides in streptozotocin-induced diabetic rats: evidence for preferential modification of IgG light chains", Life Sciences, vol. 62, No. 23, pp. 2141-2150, (1998).
Pullerits, R. et al., "Synovial fluid expression of autoantibodies specific for RAGE relates to less erosive course of rheumatoid arthritis", Rheumatology, vol. 46, pp. 1367-1371, (2007).
Bro, S. et al., "A neutralizing antibody against receptor for advanced glycation end products (RAGE) reduces atherosclerosis in uremic mice", Atherosclerosis, vol. 201, pp. 274-280, (2008).
Turk, Z. et al., "Detection of autoantibodies against advanced glycation end products and AGE-immune complexes in serum of patients with diabetes mellitus", Clinica Chimica Acta, vol. 303, pp. 105-115, (2001).
Li, M. et al., "Glycan changes: cancer metastasis and anti-cancer vaccines", Journal of Biosciences, vol. 35, No. 4, pp. 665-673, (2010).
Kyte, J.A. et al., "Third international conference on cancer vaccines/adjuvants/delivery for the next decade (CVADD 2009)", Expert Reviews Vaccines, vol. 9, No. 2, pp. 119-123, (2010).
Akbulut, H. et al., "Chemotherapy targeted to cancer tissue potentiates antigen-specific immune response induced by vaccine for in vivo antigen loading and activation of dendritic cells", Molecular Therapy, vol. 16, No. 10, pp. 1753-1760, (2008).
Li, Y.M. et al., "Glycation products in aged thioglycollate medium enhance the elicitation of peritoneal macrophages", Jounal of Immunological Methods, vol. 201, issue 2, pp. 183-188, (1997).
Poggioli, S. et al., "Age-related increase of protein glycation in peripheral blood lymphocytes is restricted to preferential target proteins", Experimental Gerontology, vol. 37, issue 10-11, pp. 1207-1215, (2002).
Poggioli, S. et al., "Evidence of preferential protein targets for age-related modifications in peripheral blood lymphocytes", Annals of the New York Academy of Sciences, vol. 1019, issue 1, pp. 211-214, (2004).
Dominaitiene, R. et al., "Effects of differently oxidized LDL on the expression of pro-inflammatory molecules in human monocytes in vitro", in Vitro and Molecular Toxicology, vol. 14, No. 2, pp. 83-97, (2001).
Jiang, Z-H. et al., "Synthetic vaccines: the role of adjuvants in immune targeting", Current Medicinal Chemistry, vol. 10, No. 15, pp. 1423-1439, (2003).
Buskas, T. et al., "Immunotherapy for cancer: Synthetic carbohydrate-based vaccines", Chemical Communications, Issue 36, pp. 5335-5349, (2009).
Cohen, M.P. et al., "Amelioration of diabetic nephropathy by treatment with monoclonal antibodies against glycated albumin", Kidney International, vol. 45, pp. 1673-1679, (1994).
Davis, P.J. et al., "How can thermal processing modify the antigenicity of proteins?", Allergy, vol. 56, supplemental 67, pp. 56-60, (2001).
Koga, M. et al. "Clinical impact of glycated albumin as another glycemic control marker", Endocrine Journal, vol. 57, No. 9, pp. 751-762, (2010).
Shcheglova, T. et al., "Reactive immunization suppresses advanced glycation and mitigates diabetic nephropathy", Journal of the American Society of Nephrology, vol. 20, No. 5, pp. 1012-1019, (2009).
Virella, G. et al., "Autoimmune response to advanced glycosylation end-products of human LDL", Journal of Lipid Research, vol. 44, pp. 487-493, (2003).
Ihssen, J. et al., "Production of glycoprotein vaccines in *Escherichia coli*", Microbial Cell Factories, vol. 9, No. 61, pp. 1-13, (2010).
Habets, K.L.L. et al., "Vaccination using oxidized low-density lipoprotein-pulsed dendritic cells reduces atherosclerosis in LDL receptor-deficient mice", Cardiovascular Research, vol. 85, pp. 622-630, (2010).
Mironova, R. et al., "Glycation and post-translational processing of human interferon-γ expressed in *Escherichia coli*", the Journal of Biological Chemistry, vol. 278, No. 51, pp. 51068-51074, (2003).
Vogel, F.R. et al., "A compendium of vaccine adjuvants and excipients", Pharmaceutical Biotechnology, vol. 6, pp. 141-228, (1995).
Monograph series, World Health Organization, "Methods of Vaccine Production", part 4, chapters 18-29, pp. 189-267, (1973).
Cohen, M.P. et al., "Prevention of diabetic nephropathy in db/db mice with glycated albumin antagonists: A novel treatment strategy", the Journal of Clinical Investigation, vol. 95, pp. 2338-2345, (1995).
Naka, Y. et al., "RAGE Axis, Animal models and novel insights into the vascular complications of diabetes", Arteriosclerosis, Thrombosis, and Vascular Biology, vol. 24, pp. 1342-1349, (2004).
European Search Report dated Nov. 8, 2011 for PCT application No. PCT/US2009/044951.
Bierhaus, A. et al., "AGEs and their interaction with AGE-receptors in vascular disease and diabetes mellitus. I. the AGE concept", Cardiovascular Research, vol. 37, No. 3, pp. 586-600, (1998).
Murphy, J.F. "Trends in cancer immunotherapy", Clinical Medicine Insights: Oncology, vol. 4, pp. 67-80, (2010).
Beier, K.C. "Master switches of T-cell activation and differentiation", European Respiratory Journal, vol. 29, pp. 804-812, (2007).
Schmidlin, H., "New insights in the regulation of human B cell differentiation", Trends in Immunology, vol. 30, No. 6, pp. 277-285, (2009).
Coler, R.N. et al., "Development and characterization of synthetic glucopyranosyl lipid adjuvant system as a vaccine adjuvant", PLoS One, vol. 6, No. 1, e16333, pp. 1-12, (2011).
Cheadle, E.J., "Bugs as drugs for cancer", Immunology, vol. 107, pp. 10-19, (2002).
The Pink Book, Epidemiology and Prevention of vaccine preventable diseases, 11th Ed., pp. B7-B13, (2009), Found at www.cdc.gov/vaccines/pubs/pinkbook/downloads/appendices/b/excipient-table-1.pdf.
The Pink Book, Epidemiology and Prevention of vaccine preventable diseases, 11$^{th}$ Ed., 4 pages, (2009), Found at www.cdc.gov/vaccines/pubs/pinkbook/downloads/appendices/b/excipient-table-2.pdf.
Book Reviews, International Microbiology, vol. 7, pp. 291-295, (2004).
"Glycation: How eating sugar causes wrinkles", www.brighthub.com/health/diet-nutrition/articles/18410.aspx, 1 page, published Oct. 8, 2009.
Ellis, G., "The myth of the glycemic index and its child: good carbs-bad carbs", Targeted Body Systems, www.targetedbodysystems.com/tag/low-carb-diet-plans/, pp. 1-5, published Feb. 16, 2009.
"Diabetic glycation and inflammation—what diabetes does to your coronary arteries", www.rebelheartsurgeon-antioxidants.net/diabetic-glycation.html, pp. 1-9, downloaded Aug. 17, 2010.
Dziarski, R., "Cell-bound albumin is the 70-kDa peptidoglycan-, lipopolysaccharide-, and lipoteichoic acid-binding protein on lymphocytes and macrophages", the Journal of Biological Chemistry, vol. 269, No. 32, pp. 20431-20436, (1994).
Peters Jr. T.,"5-Metabolism: Albumin in the body", All About Albumin Biochemistry, Genetics, and Medical Applications, Chapter 5, pp. 188-250, (1995).

(56) References Cited

OTHER PUBLICATIONS

Vlassara, H. et al., "High-affinity-receptor-mediated uptake and degradation of glucose-modified proteins: A potential mechanism for the removal of senescent macromolecules", Proceeding of the National Academy of Science, USA, Biochemistry, vol. 82, pp. 5588-5592, (1985).
Wade, N., "Purging cells in mice is found to combat aging ills", New York Times, found at NYTimes.com, pp. 1-3, (2011).
Roll, P. et al., "Anti-CD20 therapy in patients with rheumatoid arthritis", Arthritis & Rheumatism, vol. 58, No. 6, pp. 1566-1575, (2008).
Kajstura J. et al., "Myocyte turnover in the aging human heart", Circulation Research, vol. 107, pp. 1374-1386, (2010).
Baker, D.J. et al., "Clearance of p16lnk4a-positive senescent cells delays ageing-associated disorders", Nature, vol. 479, pp. 232-236, (2011).
Breyer, V. et al., "Intracellular glycation of nuclear DNA, mitochondrial DNA, and cytosolic proteins during senescence-like growth arrest", DNA Cell Biology, vol. 30, No. 9, pp. 681-689, (2011).
Ravelojaona, V. et al., "Expression of senescence-associated beta-galactosidase (SA-beta-Gal) by human skin fibroblasts, effect of advanced glycation end-products and fucose or rhamnose-rich polysaccharides", Archives of Gerontology and Geriatrics, vol. 48, issue 2, pp. 151-154, (2009).
International Search Report dated Apr. 26, 2012 for PCT application No. PCT/US2011/053399.
International Search Report dated Jun. 13, 2012 for PCT application No. PCT/US2011/061387.
Wautier, J.-L. et al., "Advanced glycation end products (AGES) on the surface of diabetic erythrocytes bind to the vessel wall via a specific receptor inducing oxidant stress in the vasculature: A link between surface-associated AGEs and diabetic complications", Proc. Natl. Acad. Sci. USA, vol. 91, No. 16, pp. 7742-7746, (1994).
Siegel, R. J. et al., "Ultrasonic plaque ablation: A new method for recanalization of partially or totally occluded arteries", Circulation, vol. 78, No. 6, pp. 1443-1448, (1988).
International Search Report dated Jun. 27, 2012 for PCT application No. PCT/US2012/031446.
Immuno, Catalog No. 637061, 637062, "Mouse, anti-age (advanced glycation end products), monoclonal antibody", http://www.mpbio.com/detailed_info.php?family_key=0863706, 2 pages, accessed Jul. 26, 2012.
Ahmed, E. K. et al., "Protein modification and replicative senescence of WI-38 human embryonic fibroblasts", Aging Cell, vol. 9, pp. 252-272, (2010).
Vlassara, H. et al, "Advanced glycosylation endproducts on erythrocyte cell surface induce receptor-mediated phagocytosis by macrophages", J. Exp. Med., the Rockefeller University Press, vol. 166, pp. 539-549, (1987).
Yang, Z. et al., "Two novel rat liver membrane proteins that bind advanced glycosylation endproducts: Relationship to macrophage receptor for glucose-modified proteins", J. Exp. Med., the Rockefeller University Press, vol. 174, pp. 515-524, (1991).
Vlassara, H. et al, "Advanced glycation endproducts promote adhesion molecule (VCAM-1, ICAM-1) expression and atheroma formation in normal rabbits", Molecular Medicine, vol. 1, No. 4, pp. 447-456, (1995).
Vaysse, J. et al., "Adhesion and erythrophagocytosis of human senescent erythrocytes by autologous monocytes and their inhibition by β-galactosyl derivatives", Proc. Natl. Acad. Sci. USA, Cell Biology, vol. 83, pp. 1339-1343, (1986).
Li, Y. M. et al., "Prevention of cardiovascular and renal pathology of aging by the advanced glycation inhibitor aminoguanidine", Proc. Natl. Acad. Sci. USA, Medical Sciences, vol. 93, pp. 3902-3907, (1996).
Manesso, E. et al., "Dynamics of β-cell turnover: evidence for β-cell turnover and regeneration from sources of β-cells other than β-cell replication in the HIP rat", American Journal of Physiology Endocrinology and Metabolism, vol. 297, pp. E323-E330, (2009).

Stepanov, A.V. et al., "Design of targeted B cell killing agents", PLoS One, vol. 6, issue 6, e20991, pp. 1-10, (2011).
Fact Sheet, "Targeted Cancer Therapies", www.cancer.gov/cancertopics/factsheet/Therapy/Fs7_49.pdf, pp. 1-8, (2012).
Kay, M.M. "Generation of senescent cell antigen on old cells initiates IgG binding to a neoantigen", Cellular and Molecular Biology (Noisy-le-Grand, France), vol. 39, No. 2, pp. 131-153, (1993), Abstract Only.
Cirocchi, R. et al., "Meta-analysis of thyroidectomy with ultrasonic dissector versus conventional clamp and tie", World Journal of Surgical Oncology, vol. 8, No. 112, pp. 1-7, (2010).
Lingeman, J.E. et al., "Current perspective on adverse effects in shock wave lithotripsy", White Paper, American Urological Association Education and Research, found at www.auanet.org/content/guidelines-and-quality-care/clinical-guidelines/main-reports/whitepaper.pdf, 17 pages, (2009).
de Groot, K. et al., "Vascular endothelial damage and repair in antineutrophil cytoplasmic antibody-associated vasculitis", Arthritis & Rheumatism, vol. 56, No. 11, pp. 3847-3853, (2007).
Imani, F. et al., "Advanced glycosylation endproduct-specific receptors on human and rat t-lymphocytes mediate synthesis of interferon γ: role in tissue remodeling", J. Exp. Med., vol. 178, pp. 2165-2172, (1993).
Kirstein, M. et al., "Receptor-specific induction of insulin-like growth factor I in human monocytes by advanced glycosylation end product-modified proteins", J. Clin. Invest., vol. 90, pp. 439-446, (1992).
Le Grand, F. et al., "Skeletal muscle satellite cells and adult myogenesis", Curr. Opin. Cell Biology, vol. 19, No. 6, pp. 628-633, (2007).
Sasaki, M. et al., "Mesenchymal stem cells are recruited into wounded skin and contribute to wound repair by transdifferentiation into multiple skin cell type", the Journal of Immunology, vol. 180, pp. 2581-2587, (2008).
Misur, I. et al., "Advanced glycation endproducts in peripheral nerve in type 2 diabetes with neuropathy", Acta Diabetol, vol. 41, pp. 158-166, (2004).
Saltykov, B.B., "Mechanisms of development of diabetic macroangiopathy", Arkh Patol., vol. 63, No. 2, pp. 21-26, (2001), Abstract Only.
Grossin, N. et al., "Red blood cell adhesion in diabetes mellitus is mediated by advanced glycation end product receptor and is modulated by nitric oxide", Biorheology, vol. 46, No. 1, pp. 63-72, (2009).
Liang, Y. et al., "Rituximab for children with immune thrombocytopenia: A systematic review", PLoS One, vol. 7, issue 1, pp. 1-11, (2012).
Fehrenbach, H. et al., "Up-regulated expression of the receptor for advanced glycation end products in cultured rat hepatic stellate cells during transdifferentiation to myofibroblasts", Hepatology, vol. 34, No. 5, pp. 943-952, (2001).
Agostini, A. et al., "Targeted cargo delivery in senescent cells using capped mesoporous silica nanoparticles", Angewandte Chemie International Edition, vol. 51, pp. 10556-10560, (2012).
Larson, R.A. et al., "Tumor lysis syndrome: Definition, pathogenesis, clinical manifestations, etiology and risk factors", found at www.uptodate.com/contents/tumor-lysis-syndrome-definition-pathogenesis-clinical-manifestations-etiology-and-risk-factors?detectedLanguage=en&source=search_result&search=tumor+lysis+syndrome&selectedTitle=2~69&provider=noProvider, pp. 1-4, printed on Jun. 11, 2013.
Hansel, T.T. et al., "The safety and side effects of monoclonal antibodies", Nature Reviews, vol. 9, pp. 325-337, (2010).
Nass, N. et al., "Advanced glycation end products, diabetes and ageing", Zeitschrift fur Gerontologie und Geriatrie, vol. 40, issue 5, pp. 349-356, (2007).
Wautier, J.-L. et al., Protein Glycation: "A firm link to endothelial cell dysfunction", Circulation Research, Journal of the American Heart Association, vol. 95, pp. 233-238, (2004).
Meuter, A. et al., "Markers of cellular senescence are elevated in murine blastocysts cultured in vitro: molecular consequences of culture in atmospheric oxygen", Journal of Assisted Reproduction and Genetics, vol. 31, issue 10, pp. 1259-1267, (2014).

(56) References Cited

OTHER PUBLICATIONS

Freund, A. et al., "Inflammatory networks during cellular senescence: causes and consequences", Trends in Molecular Medicine, vol. 16, No. 5, pp. 238-246, (2010).
Hadrabová, J. et al., "Chicken immunoglobulins for prophylaxis: Effect of inhaled antibodies on inflammatory parameters in rat airways", Journal of Applied Biomedicine, 4 pages, Available online May 5, 2014.
Ferraccioli, G. et al., "Interleukin-1β and Interleukin-6 in arthritis animal models: Roles in the early phase of transition from acute to chronic inflammation and relevance for human rheumatoid arthritis", Molecular Medicine, vol. 16, issue 11-12, pp. 552-557, (2010).
Zhao, Y. et al., "The bovine antibody repertoire", Developmental & Comparative Immunology, vol. 30, issues 1-2, pp. 175-186, (2006).
Wagner, B. et al., "The complete map of the Ig heavy chain constant gene region reveals evidence for seven IgG isotypes and for IgD in the horse", Journal of Immunology, vol. 173, No. 5, pp. 3230-3242, (2004).
Strietzel, C.J. et al., "In vitro functional characterization of feline IgGs", Veterinary Immunology and Immunopathology, vol. 158, issues 3-4, pp. 214-223, (2014).
Patel, M. et al., "Sequence of the dog immunoglobulin alpha and epsilon constant region genes", Immunogenetics, vol. 41, issue 5, pp. 282-286, (1995).
Maass, D.R. et al., "Alpaca (*Lama pacos*) as a convenient source of recombinant camelid heavy chain antibodies (VHHs)", Journal of Immunology Methods, vol. 324, issues 1-2, pp. 13-25, (2007).
European Search Report dated Sep. 12, 2014 for EP application No. EP14170802.4-1408.
Fessler, J. et al., "Senescent T cells promote bone loss in rheumatoid arthritis", Abstracts of the American College of Rheumatology/Association of Rheumatology Health Professionals, Annual Scientific Meeting, Washington, DC, Nov. 9-14, 2012, Arthritis & Rheumatism, vol. 64, supplement 10, p. 2312, (2012) found at http://blackwellpublishing.com/acrmeeting/abstract.asp?MeetingID=789&id=103040.
Weyand, C.M. et al., Abstract of "T-cell aging in rheumatoid arthritis", Current Opinion in Rheumatology, vol. 26, No. 1, pp. 93-100, (2014) found at http://www.ncbi.nlm.nih.gov/m/pubmed/24296720/.
Dvergsten, J. et al., "Prevalence of functionally active, senescent T cells in juvenile idiopathic arthritis", Abstracts of the American College of Rheumatology/Association of Rheumatology Health Professionals, Annual Scientific Meeting, Philadelphia, Oct. 16-21, 2009, Arthritis & Rheumatism, vol. 60, supplement 10, p. 1313, (2009), found at http://blackwellpublishing.com/acrmeeting/abstract.asp?MeetingID=761&id=80937.
Definition of "Dissociation constant" printed from Wikipedia, the free encyclopedia on Sep. 17, 2014 found at http://en.wikipedia.org/wiki/Dissociation_constant.
Sigma-Aldrich product specification of "Nα,Nα-Bis(carboxymethyl)-L-lysine trifluoroacetate salt ≥95% (TLC)", found at http://sigmaaldrich.com/catalog/product/sigma/c3205?lang=en&region=US, printed on Sep. 17, 2014.
"Pulmatrix demonstrates iSPERSE capabilities for inhaled dry powder delivery of antibiotics and antibodies", data presented at Respiratory Drug Delivery 2012, 3 pages, printed on Sep. 4, 2014, found at http://businesswire.com/news/home/20120515005279/en/Pulmatrix-Demonstrates-iSPERSE-Capabilities-Inhaled-Dry-Powder#.VEgU4hauNbs.
Chan, A.C. et al., "Therapeutic antibodies for autoimmunity and inflammation", Nature Reviews Immunology, vol. 10, pp. 301-316, (2010).
Pradat, P.F. et al., "Abnormalities of satellite cells function in amyotrophic lateral sclerosis", Amyotrophic Lateral Sclerosis, vol. 12, No. 4, pp. 264-271, (2011).
Tchkonia, T. et al., "Cellular senescence and the senescent secretory phenotype: therapeutic opportunities", the Journal of Clinical Investigation, vol. 123, No. 3, pp. 966-972, (2013).
Kitada, K. et al., "Aldosterone induces p21-regulated apoptosis via increased synthesis and secretion of tumour necrosis factor-α in human proximal tubular cells", Clinical and Experimental Pharmacology and Physiology, vol. 39, No. 10, pp. 858-863, (2012).
Definition of "TNF inhibitor", printed from Wikipedia, the free encyclopedia on Oct. 4, 2014, 4 pages, found at http://en.wikipedia.org/wiki/TNF_inhibitor?oldid=628250399.
Definition of "Etanercept", printed from Wikipedia, the free encyclopedia on Aug. 24, 2014, 6 pages, found at http://en.wikipedia.org/wiki/Etanercept?oldid=622648157.
AbbVie, Inc., "Humira adalimumab: Learn about Humira", found at https://www.humira.com/rheumatoid-arthritis, 7 pages, printed on Aug. 11, 2014.
AbbVie, Inc., "Medication Guide for Humira", found at https://www.humira.com/rheumatoid-arthritis, 9 pages, printed on Aug. 11, 2014.
AbbVie, Inc., "Humira: A biologic that targets and helps block TNF-alpha", found at https://www.humira.com/rheumatoid-arthritis/how-humira-works-for-ra, 8 pages, printed on Aug. 11, 2014.
AbbVie, Inc., "How Humira (adalimumab) works video transcript", found at https://www.humira.com/rheumatoid-arthritis/how-humira-works-video-transcript, 5 pages, printed on Aug. 11, 2014.
AbbVie, Inc., "Humira and methotrexate—a combination that has demonstrated results", found at https://www.humira.com/rheumatoid-arthritis/humira-and-methotrexate, 7 pages, printed on Aug. 11, 2014.
Madhur, M.S. et al., "Senescent T cells and hypertension: New ideas about old cells", Hypertension, vol. 62, pp. 13-15, (2013).
James, P.E. et al., "Vasorelaxation by red blood cells and impairment in diabetes: Reduced nitric oxide and oxygen delivery by glycated hemoglobin", Circulation Research, vol. 94, pp. 976-983, (2004).
Shibayama, R. et al., "Autoantibody against N(epsilon)-(carboxymethyl)lysine: an advanced glycation end product of the Maillard reaction", Diabetes, vol. 48, No. 9, pp. 1842-1849, (1999).
Bumol, T.F. et al., "Monoclonal antibody and an antibody-toxin conjugate to a cell surface proteoglycan of melanoma cells suppress in vivo tumor growth", Proceeding of the National Academy of Science, vol. 80, pp. 529-533, (1983).
"AGEs (all species) antibody—Product Details", Antibodies Online, 4 pages, found at www.web.archive.org/web/20081229071154/http://www.antibodies-online.com/antibody/289931/AGEs+All+Species/, printed on Dec. 10, 2014.
"Antibody Engineering", Fusion Antibodies, 2 pages, found at www.web.archive.org/web/20080628225818/http://www.fusionantibodies.com/index.cfm/area/information/page/engineering?, printed on Dec. 16, 2014.
Hargreaves, R.E.G. et al., "Selective depletion of activated T cells: the CD40L-specific antibody experience", Trends in Molecular Medicine, vol. 10, No. 3, pp. 130-135, (2004).
Leinenga, G. et al., "Scanning ultrasound removes amyloid-β and restores memory in an Alzheimer's disease mouse model", Science Translational Medicine, vol. 7, issue 278, pp. 1-11, (2015).
Peppa, M. et al., "Glucose, advanced glycation end products, and diabetes complications: What is new and what works", Clinical Diabetes, vol. 21, No. 4, pp. 186-187, (2003).
Lv, Y. et al., "Low-intensity ultrasound combined with 5-aminolevulinic acid administration in the treatment of human tongue squamous carcinoma", Cellular Physiology and Biochemistry, vol. 30, pp. 321-333, (2012).
Campisi, J. et al., "Cellular senescence: when bad things happen to good cells", Nature Reviews: Molecular Cell Biology, vol. 8, pp. 729-749, (2007).
"ALSUntangled No. 23: The Rife Machine and retroviruses", Amyotrophic Lateral Sclerosis and Frontotemporal Degeneration, vol. 15, pp. 157-159, (2014).
Roylance, D., "Mechanical properties of materials", pp. 1-128, (2008), available at www.web.mit.edu/course/3/3.225/book.pdf.
Vidarsson, G. et al., "IgG subclasses and allotypes: from structure to effector functions", Frontiers in Immunology, vol. 5, article 520, pp. 1-17, (2014).

(56) References Cited

OTHER PUBLICATIONS

Lin, H-T. et al., "Stem cell therapy: an exercise in patience and prudence", Philosophical Transactions of the Royal Society B: Biological Sciences 368, (2013).
Waldmann, T.A., "Immunotherapy:past, present and future", Nature Medicine, vol. 9, No. 3, pp. 269-277, (2003).
Okamoto, T. et al., "Advanced glycation end products induce angiogenesis in vivo", Microvascular Research, vol. 63, pp. 186-195, (2002).
Nagai, R. et al., "Application of monoclonal antibody libraries for the measurement of glycation adducts", Biochemical Society Transactions, vol. 31, part 6, pp. 1438-1440, (2003).
De Genst, E. et al., "Antibody repertoire development in camelids", Developmental and Comparative Immunology, vol. 30, pp. 187-198, (2006).
Griffin, L.M. et al., "Analysis of hevy and light chain sequences of conventional camelid antibodies from *Camelus dromedarius* and *Camelus bactrianus* species", Journal of Immunological Methods, vol. 405, pp. 35-46, (2014).
Hamers-Casterman, C. et al., "Naturally occurring antibodies devoid of light chains", Nature, vol. 363, pp. 446-448, (1993).
Muyldermans, S. et al., "Sequence and structure of $V_H$ domain from naturally occurring camel heavy chain immunoglobulins lacking light chains", Protein Engineering, vol. 7, No. 9, pp. 1129-1135, (1994).
Nguyen, V. K. et al., "Camel heavy-chain antibodies: diverse germline VHH and specific mechanisms enlarge the antigen-binding repertoire", the EMBO Journal, vol. 19, No. 5, pp. 921-930, (2000).
Kirstein, et al., "Advanced protein glycosylation induces transendothelial human monocyte chemotaxis and secretion of platelet-derived growth factor: roll in vascular disease of diabetes and aging", PNAS, vol. 87, No. 22, pp. 9010-9014, (1990).
Invitation to Pay Additional Fees and Partial International Search Report dated Jan. 13, 2016 for PCT application No. PCT/US2015/050154.
Feldmann, M. et al., "Anti-TNFalpha therapy of rheumatoid arthritis: What have we learned?", Annual Review of Immunology, vol. 19, pp. 163-196, (2001).
Drinda, S. et al., "Identification of the advanced glycation end products N-carboxymethyllysine in the synovial tissue of patients with rheumatoid arthritis", Annals of the Rheumatic Diseases, vol. 61, No. 6, pp. 488-492, (2002).
Ahmad, S. et al., "Preferential recognition of epitopes on AGE-IgG by the autoantibodies in rheumatoid arthritis patients", Human Immunology, vol. 74, No. 1, pp. 23-27, (2013).
Johns, L.D., "Nonthermal effects of therapeutic ultrasound: The frequency resonance hypothesis", Journal of Athletic Training, vol. 37, No. 3, pp. 293-299, (2002).
Wang, B-L. et al., "Identification of monoclonal antibody of advanced glycation end products", Chinese Journal of Arteriosclerosis, vol. 14, No. 5, pp. 409-412, (2006).
Wang, J.C. et al., "Aging and Atherosclerosis mechanisms, functional consequences, and potential therapeutics for cellular senescence", Circulation Research, vol. 111, pp. 245-259, (2012).
Minamino, T. et al., "Vascular cell senescence contribution to Atherosclerosis", Circulation Research, vol. 100, pp. 15-26, (2007).
Isoda, K. et al., "Glycated LDL increases monocyte CC chemokine receptor 2 expression and monocyte chemoattractant protein-1-mediated chemotaxis", Atherosclerosis, vol. 198, No. 2, pp. 307-312, (2008).
Roos, C.M. et al., "Chronic senolytic treatment alleviates established vasomotor dysfunction in aged or atherosclerotic mice", Aging Cell, 8 pages, (2016).
Hall, B.M. et al., "Aging of mice is associated with p16(Ink4a)- and β-galactosidase-positive macrophage accumulation that can be induced in young mice by senescent cells", Aging, vol. 8, No. 7, pp. 1-18, (2016).
Mera, K. et al., "An autoantibody against $N^\epsilon$-(carboxyethyl)lysine (CEL): Possible involvement in the removal of CEL-modified proteins by macrophages", Biochemical and Biophysical Research Communications, vol. 407, pp. 420-425, (2011).
Reddy, S. et al., "$N^\epsilon$-(Carboxymethyl)lysine is a dominant advanced glycation end product (AGE) antigen in tissue proteins", Biochemistry, vol. 34, pp. 10872-10878, (1995).
Katcher, H.L., "Studies that shed new light on aging", Biochemistry (Moscow), vol. 78, No. 9, pp. 1061-1070, (2013).
Naylor, R.M. et al., "Senescent Cells: A novel therapeutic target for aging and age-related diseases", Clinical Pharmacology & Therapeutics, vol. 93, No. 1, pp. 105-116, (2013).
Beaulieu, L-P. et al., "Inhibitory effect of the cree traditional medicine wiishichimanaanh (vaccinium vitis-idaea) on advanced glycation endproduct formation: identification of active principles", Phytotherapy Research, vol. 24, pp. 741-747, (2010).
Ulrich, P. et al., "Protein glycation, diabetes, and aging", Recent Progress in Hormone Research, vol. 56, pp. 1-21, (2000).
Van Heijst, J.W.J. et al., "Advanced glycation end products in human cancer tissues: detection of $N^\epsilon$-(carboxymethyl)lysine and argpyrimidine", Annals of the New York Academy of Sciences, vol. 1043, pp. 725-733, (2005).
Fielding, R.A. et al., "Sarcopenia: An undiagnosed condition in older adults. Current consensus definition: Prevalence, etiology, and consequences", Journal of the American Medical Directors Association, vol. 12, No. 4, pp. 249-256, (2011).
Definition of "Sarcopenia", printed from Wikipedia, the free encyclopedia on Jul. 25, 2016, 5 pages, found at http://en.wikipedia.org/wiki/Sarcopenia.
"What is Sarcopenia?", International Osteoporosis Foundation, 2 pages, found at www.iofbonehealth.org/what-sarcopenia, (2014).
"Sarcopenia with aging", Webmd, 2 pages, found at www.webmd.com/healthy-aging/sarcopenia-with-aging, (2014).
Definition of "Keyhole limpet hemocyanin", printed from Wikipedia, the free encyclopedia on Jul. 25, 2016, 4 pages, found at https://en.wikipedia.org/wiki/Keyhole_limpet_hemocyanin.
Cell Biolabs, Inc., "CML-BSA Product Data Sheet", 3 pages, found at http://www.cellbiolabs.com/sites/defaultifiles/STA-314-cml-bsa.pdf, (2010).
Cell Biolabs, Inc., "CML (N-epsilon-(Caboxymethyl)Lysine) Assays and Reagents", 1 page, found at http://www.cellbiolabs.com/cml-assays, (2014).
Cruz-Jentoft, A.J. et al., "Sarcopenia: European consensus on definition and diagnosis", Age and Ageing, vol. 39, pp. 412-423, (2010).
Rolland, Y. et al., "Sarcopenia: Its assessment, etiology, pathogenesis, consequences and future perspectives", the Journal of Nutrition, Health & Aging, vol. 12, No. 7, pp. 433-450, (2008).
Centers for Disease Control and Prevention, "Vaccine excipient and media summary", 4 pages, found at www.cdc.gov/vaccines/pubs/pinkbook/downloads/appendices/B/excipient-table-2.pdf?utm_content=buffer4538f&utm_medium=social&utm_source=linkedin.com&utm_campaign=buffer, (2015).
Definition of "N(6)-Carboxymethyllysine", printed from Wikipedia, the free encyclopedia on Dec. 8, 2013, 1 page, found at http://en.wikipedia.org/wiki/N(6)-Carboxymethyllysine.
Definition of "Lysine", printed from Wikipedia, the free encyclopedia on Dec. 8, 2013, 1 page, found at http://en.wikipedia.org/wiki/Lysine.
Jarvis, L.M., "Rethinking antibody-drug conjugates", Chemical & Engineering News, vol. 90, issue 25, pp. 12-18, (2012).
Mullin, R., "Cell-free approach to antibody-drug conjugates", Chemical & Engineering News, vol. 91, issue 44, 2 pages, (2013).
Thayer, A.M., "Building antibody-drug conjugates", Chemical & Engineering News, vol. 92, issue 3, pp. 13-21, (2014).
Feige, M.J. et al., "The structural analysis of shark IgNAR antibodies reveals evolutionary principles of immunoglobulins", Proceedings of the National Academy of Sciences, vol. 111, No. 22, pp. 8155-8160, (2014).
Philipot, D. et al.,"$p16^{INK4a}$ and its regulator miR-24 link senescence and chondrocyte terminal differentiation-associated matrix remodeling in osteoarthritis", Arthritis Research & Therapy, vol. 16, No. 1, pp. 1-12, (2014).
International Search Report and Written Opinion dated Mar. 31, 2016 for PCT application No. PCT/US2015/050154.

(56) References Cited

OTHER PUBLICATIONS

Zhu, Y. et al., "The achilles' heel of senescent cells: from transcriptome to senolytic drugs", Aging Cell, vol. 14, pp. 644-658, (2015).

Zhu, L. et al., "Immunization with advanced glycation end products modified low density lipoprotein inhibits atherosclerosis progression in diabetic apoE and LDLR null mice", Cardiovascular Diabetology, vol. 13, No. 151, pp. 1-12, (2014).

DeNardo, S.J. et al., "Development of tumor targeting bioprobes ($^{111}$in-chimeric L6 monoclonal antibody nanoparticles) for alternating magnetic field cancer therapy", Clinical Cancer Research, vol. 11, 19 supplemental, pp. 7087s-7092s, (2005).

Chen, L. et al., "Cytolysis of human erythrocytes by a covalent antibody-selenium immunoconjugate", Free Radical Biology & Medicine, vol. 19, No. 6, pp. 713-724, (1995).

Yuan, Y. et al., "Advanced glycation end products (AGEs) increase human mesangial foam cell formation by increasing Golgi SCAP glycosylation in vitro", American Journal of Physiology—Renal Physiology, vol. 301.1, pp. F236-F243, (2011).

Hashimoto, M. et al., "Elimination of p19$^{ARF}$-expressing cells enhances pulmonary function in mice", JCI Insight, vol. 1, No. 12, pp. 1-15, (2016).

Yan, S.F. et al., "Soluble RAGE: Therapy & biomarker in unraveling the RAGE axis in chronic disease and aging", Biochemical Pharmacology, vol. 79, No. 10, pp. 1379-1386, (2010).

Xue, J. et al., "Advanced glycation end product (AGE) recognition by the receptor for AGEs (RAGE)", Structure, vol. 19, No. 5, pp. 722-732, (2011).

Chang, J. et al., "Clearance of senescent cells by ABT263 rejuvenates aged hematopoietic stem cells in mice", Nature Medicine, vol. 22, No. 1, pp. 78-83, (2016).

Geiger, H., "Depleting senescent cells to combat aging", Nature Medicine, vol. 22, No. 1, pp. 23-24, (2016).

Ni, J. et al., "Plasma protein pentosidine and carboxymethyllysine, biomarkers for age-related macular degeneration", Molecular & Cellular Proteomics, vol. 8, No. 8, pp. 1921-1933, (2009).

R&D Systems, a biotechne brand, product specification of "Carboxymethyl Lysine Antibody", found at https://www.rndsystems.com/products/carboxymethyl-lysine-antibody-318003_mab3247, 1 page, (2015).

Schalkwijk, C.G. et al., "Increased accumulation of the glycoxidation product N$^{\epsilon}$-(carboxymethyl)lysine in hearts of diabetic patients: generation and characterization of a monoclonal anti-CML antibody", Biochimica et Biophysica Acta (BBA)-Molecular and Cell Biology of Lipids, vol. 1636, No. 2, pp. 82-89, (2004).

LaPak, K.M. et al., "The molecular balancing act of p16$^{INK4a}$ in cancer and aging", Molecular Cancer Research, vol. 12, No. 2, pp. 167-183, (2013).

Larsen, S.A. et al., "Glucose metabolite glyoxal induces senescence in telomerase-immortalized human mesenchymal stem cells", Chemistry Central Journal, vol. 6, No. 18, pp. 1-13, (2012).

Ahmed, M.U. et al., "N$^{\epsilon}$-(carboxymethyl)lysine, a product of the chemical modification of proteins by methylglyoxal, increases with age in human lens proteins", Biochemical Journal, vol. 324, pp. 565-570, (1997).

Dunn, J.A. et al., "Age-dependent accumulation of N$^{\epsilon}$-(Carboxymethyl)lysine and N$^{\epsilon}$-(Carboxymethyl)hydroxylysine in human skin collagen", Biochemistry, vol. 30, pp. 1205-1210, (1991).

Finco, A.B. et al., "Generation and characterization of monoclonal antibody against advanced glycation end products in chronic kidney disease", Biochemistry and Biophysics Reports, vol. 6, pp. 142-148, (2016).

International Search Report and Written Opinion dated Aug. 10, 2016 for PCT application No. PCT/US2016/034880.

Liu, H. et al., "Abstract 154: Vaccination using advanced glycation end product of low-density lipoprotein pulsed dendritic cells reduces atherosclerosis in diabetic apoe$^{-/-}$ mice", Arteriosclerosis, Thrombosis, and Vascular Biology, pp. 1-4, (2012).

Mashitah, M.W. et al., "Immunization of AGE-modified albumin inhibits diabetic nephropathy progression in diabetic mice", Diabetes, Metabolic Syndrome and Obesity: Targets and Therapy, vol. 8, pp. 347-355, (2015).

Sayej, W.N. et al., "Advanced glycation end products induce obesity and hepatosteatosis in CD-1 wild-type mice", BioMed Research International, vol. 6, No. 39, pp. 1-12, (2016).

Srikanth, V. et al., "Advanced glycation endproducts and their receptor RAGE in alzheimer's disease", Neurobiology of Aging, vol. 32, No. 5, pp. 763-777, (2011).

International Search Report and Written Opinion dated Dec. 2, 2016 for PCT application No. PCT/US2016/039076.

Fu, M-X. et al., "The advanced glycation end product, N-(Carboxymethyl)lysine, is a product of both lipid peroxidation and glycoxidation reactions", the Journal of Biological Chemistry, vol. 271, No. 17, pp. 9982-9986, (1996).

Jorgensen, L. et al., "The relationship between atherosclerosis of the thoracic aorta and renal scarring in an autopsy material", Acta Pathol Microbiol Immunol Scand A., vol. 93, No. 5, pp. 251-255, (1985) Abstract Only.

"Senescent cells drive plaque formation in animal models of atherosclerosis, research shows", Mayo Clinic, pp. 1-2, (2016), found at www.news-medical.net/news/20161027/Senescent-cells-drive-plaque-formation-in-animal-models-of-atherosclerosis-research-shows.aspx.

Baker, D.J. et al., "Naturally occurring p16$^{Ink4\epsilon}$-positive cells shorten healthy lifespan", Nature, vol. 530, issue 7589, pp. 184-189, (2016).

Raquib, R., "The key to youth via senescent cell removal", Young Investigators Review, pp. 1-4, (2017), found at sbyireview.com/2017/01/23/the-key-to-youth-via-senescent-cell-removal.

Tiner, S., "Mayo clinic research links senescent cells and atherosclerosis progression", Mayo Clinic News Network, pp. 1-3, (2016), found at newsnetwork.mayoclinic.org/discussion/mayo-clinic-research-links-senescent-cells-and-atherosclerosis-progression.

Wiley, C., "Aging Fundamentals: Cellular senescence", Science of Aging Blog at the Buck Institute, pp. 1-4, (2015), found at sage.buckinstitute.org/aging-fundamentals-cellular-senescence.

Arichika, S. et al., "Correlation of retinal arterial wall thickness with atherosclerosis predictors in type 2 diabetes without clinical retinopathy", British Journal of Ophthalmology, vol. 101, pp. 69-74, (2017).

Lin, Z. et al., "Vaccination against AGE-LDL significant attenuates atherosclerosis in diabetic apoe mice", Heart, vol. 97, No. 21, supplement 3, p. A18, (2011) Abstract Only.

Thompson, L.V., "Age-related muscle dysfunction", Experimental Gerontology, vol. 44, pp. 106-111, (2009).

Sun, K. et al., "Elevated serum carboxymethyl-Lysine, an advanced glycation end product, predicts severe walking disability in older women: The women's health and aging study I", Journal of Aging Research, vol. 2012, pp. 1-8, (2012).

Kislinger, T. et al., "N$^{\epsilon}$-(Carboxymethyl)Lysine adducts of proteins are ligands for receptor for advanced glycation end products that activate cell signaling pathways and modulate gene expression", the Journal of Biological Chemistry, vol. 274, No. 44, pp. 31740-31749, (1999).

Nakayama, H. et al., "Production and characterization of antibodies to advanced glycation products on proteins", Biochemical and Biophysical Research Communications, vol. 162, No. 2, pp. 740-745, (1989).

Gupta, R.K., "Aluminum compounds as vaccine adjuvants", Advanced Drug Delivery Review, vol. 32, No. 3, pp. 155-172, (1998), Abstract Only.

Tracy, J.M. et al., "Preservatives for poliomyelitis (Salk) vaccine II: Formaldehyde and esters of p-hydroxybenzoic acid", Journal of Pharmaceutical Sciences, vol. 53, Issue 6, pp. 659-663, (1964), Abstract Only.

Koito, W. et al., "Conventional antibody against N$^{\epsilon}$-(Carboxymethyl)Lysine (CML) shows cross-reaction to N$^{\epsilon}$-(Carboxyethyl)Lysine (CEL): Immunochemical quantification of CML with a specific antibody", the Journal of Biochemistry, vol. 135, No. 6, pp. 831-837, (2004).

Product Description of "Anti-Advanced Glycation End Products (AGE), Carboxy-Methyl Lysine (CML) [6C7] Antibody", Kerafast,

(56) References Cited

OTHER PUBLICATIONS www.kerafast.com/product/1779/anti-advanced-glycation-end-products-age-carboxy-methyl-lysine-cml-6c7-antibody, printed on Feb. 2, 2017.

Ikeda, K. et al., "N$^\varepsilon$-(Carboxymethyl)lysine protein adduct is a major immunological epitope in proteins modified with advanced glycation end products of the maillard reaction", Biochemistry, vol. 35, No. 24, pp. 8075-8083, (1996).

Dunn, J.A. et al., "Oxidation of glycated proteins: Age-dependent accumulation of N$^\varepsilon$-(Carboxymethyl)lysine in lens proteins", Biochemistry, vol. 28, No. 24, pp. 9464-9468, (1989).

Peppa, M. et al., "The role of advanced glycation end products in the development of atherosclerosis", Current Diabetes Reports, vol. 4, pp. 31-36, (2004).

Glenn, J.V. et al., "The role of advanced glycation end products in retinal ageing and disease", Biochimica Et Biophysica Acta, vol. 1790, No. 10. pp. 1109-1116, (2009).

European Search Report dated Feb. 21, 2017 for EP application No. 16198527.0.

Xu, M. et al., "Transplanted senescent cells induce an osteoarthritis-like condition in mice", the Journals of Gerontology Series A: Biological Sciences and Medical Sciences, pp. 1-6, (2016).

Ratliff, M. et al., "In senescence, age-associated B cells secrete TNFα and inhibit survival of B-cell precursors", Aging Cell, vol. 12, pp. 303-311, (2013).

Manestar-Blazic, T. et al., "The dynamic of senescent cells accumulation can explain the age-specific incidence of autoimmune diseases", Medical Hypotheses, vol. 73, pp. 667-669, (2009).

Tchkonia, T. et al., "Fat tissue, aging, and cellular senescence", Aging Cell, vol. 9, pp. 667-684, (2010).

Robbins, P. et al., "Scripps research, Mayo Clinic scientists find new class of drugs that dramatically increases healthy lifespan", the Scripps Research Institute, pp. 1-3, found at www.scripps.edu/news/press/2015/20150309agingcell.html, printed on Mar. 14, 2015.

Dorr, J.R. et al., "Synthetic lethal metabolic targeting of cellular senescence in cancer therapy", Nature, vol. 501, No. 7467, pp. 421-425, (2013).

Xu, M. et al., "Targeting senescent cells enhances adipogenesis and metabolic function in old age", eLife, vol. 4, pp. 1-20, (2015).

Minamino, T. et al., "Endothelial cell senescence in human atherosclerosis: Role of telomere in endothelial dysfunction", Circulation, vol. 105, issue 13, pp. 1541-1544, (2002).

Takino, J-I. et al., "Cancer malignancy is enhanced by glyceraldehyde-derived advanced glycation end-products", Journal of Oncology, vol. 2010, pp. 1-8, (2010).

Laberge, R-M. et al., "Epithelial-mesenchymal transition induced by senescent fibroblasts", Cancer Microenvironment, vol. 5, pp. 39-44, (2012).

Abe, R. et al., "Regulation of human melanoma growth and metastasis by AGE-AGE receptor interactions", Journal of Investigative Dermatology, vol. 122, No. 2, pp. 461-467, (2004).

Porporato, P.E. et al., "A mitochondrial switch promotes tumor metastasis", Cell Reports, vol. 8, pp. 754-766, (2014).

Boquio, A. et al., "Reversible cell cycle inhibition and premature aging features imposed by conditional expression of p16$^{Ink4a}$", Aging Cell, vol. 14, pp. 139-147, (2015).

Nelson, G. et al., "A senescent cell bystander effect: senescence-induced senescence", Aging Cell, vol. 11, pp. 345-349, (2012).

Rayess, H. et al., "Cellular senescence and tumor suppressor gene p16", International Journal of Cancer, vol. 130, No. 8, pp. 1715-1725, (2012).

Greenfieldboyce, N., "Boosting life span by clearing out cellular clutter", npr.org, 4 pages, found at www.npr.org/sections/health-shots/2016/02/03/465354874/boosting-lifespan-by-clearing-out-cellular-clutter, printed on Feb. 4, 2016.

Matus, D.Q. et al., "Invasive cell fate requires G1 cell-cycle arrest and histone deacetylase-mediated changes in gene expression", Developmental Cell, vol. 35, pp. 162-174, (2015).

Stony Brook University, "Targeting invasive cells not dividing cells to halt cancer, study suggests", ScienceDaily, pp. 1-2, found at www.sciencedaily.com/releases/2015/10/151026181610.htm, (2015).

Liu, D. et al., "Senescent human fibroblasts increase the early growth of xenograft tumors via matrix metalloproteinase secretion", Cancer Research, vol. 67, No. 7, pp. 3117-3126, (2007).

Hoke, Z. "Belgian researchers discover way to block cancer metastasis", VOZ News, pp. 1-3, found at www.voanews.com/a/belgian-researchers-discover-way-to-block-cancer-metastasis/2453790.html, (2014).

Di, G-H. et al., "IL-6 secreted from senescent mesenchymal stem cells promotes proliferation and migration of breast cancer cells", PloS one, vol. 9, No. 11, pp. 1-15, (2014).

Huang, L-W. et al., "P16$^{Ink4a}$ overexpression predicts lymph node metastasis in cervical carcinomas", Journal of Clinical Pathology, vol. 65, pp. 117-121, (2012).

Romagosa, C. et al., "P16$^{Ink4a}$ overexpression in cancer: a tumor suppressor gene associated with senescence and high-grade tumors", Oncogene, vol. 30, pp. 2087-2097, (2011).

Terman, A. et al., "Mitochondrial turnover and aging of long-lived postmitotic cells: The mitochondrial-lysosomal axis theory of aging", Antioxidants & Redox Signaling, vol. 12, No. 4, pp. 503-535, (2010).

Ralph, A. et al., "P16 and HPV discordance in metastatic carcinoma of cervical lymph nodes of unknown primary", Clinical Case Reports, vol. 3, No. 10, pp. 817-818, (2015).

Hipkiss, A.R. "Aging, proteotoxicity, mitochondria, glycation, NAD+ and carnosine: possible inter-relationships and resolution of the oxygen paradox", Frontiers in Aging Neuroscience, vol. 2, article 10, pp. 1-6, (2010).

Bakala, H. et al., "Changes in rat liver mitochondria with aging Ion protease-like activity and N$^\varepsilon$-carboxymethyllysine accumulation in the matrix", European Journal of Biochemistry, vol. 270, No. 10, pp. 2295-2302, (2003).

Leslie, M. "Suicide of aging cells prolongs life span in mice", Sciencemag.org, pp. 1-4, found at www.sciencemag.org/news/2016/02/suicide-aging-cells-prolongs-life-span-mice, (2016).

Eto, H. et al., "Selective imaging of malignant ascites in a mouse model of peritoneal metastasis using in vivo dynamic nuclear polarization-magnetic resonance imaging", Analytical Chemistry, vol. 88, pp. 2021-2027, (2016).

May Jr. K.F. et al., "Anti-human CTLA-4 monoclonal antibody promotes T-cell expansion and immunity in a hu-PBL-SCID model: a new method for preclinical screening of costimulatory monoclonal antibodies", Blood, vol. 105, pp. 1114-1120, (2005).

Schmitt, C.A. "Cellular senescence and cancer treatment", Biochimica et Biophysica Acta—Reviews on Cancer, vol. 1775, No. 1, pp. 5-20, (2007).

Gordon, R.R. et al., "Cellular senescence and cancer chemotherapy resistance", Drug Resistance Updates, vol. 15, No. 1-2, pp. 123-131, (2012).

Eyman, D. et al., "CCL5 secreted by senescent aged fibroblasts induces proliferation of prostate epithelial cells and expression of genes that modulate angiogenesis", Journal of Cellular Physiology, vol. 220, No. 2, pp. 376-381, (2009).

Nguyen, D.X. et al., "Metastasis: from dissemination to organ-specific colonization", Nature Reviews Cancer, vol. 9, No. 4, pp. 274-284, (2009).

Smit, M.A. et al., "Deregulating EMT and senescence: Double impact by a single twist", Cancer Cell, pp. 5-7, (2008).

Degenhardt, T.P. et al., "Chemical modification of proteins by methylglyoxal", Cellular and Molecular Biology (Noisy-le-Grand, France), vol. 44, No. 7, pp. 1139-1145, (1998) Abstract Only.

Gao, S.H. et al., "Monoclonal antibody humanness score and its applications", BMC Biotechnology, vol. 13, No. 1, pp. 1-12, (2013).

ClinicalTrials.gov, "A study evaluating the safety of ABT-263 in combination with etoposide/cisplatin in subjects with cancer", ClinicalTrials.gov, 4 pages, found at https://clinicaltrials.gov/ct2/show/NCT00878449?term=A+study+evaluating+the+safety+of+ABT-263+in+combination+with+etoposide%2Fcisplatin+in+subjects+with+cancer&rank=1, printed on Aug. 4, 2016.

(56) References Cited

OTHER PUBLICATIONS

Keating, D.J. "Mitochondrial dysfunction, oxidative stress, regulation of exocytosis and their relevance to neurodegenerative diseases", vol. 104, No. 2, pp. 298-305, (2008). Abstract Only.
Sas, K. et al., "Mitochondria, metabolic disturbances, oxidative stress and the kynurenine system, with focus on neurodegenerative disorders", Journal of the neurological sciences, vol. 257, No. 1, pp. 221-239, (2007). Abstract Only.
Ott, M. et al., "Mitochondria, oxidative stress and cell death", Apoptosis, vol. 12, No. 5, pp. 913-922, (2007). Abstract Only.
Trushina, E. et al., "Oxidative stress and mitochondrial dysfunction in neurodegenerative diseases", Neuroscience, vol. 145, No. 4, pp. 1233-1248, (2007). Abstract Only.
Moreira, P.I. et al., "Lipoic acid and N-acetyl cysteine decrease mitochondrial-related oxidative stress in Alzheimer disease patient fibroblasts", Journal of Alzheimer's Disease, vol. 12, No. 2, pp. 195-206, (2007). Abstract Only.
Yel, L. et al., "Thimerosal induces neuronal cell apoptosis by causing cytochrome c and apoptosis-inducing factor release from mitochondria", International Journal of Molecular Medicine, vol. 16, No. 6, pp. 971-977, (2005). Abstract Only.
Humphrey, M.L. et al., "Mitochondrial mediated thimerosal-induced apoptosis in a human neuroblastoma cell line (SK-N-SN)", Neurotoxicology, vol. 26, No. 3, pp. 407-416, (2005). Abstract Only.
Makani, S. et al., "Biochemical and molecular basis of thimerosal-induced apoptosis in T cells: a major role of mitochondrial pathway", Genes and Immunity, vol. 3, No. 5, pp. 270-278, (2002). Abstract Only.
Freitag, H. et al., "Inhibition of malate transport and activation of phosphate transport in mitochondria by ethylmercurithiosalicylate", FEBS Letters, vol. 117, No. 1, pp. 149-151, (1980). Citation Only.
Freitag, H. et al., "Ethylmercurithiosalicylate—a new reagent for the study of phosphate transport in mitochondria", FEBS Letters, vol. 114, No. 2, pp. 295-298, (1980). Citation Only.
Windham, G.C. et al., "Autism spectrum disorders in relation to distribution of hazardous air pollutants in the San Francisco bay area", Environmental Health Perspectives, pp. 1438-1444, (2006). Citation Only.
Ooe, H. et al., "Induction of reactive oxygen species by bisphenol A and abrogation of bisphenol A-induced cell injury by DJ-1", Toxicological Sciences, vol. 88, No. 1, pp. 114-126, (2005). Abstract Only.
Hanzel, C.E. et al., "Thallium induces hydrogen peroxide generation by impairing mitochondrial function", Toxicology and Applied Pharmacology, vol. 216, No. 3, pp. 485-492, (2006). Abstract Only.
Murugavel, P. et al., "Cadmium induced mitochondrial injury and apoptosis in vero cells: protective effect of diallyl tetrasufide from garlic", the International Journal of Biochemistry & Cell Biology, vol. 39, No. 1, pp. 161-170, (2007). Abstract Only.
Lasfer, M. et al., "Cadmium induces mitochondria-dependent apoptosis of normal human hepatocytes", Cell Biology and Toxicology, vol. 24, No. 1, pp. 55-62, (2008). Abstract Only.
Gash, D.M. et al., "Trichloroethylene: Parkinsonism and complex 1 mitochondrial neurotoxicity", Annals of neurology, vol. 63, No. 2, pp. 184-192, (2008). Abstract Only.
Banerjee, N. et al., "Arsenic-induced mitochondrial instability leading to programmed cell death in the exposed individuals", Toxicology, vol. 246, No. 2, pp. 101-111, (2008). Abstract Only.
Partridge, M.A. et al., "Arsenic induced mitochondrial DNA damage and altered mitochondrial oxidative function: Implication for genotoxic mechanisms in mammalian cells", Cancer Research, vol. 67, No. 11, pp. 5239-5247, (2007). Abstract Only.
Santra, A. et al., "Arsenic induces apoptosis in mouse liver is mitochondria dependent and is abrogated by N-acetylcysteine", Toxicology and Applied Pharmacology, vol. 220, No. 2, pp. 146-155, (2007). Abstract Only.
Bouchard, H. et al., "Antibody-drug conjugates—A new wave of cancer drugs", Bioorganic & Medicinal Chemistry Letters, vol. 24, pp. 5357-5363, (2014).
Yang, H.M. et al., "Doxorubicin conjugated with a monoclonal antibody directed to a human melanoma-associated proteoglycan suppresses the growth of established tumor xenografts in nude mice", Proceeding of the National Academy of Science, vol. 85, pp. 1189-1193, (1988).
Childs, B.G. et al., "Senescent intimal foam cells are deleterious at all stages of atherosclerosis", Science, vol. 354, No. 6311, pp. 472-477, (2016).
Loaiza, N. et al., "Cellular senescence and tumor promotion: Is aging the key?", Biochimica et Biophysica Acta, vol. 1865, pp. 155-167, (2016).
Rodier, F. et al., "Four faces of cellular senescence", the Journal of Cell Biology, vol. 192, No. 4, pp. 547-556, (2011).
Shay, J.W. et al., "Hallmarks of senescence in carcinogenesis and cancer therapy", Oncogene, vol. 23, pp. 2919-2933, (2004).
Davalos, A.R. et al., "Senescent cells as a source of inflammatory factors for tumor progression", Cancer Metastasis Reviews, vol. 29, pp. 273-283, (2010).
Roninson, I.B., "Tumor cell senescence in cancer treatment", Cancer Research, vol. 63, pp. 2705-2715, (2003).
International Search Report and Written Opinion dated May 17, 2017 for PCT application No. PCT/US2017/018185.
Kobayashi, S. et al., "Overproduction of N(epsilon)-(carboxymethyl) lysine-induced neovascularization in cultured choroidal explant of aged rat", Biological & Pharmaceutical Bulletin, vol. 30, No. 1, pp. 133-138, (2007).
Foster, D. et al., "AGE metabolites: A biomarker linked to cancer disparity?" Cancer Epidemiology, Biomarkers and Prevention, vol. 23, No. 10, pp. 2186-2191, (2014).
Mir, A.R. et al., "Structural changed in histone H2A by methylglyoxal generate highly immunogenic amorphous aggregates with implications in auto-immune response in cancer", Glycobiology, vol. 26, No. 2, pp. 129-141, (2016).
Ko, S-Y. et al., "Cell migration is regulated by AGE-RAGE interaction in human oral cancer cells in vitro", PLOS One, vol. 9, No. 10, pp. 1-9, (2014).
Chen, H. et al., "Advanced glycation end products increase carbohydrate responsive element binding protein expression and promote cancer cell proliferation", Molecular and Cellular Endocrinology, vol. 395, No. 1-2, pp. 69-78, (2014).
Mercado-Pimentel, M.E. et al., "The S100P/RAGE signaling pathway regulates expression of microRNA-21 in colon cancer cells", FEBS Letters, vol. 589, No. 18, pp. 2388-2393, (2015).
Product description, "Carboxymethyl Lysine Antibody", R&D Systems, a biotechne brand, catalog No. MAB3247, 1 page, found at https://resources.rndsystems.com/pdfs/datasheets/mab3247.pdf, (2015).
Bhat, R. et al., "Astrocyte senescence as a component of Alzheimer's Disease", PLOS One, vol. 7, No. 9, pp. 1-10, (2012).
Flanary, B.E. et al., "Evidence that aging and amyloid promote microglial cell senescence", Rejuvenation Research, vol. 10, No. 1, pp. 61-74, (2007).
Takeda, A. et al., "Advanced glycation end products co-localize with astrocytes and microglial cells in Alzheimer's disease brain", Acta Neuropathologica, vol. 95, pp. 555-558, (1998).
Chinta, S.J. et al., "Environmental stress, ageing and glial cell senescence: a novel mechanistic link to Parkinson's disease?", Journal of internal Medicine, vol. 273, pp. 429-436, (2013).
Mori, M., "The Parkinsonian Brain: Cellular senescence and neurodegeneration", SAGE, found at sage.buckinstitute.org/the-parkinsonian-brain-cellular-senescence-and-neurodegeneration, (2015).
Das, M.M. et al., "Astrocytes show reduced support of motor neurons with aging that is accelerated in a rodent model of ALS", Neurobiology of Aging, vol. 36, pp. 1130-1139, (2015).
Luessi, F. et al., "Neurodegeneration in multiple sclerosis: novel treatment strategies", Expert Review of Neurotherapeutics, vol. 12, No. 9, pp. 1061-1077, (2012).
Wright, W.E., "Myoblast senescence in Muscular Dystrophy", Experimental Cell Research, vol. 157, pp. 343-354, (1985).
King, O.D., et al., "The tip of the iceberg: RNA-binding proteins with prion-like domains in neurodegenerative disease", Brain Research, vol. 1462, pp. 61-80, (2012).

(56) References Cited

OTHER PUBLICATIONS

Dobson, D.M., "The structural basis of protein folding and its links with human disease", Philosophical Transactions of the Royal Society of London B: Biological Sciences, vol. 356, No. 1406, pp. 133-145, (2001).
Kato, S. et al., "Advanced glycation endproduct-modified superoxide dismutase-1 (SOD1)-positive inclusions are common to familial amyotrophic lateral sclerosis patients with SOD1 gene mutations and transgenic mice expressing human SOD1 with a G85R mutation", Acta Neuropathologica, vol. 100, pp. 490-505, (2000).
International Search Report and Written Opinion dated Sep. 29, 2017 for PCT application No. PCT/US2017/027773.
Capparelli, C. et al., "Autophagy and senescence in cancer-associated fibroblasts metabolically supports tumor growth and metastasis via glycolysis and ketone production", Cell Cycle, vol. 11, No. 12, pp. 2285-2302, (2012).
""Shelf life" of blood? Shorter than we think", Johns Hopkins Medicine, pp. 1-2 found at www.hopkinsmedicine.org/news/media/releases/shelf_life_of_blood_shorter_than_we_think, (2013).
Garay-Sevilla, M.E. et al., "Advanced glycosylation end products in skin, serum, saliva and urine and its association with complications of patients with Type 2 diabetes mellitus", Journal of Endocrinological Investigation, vol. 28, No. 5, pp. 223-230, (2005).
Joyal, S.V., "Aging and Glycation", Life Extension Magazine, issue 4, pp. 1-7, found at www.lifeextension.com/Magazine/2008/4/Aging-And-Glycation/Page-01, (2008).
Egberts, J-H. et al., "Anti-tumor necrosis factor therapy inhibits pancreatic tumor growth and metastasis", Cancer Research, vol. 68, pp. 1443-1450, (2008).
Lowe, R. et al., "Buccals are likely to be a more informative surrogate tissue than blood for epigenome-wide association studies", Epigenetics, vol. 8, No. 4, pp. 445-454, (2013).
Bian, C. et al., "Clinical outcome and expression of mutant P53, P16, and Smad4 in lung adenocarcinoma: a prospective study", World Journal of Surgical Oncology, vol. 13, No. 128, pp. 1-8, (2015).
Tape, C.J. et al., "Oncogenic KRAS regulates tumor cell signaling via stromal reciprocation", Cell, vol. 165, pp. 910-920, (2016).
Product description for "CD8+CD57+ T Cell Isolation Kit, human", Miltenyi Biotec, pp. 1-4, found at www.miltenyibiotec.com/en/products-and-services/macs-cell-separation/cell-separation-reagents/t-cells/cd8-cd57-t-cell-isolation-kit-human.aspx, printed on Aug. 16, 2017.
Warrington, K.J. et al., "CD28 loss in senescent CD4+ T cells: reversal by interleukin-12 stimulation", Blood, vol. 101, No. 9, pp. 3543-3549, (2003).
Kared, H. et al., "CD57 in human natural killer cells and T-lymphocytes", Cancer Immunology, Immunotherapy, vol. 65, issue 4, pp. 441-452, (2016).
Li, Z. et al., "Cdkn2a suppresses metastasis in squamous cell carcinomas induced by the gain-of-function mutant $p53^{R172H}$", the Journal of Pathology, vol. 240, issue 2, pp. 224-234, (2016). (Abstract Only).
Demaria, M. et al., "Cellular senescence promotes adverse effects of chemotherapy and cancer relapse", Cancer Discovery, vol. 7, pp. 165-176, (2017).
Niu, L. et al., "Free and protein-bound $N^\epsilon$-carboxymethyllysine and $N^\epsilon$-carboxyethyllysine in fish muscle: Biological variation and effects of heat treatment", Journal of Food Composition and Analysis, vol. 57, pp. 56-63, (2017).
Yoon, M-S. et al., "Characterisation of advanced glycation endproducts in saliva from patients with diabetes mellitus", Biochemical and Biophysical Research Communications, vol. 323, issue 2, pp. 377-381, (2004).
Product description for "Carboxymethyl Lysine (CML) ELISA", Kamiya Biomedical Company, pp. 1-7, found at www.k-assay.com/pdf/KT-32428.pdf, printed on Aug. 16, 2017.
Baar, M.P. et al., "Targeted apoptosis of senescent cells restores tissue homeostasis in response to chemotoxicity and aging", Cell, vol. 169, pp. 132-147, (2017).
Kim, Y.H. et al., "Senescent tumor cells lead the collective invasion in thyroid cancer", Nature Communications, pp. 1-14, (2017).
Ciccone, T.G. et al., "Reversing OA—new treatment on the horizon", Practical Pain Management, pp. 1-5, found at www.practicalpainmanagement.com/resources/news-and-research/reversing-oa-new-treatment-horizon, printed on Aug. 17, 2017.
Cook, L.S., "Learning about blood component therapy", Nursing, vol. 39, No. 4, pp. 30-33, (2009).
Landesberg, R. et al., "The expression of the receptor for glycation endproducts (RAGE) in oral squamous cell carcinomas", Oral Surgery Oral Medicine Oral Pathology Oral Radiology, vol. 105, issue 5, pp. 617-624, (2008).
Zhou, H.W., "Recovery of function in osteoarthritic chondrocytes induced by $p16^{INK4a}$-specific siRNA in vitro", Rheumatology, vol. 43, pp. 555-568, (2004).
Fuijkschot, W.W. et al., "Prevention of age-induced $N(\epsilon)$-(carboxymethyl)lysine accumulation in the microvasculature", European Journal of Clinical Investigation, vol. 46, issue 4, pp. 334-341, (2016). (Abstract Only).
Rasheed, Z.A. et al., "Pathology of pancreatic stroma in PDAC", Pancreatic Cancer and Tumor Microenvironment, pp. 1-10, (2012).
Morton, J.P. et al., "Mutant p53 drives metastasis and overcomes growth arrest/senescence in pancreatic cancer", PNAS, vol. 107, No. 1, pp. 246-251, (2010).
Verzijl, N. et al., "AGEing and osteoarthritis: a different perspective", Current Opinion in Rheumatology, vol. 15, issue 5, pp. 616-622, (2003).
Frescas, D. et al., "Senescent cells expose and secrete an oxidized form of membrane-bound vimentin as revealed by a natural polyreactive antibody", PNAS, vol. 114, No. 9, pp. E1668-E1677, (2017).
Oren, M. et al., "Mutant p53 gain-of-function in cancer", Cold Spring Harbor Perspectives in Biology, vol. 2, pp. 1-15, (2010).
"Senescence promotes chemotherapy side effects and cancer relapse", Medical Xpress, pp. 1-4, found at https://m.medicalxpress.com/news/2017-01-senescence-chemotherapy-side-effects-cancer.html, (2017).
Oh, J. et al., "Local clearance of senescent cells attenuates the development of post-traumatic osteoarthritis and creates a pro-regenerative environment", Nature Medicine, vol. 23, No. 6, pp. 1-9, (2017).
Protocols for "Isolation of untouched human T cells from peripheral blood mononuclear cells (PBMC)", Thermo Fisher Scientific, pp. 1-4, found at www.thermofisher.com/us/en/home/references/protocols/proteins-expression-isolation-and-analysis/cell-separation-methods/human-cell-separation-protocols/isolation-of-untouched-human-t-cells-.html, printed on Aug. 17, 2017.
Henrich, C.J. et al., "Isolation and characterization of a glycopeptide from human senescent erythrocytes", Carbohydrate Research, vol. 120, pp. 55-66, (1983).
Yang, S. et al., "Impact of oxidative stress biomarkers and carboxymethyllysine (an advanced glycation end product) on prostate cancer: A prospective study", Clinical Genitourinary Cancer, vol. 13, No. 5, pp. 1-14, (2015).
Tsai, K.K.C. et al., "Low-dose radiation-induced senescent stromal fibroblasts render nearby breast cancer cells radioresistant", Radiation Research, vol. 172, pp. 306-313, (2009).
Nie, H et al., "Impaired glial glutamate uptake induces extrasynaptic glutamate spillover in the spinal sensory synapses of neuropathic rats", Journal of Neurophysiology, vol. 103, pp. 2570-2580, (2010).
Garcia-Matas, S. et al., "Dysfunction of astrocytes in senescence-accelerated mice SAMP8 reduces their neuroprotective capacity", Aging Cell, vol. 7, pp. 630-640, (2008).
Danysz, W. et al., "Alzheimer's disease, β-amyloid, glutamate, NMDA receptors and memantine-searching for the connections", British Journal of Pharmacology, vol. 167, pp. 324-352, (2012).
Blasko, I. et al., "Glial cells: Astrocytes and oligodendrocytes during normal brain aging", Encyclopedia of Neuroscience, pp. 743-747, (2009).
Leonard, B.W. et al., "Subventricular zone neural progenitors from rapid brain autopsies of elderly subjects with and without neurodegenerative disease", the Journal of Comparative Neurology, vol. 515, pp. 269-294, (2009).

(56) References Cited

OTHER PUBLICATIONS

Louveau, A. et al., "Structural and functional features of central nervous system lymphatic vessels", Nature, vol. 523, issue 7560, pp. 337-341, (2015).

Torgan, C., "Lymphatic vessels discovered in central nervous system", NIH Research Matters, pp. 1-4, found at www.nih.gov/news-events/nih-research-matters/lymphatic-vessels-discovered-central-nervous-system, Jun. 15, 2015.

Boskovitz, A. et al., "Monoclonal antibodies for brain tumour treatment", Expert Opinion on Biological Therapy, vol. 4, No. 9, pp. 1453-1471, (2004).

Takami, A. et al., "Treatment of primary central nervous system lymphoma with induction of complement-dependent cytotoxicity by intraventricular administration of autologous-serum-supplemented rituximab", Cancer Science, vol. 97, No. 1, pp. 80-83, (2006).

Biran, A. et al., "Senescent cells communicate via intercellular protein transfer", Genes & Development, vol. 29, pp. 791-802, (2015).

Golde, T.E. et al., "Proteinopathy-induced neuronal senescence: a hypothesis for brain failure in Alzheimer's and other neurodegenerative diseases", Alzheimer's Research & Therapy, vol. 1, No. 2, pp. 1-12, (2009).

Ouroboros, "Sweet madness: Sporadic prion disease and age-related changes in protein glycosylation", Research in the Biology of Aging, pp. 1-4, found at https://ouroboros.wordpress.com/2006/12/14/sweet-madness-sporadic-prion-disease-and-age-related-changes-in-protein-glycosylation/, (2006).

Xellbiogene, "Amyotrophic lateral sclerosis, immunotherapy is offering some hope", Xellbiogene.com, pp. 1-3, (2014).

Definition of "Complement system" printed from Wikipedia, the free encyclopedia on Aug. 4, 2015 found at http://en.wikipedia.org/wiki/Complement_system.

Definition of "Ventricular system" printed from Wikipedia, the free encyclopedia on Oct. 30, 2017 found at http://en.wikipedia.org/wiki/Ventricular_system.

Urushitani, M., "Future perspectives of immunotherapy against ALS", Rinsho Shinkeigaku, vol. 49, No. 11, pp. 818-820, (2009). (Abstract Only).

Cabezas, I.L. et al., "The role of glial cells in Alzheimer disease: potential therapeutic implications", Neurologia, vol. 29, No. 5, pp. 305-309, (2014).

Definition of "Prion" printed from Wikipedia, the free encyclopedia on Nov. 17, 2015 found at http://en.wikipedia.org/wiki/Prion.

"Prion Diseases", National Institute of Allergy and Infectious Diseases, pp. 1-2, found at www.niaid.nih.gov/diseases-conditions/prion-diseases, printed on Oct. 30, 2017.

"Alzheimer basics: Plaques and tangles", ALZ.org, pp. 1-2, found at www.alz.org/norcal/in_my_community_20545.asp, printed on Nov. 17, 2015.

Definition of "Lewy body" printed from Wikipedia, the free encyclopedia on Nov. 17, 2015 found at http://en.wikipedia.org/wiki/Lewy_body.

Definition of "Myocyte" printed from Wikipedia, the free encyclopedia on Nov. 17, 2015 found at http://en.wikipedia.org/wiki/Myocyte.

Definition of "Myosatellite cell" printed from Wikipedia, the free encyclopedia on Nov. 17, 2015 found at http://en.wikipedia.org/wiki/Myosatellite_cell.

Definition of "Microglia" printed from Wikipedia, the free encyclopedia on Oct. 30, 2017 found at http://en.wikipedia.org/wiki/Microglia.

Definition of "Astrocyte" printed from Wikipedia, the free encyclopedia on Oct. 30, 2017 found at http://en.wikipedia.org/wiki/Astrocyte.

Ouroboros, "A role for microglial senescence in Alzheimer's?", Research in the Biology of Aging, pp. 1-3, found at https://ouroboros.wordpress.com/?s=a+role+for+microglial, (2007).

Chen, K.S. et al., "Monoclonal antibody therapy for malignant glioma", Glioma: Immunotherapeutic Approaches, chapter 10, pp. 121-141, (2012).

Reardon, S., "Alzheimer's drug sneaks through blood-brain barrier", Nature News, pp. 1-4, (2014).

"Astrocytes as a novel target in Alzheimer's disease", Expertsvar, pp. 1-2, (2012).

Myslinski, N., "Alzheimer's disease and the blood-brain barrier", Today's Geriatric Medicine, vol. 7, No. 1, pp. 1-10, (2014).

Huffer-Saunders, J.A.L. et al., "Pathways towards an effective immunotherapy for Parkinson's disease", Expert Reviews in Neurotherapeutics, vol. 11, No. 12, pp. 1703-1715, (2011).

Definition of "Intrathecal administration" printed from Wikipedia, the free encyclopedia on Oct. 30, 2017 found at http://en.wikipedia.org/wiki/Intrathecal_administration.

"What is ALS?", ALSA.org, found at www.alsa.org/2015-non-responsive-pages/about-als/what-is-als.html, printed on Mar. 31, 2016.

Rouger, K. et al., "Systemic delivery of allogenic muscle stem cells induces long-term muscle repair and clinical efficacy in Duchenne muscular dystrophy dogs", the American Journal of Pathology, vol. 179, No. 5, pp. 2501-2518, (2011).

Anderson, J.L. et al., "Brain function in Duchenne muscular dystrophy", Brain, vol. 125, pp. 4-13, (2002).

Jarius, S. et al., "AQP4 antibodies in neuromyelitis optica: diagnostic and pathogenetic relevance", Nature Reviews, vol. 6, pp. 383-392, (2010).

Wesolowski, J. et al., "Single domain antibodies: promising experimental and therapeutic tools in infection and immunity", Medical Microbiology and Immunology, vol. 198, pp. 157-174, (2009).

Definition of "Antibody" printed from Wikipedia, the free encyclopedia on Sep. 21, 2015 found at http://en.wikipedia.org/wiki/Antibody.

Definition of "Antibody-dependent cell-mediated cytotoxicity" printed from Wikipedia, the free encyclopedia on Dec. 28, 2015 found at http://en.wikipedia.org/wiki/Antibody-dependent_cell-mediated_cytotoxicity.

Definition of "Blocking antibody" printed from Wikipedia, the free encyclopedia on Dec. 28, 2015 found at http://en.wikipedia.org/wiki/Blocking_antibody.

Definition of "Fc receptor" printed from Wikipedia, the free encyclopedia on Dec. 28, 2015 found at http://en.wikipedia.org/wiki/Fc_receptor.

Definition of "Fragment crystallizable region" printed from Wikipedia, the free encyclopedia on Dec. 28, 2015 found at http://en.wikipedia.org/wiki/Fragment_crystallizable_region.

Definition of "Neutralizing antibody" printed from Wikipedia, the free encyclopedia on Dec. 28, 2015 found at http://en.wikipedia.org/wiki/Neutralizing_antibody.

Company Information on "NantKwest", pp. 1-4, found at www.nantkwest.com, printed on Apr. 1, 2016.

Forbes, J.M. et al., "Below the radar: Advanced glycation end products that detour "around the side"", Clinical Biochemist Reviews, vol. 26, pp. 123-134, (2005).

Paul, W.E., "Fundamental immunology, third edition", Raven Press New York, chapter 9, pp. 292-295, (1993).

Rudikoff, S. et al., "Single amino acid substitution altering antigen-binding specificity", Proceedings of the National Academy of Science USA, vol. 79, pp. 1979-1983, (1982).

Wu, H. et al., "Humanization of a murine monoclonal antibody by simultaneous optimization of framework and CDR residues", Journal of Molecular Biology, vol. 294, pp. 151-162, (1999).

Golay, J. et al., "Mechanism of action of therapeutic monoclonal antibodies: Promises and pitfalls of in vitro and in vivo assays", Archives of Biochemistry and Biophysics, vol. 526, pp. 146-153, (2012).

Tang, S-S. et al., "Reaction of aortic lysyl oxidase with β-Aminopropionitrile", the Journal of Biological Chemistry, vol. 258, No. 7, pp. 4331-4338, (1983).

Saito, H. et al., "Regulation of a novel gene encoding a lysyl oxidase-related protein in cellular adhesion and senescence", the Journal of Biological Chemistry, vol. 272, No. 13, pp. 8157-8160, (1997).

(56) References Cited

OTHER PUBLICATIONS

Choi, Y-G. et al., "N$^\varepsilon$-carboxymethyl modification of lysine residues in pathogenic prion isoforms", Molecular Neurobiology, vol. 53, pp. 3102-3112, (2016).

Wendel, U. et al., "A novel monoclonal antibody targeting carboxymethyllysine, an advanced glycation end product in atherosclerosis and pancreatic cancer", PLoS One, vol. 13, No. 2, pp. 1-22, (2018).

Hsia, T-C. et al., "Carboxymethyllysine, an advanced glycation end-product, promotes the invasion and migration of lung cancer A549 cells", Clinical Medicine Research, vol. 6, No. 5, pp. 149-156, (2017).

Nowotny, K. et al., "Advanced glycation end products and oxidative stress in type 2 diabetes mellitus", Biomolecules, vol. 5, pp. 194-222, (2015).

Yun, M.H. et al., "Recurrent turnover of senescent cells during regeneration of a complex structure", eLIFE, elifesciences.org, pp. 1-16, (2015).

Barja, G., "Aging in vertebrates, and the effect of caloric restriction: a mitochondrial free radical production-DNA damage mechanism?", Biological Reviews, vol. 79, No. 2, pp. 235-251, (2004). Abstract Only.

Pamplona, R. et al., "Aging increases nepsilon-(carboxymethyl)lysine and caloric restriction decreases nepsilon-(carboxyethyl)lysine and nepsilon-(malondialdehyde)lysine in rat heart mitochondrial proteins", Free Radical Research, vol. 36, No. 1, pp. 47-54, (2002). Abstract Only.

Yun, M.H., "Cellular senescence in regeneration", the Node, pp. 1-8, found at http://thenode.biologists.com/cellular-senescence-in-regeneration/research/, Jun. 28, 2015.

Kasper, M. et al., "Age-related changes in cells and tissues due to advanced glycation end products (AGEs)", Archives of Gerontology and Geriatrics, vol. 32, issue 3, pp. 233-243, (2001).

Wang, Z. et al., "Advanced glycation end-product Nε-carboxymethyl-Lysine accelerates progression of atherosclerotic calcification in diabetes", Atherosclerosis, vol. 221, issue 2, pp. 387-396, (2012). Abstract Only.

Draber, P. et al., "Stability of monoclonal IgM antibodies freeze-dried in the presence of trehalose", Journal of Immunological Methods, vol. 181, issue 1, pp. 37-43, (1995).

Kesari, S. et al., "Pritumumab binding to glioma cells induces ADCC and inhibits tumor growth", Journal of Clinical Oncology, vol. 35, No. 15 Supplemental, e14004-e14004, (2017). Abstract Only.

Babic, I. et al., "Pritumumab, the first therapeutic antibody for glioma patients", Human Antibodies, vol. 26, No. 2, pp. 95-101, (2017). Abstract Only.

Riva, P. et al., "Treatment of intracranial human glioblastoma by direct intratumoral administration of $^{131}$I-labelled anti-tenascin monoclonal antibody BC-2", International Journal of Cancer, vol. 51, No. 1, pp. 7-13, (1992). Abstract Only.

Ruster, M. et al., "Detection of elevated N$^\varepsilon$-carboxymethyllysine levels in muscular tissue and in serum of patients with fibromyalgia", Scandinavian Journal of Rheumatology, vol. 34, issue 6, pp. 460-463, (2005). Abstract Only.

Niwa, H. et al., "Accelerated formation of N$^\varepsilon$-(carboxymethyl) lysine, an advanced glycation end product, by glyoxal and 3-deoxyglucosone in cultured rat sensory neurons", Biochemical and Biophysical Research Communications, vol. 248, issue 1, pp. 93-97, (1998). Abstract Only.

Daly, C. et al., "Monocyte chemoattractant protein-1 (CCL2) in inflammatory disease and adaptive immunity: Therapeutic opportunities and controversies", Microcirculation, vol. 10, pp. 247-257, (2003).

Lee, S.T. et al., "Decreased number and function of endothelial progenitor cells in patients with migraine", Neurology, vol. 70, No. 17, pp. 1510-1517, (2008). Abstract Only.

Brown, J.N. et al., "Class effect of erythropoietin therapy on hemoglobin $A_{1c}$ in a patient with diabetes mellitus and chronic kidney disease not undergoing hemodialysis", Pharmacotherapy, the Journal of Human Pharmacology and Drug Therapy, vol. 29, No. 4, pp. 468-472, (2009). Abstract Only.

Liu, J. et al., "Accelerated senescence of renal tubular epithelial cells is associated with disease progression of patients with immunoglobulin a (IgA) nephropathy", Translational Research, vol. 159, issue 6, pp. 454-463, (2012). Abstract Only.

Khaw, K-T. et al., "Association of hemoglobin $A_{1c}$ with cardiovascular disease and mortality in adults: The European prospective investigation into cancer in Norfolk", Annals of Internal Medicine, vol. 141, pp. 413-420, (2004).

Kohnert, K.D. et al., "Destruction of pancreatic beta cells in rats by complete Freund's adjuvant combined with non-diabetogenic doses of streptozotocin", Diabetes Research, vol. 5, No. 1, pp. 1-11, (1987). Abstract Only.

Staud, R., "Fibromyalgia pain: do we know the source?", Current Opinion in Rheumatology, vol. 16, issue 2, pp. 157-163, (2004). Abstract Only.

Fleurence, J. et al., "Targeting and killing glioblastoma with monoclonal antibody to O-acetyl GD2 ganglioside", Oncotarget, vol. 7, No. 27, pp. 41172-41185, (2016).

Velarde, M.C. et al., "Senescent cells and their secretory phenotype as targets for cancer therapy", Interdisciplinary Topics in Gerontology, vol. 38, pp. 17-27, (2013).

Wang, Z. et al., "CML/RAGE signal induces calcification cascade in diabetes", Diabetology & Metabolic Syndrome, vol. 8, No. 83, pp. 1-12, (2016).

Freise, A.C. et al., "In vivo imaging with antibodies and engineered fragments", Molecular Immunology, vol. 67, issue 2, pp. 142-152, (2015).

Pavlides, S. et al., "The reverse Warburg effect: Aerobic glycolysis in cancer associated fibroblasts and the tumor stroma", Cell Cycle, vol. 8, No. 23, pp. 3984-4001, (2009).

Dunn, G.P. et al., "Principles of immunology and its nuances in the central nervous system", Neuro-Oncology, vol. 17, pp. vii3-vii8, (2015).

Rettig, M.P. et al., "Evaluation of biochemical changes during in vivo erythrocyte senescence in the dog", Blood, vol. 93, No. 1, pp. 376-384, (1999).

Baraibar, M.A. et al., "Proteomic quantification and identification of carbonylated proteins upon oxidative stress and during cellular aging", Journal of Proteomics, vol. 92, pp. 63-70, (2013). Abstract Only.

Chaudhuri, J. et al., "A Caenorhabditis elegans model elucidates a conserved role for TRPA1-Nrf signaling in reactive α-dicarbonyl detoxification", Current Biology, vol. 26, pp. 3014-3025, (2016).

Saleh, T. et al., "Reversibility of chemotherapy-induced senescence is independent of autophagy and a potential model for tumor dormancy and cancer recurrence", bioRxiv, pp. 1-29, 5 figures, (2017).

Hubert, P. et al., "Antibody-dependent cell cytotoxicity in monoclonal antibody-mediated tumor immunotherapy", OncoImmunology, vol. 1, issue 1, pp. 103-105, (2012).

Ouchi, R. et al., "Senescence from glioma stem cell differentiation promotes tumor growth", Biochemical and Biophysical Research Communications, vol. 470, No. 2, pp. 275-281, (2016).

Evans, A. et al., "Differentiating benign from malignant solid breast masses: value of shear wave elastography according to lesion stiffness combined with greyscale ultrasound according to BI-RADS classification", British Journal of Cancer, vol. 107, pp. 224-229, (2012).

Walen, K.H., "Normal human cell conversion to 3-D cancer-like growth: Genome damage, endopolyploidy, senescence escape, and cell polarity change/loss", Journal of Cancer Therapy, vol. 2, pp. 181-189, (2011).

Virella, G. et al., "Development of capture assays for different modifications of human low-density lipoprotein", Clinical and Diagnostic Laboratory Immunology, vol. 12, No. 1, pp. 68-75, (2005).

Moghaddam, A.E. et al., "Reactive carbonyls are a major Th2-inducing damage-associated molecular pattern generated by oxidative stress", the Journal of Immunology, vol. 187, pp. 1626-1633, (2011).

(56) References Cited

OTHER PUBLICATIONS

Kuilman, T. et al., "The essence of senescence", Genes & Development, vol. 24, pp. 2463-2479, (2010).
James, E.L. et al., "Senescent human fibroblasts show increased glycolysis and redox homeostasis with extracellular metabolomes that overlap with those of irreparable DNA damage, aging, and disease", Journal of Proteome Research, vol. 14, pp. 1854-1871, (2015).
Hein, G. et al., "Are advanced glycation end-product-modified proteins of pathogenetic importance in fibromyalgia?" Rheumatology, vol. 41, pp. 1163-1167, (2002).
Beausejour, C.M. et al., "Reversal of human cellular senescence: roles of the p53 and p16 pathways", the EMBO Journal, vol. 22, No. 16, pp. 4212-4222, (2003).
Simpson, R.J., "Aging, persistent viral infections, and immunosenescence: Can exercise "make space"?", Exercise and Sport Sciences Reviews, vol. 39, No. 1, pp. 23-33, (2011).
Gudkov, A., "Andrei Gudkov taped an expanded presentation of the slides he presented at 2017 Biology of Aging conference at Scripps, Florida, Jan. 22-27", Everon Biosciences, found at everonbio.com/Andrei-gudkov-taped-an-expanded-presentation-of-the-slides-he-presented-at-2017-biology-of-aging-conference-at-scripps-fiorida-22-27-january, 2 pages, Mar. 21, 2017. Abstract Only.
Radoi, V. et al., "Advanced glycation end products in diabetes mellitus: Mechanism of action and focused treatment", Proceedings of the Romanian Academy, Series B, vol. 1, pp. 9-19, (2012).
Sieben, C.J. et al., "Two-step senescence-focused cancer therapies", Trends in Cell Biology, pp. 1-15, (2018).
Gaens, K.H.J. et al., "$N^\epsilon$-(carboxymethyl)lysine-receptor for advanced glycation end product axis is a key modulator of obesity-induced dysregulation of adipokine expression and insulin resistance", Arteriosclerosis, Thrombosis, and Vascular Biology, vol. 34, issue 6, pp. 1199-1208, pp. s1-s9, (2014).
Semba, R.D. et al., "Relationship of an advanced glycation end product, plasma carboxymethyl-lysine, with slow walking speed in older adults: the inCHIANTI study", European Journal of Applied Physiology, vol. 108, No. 1, pp. 191-195, (2010).
Wu, J. et al., "Sonoporation, anti-cancer drug and antibody delivery using ultrasound", Ultrasonics, vol. 44, supplement, pp. e21-e25, (2006). Abstract Only.
Meerwaldt, R. et al., "Skin autofluorescence is a strong predictor of cardiac mortality in diabetes", Diabetes Care, vol. 30, No. 1, pp. 107-112, (2007).
Nagai, R. et al., "Antibody-based detection of advanced glycation end-products: promises vs. limitations", Glycoconjugate Journal, vol. 33, No. 4, pp. 545-552, (2016).
Schmidt, A.M. et al., "The biology of the receptor for advanced glycation end products and its ligands", Biochimica et Biophysica Acta, vol. 1498, pp. 99-111, (2000).
Berens, M.E. et al., "". . . those left behind." Biology and oncology of invasive glioma cells", Neoplasia, vol. 1, No. 3, pp. 208-219, (1999).
Hansen, K. et al., "Microneedle enabled intradermal delivery of biologics", 3M Drug Delivery Systems, 1 page, printed on Jul. 25, 2018.
Ikeda, K. et al., "Immunochemical approaches to AGE-structures: characterization of anti-AGE antibodies", Journal of Immunological Methods, vol. 215, No. 1-2, pp. 95-104, (1998).
De Vriese, A.S. et al., "Inhibition of the interaction of AGE-RAGE prevents hyperglycemia-induced fibrosis of the peritoneal membrane", Journal of the American Society of Nephrology, vol. 14, pp. 2109-2118, (2003).
Ott, C. et al., "Role of advanced glycation end products in cellular signaling", Redox Biology, vol. 2, pp. 411-429, (2014).
International Search Report and Written Opinion dated Aug. 7, 2018 for PCT application No. PCT/US2018/027653.
International Search Report and Written Opinion dated Sep. 10, 2018 for PCT application No. PCT/US2018/030931.
Edwards, B.M. et al., "The remarkable flexibility of the human antibody repertoire; Isolation of over one thousand different antibodies to a single protein, BLyS", the Journal of Molecular Biology, vol. 334, pp. 103-118, (2003).
Lloyd, C. et al., "Modelling the human immune response: performance of a $10^{11}$ human antibody repertoire against a broad panel of therapeutically relevant antigens", Protein Engineering, Design & Selection, vol. 22, No. 3, pp. 159-168, (2009).
Ansari, N.A. et al., "Glycated lysine residues: A marker for non-enzymatic protein glycation in age-related diseases", Disease Markers, vol. 30, pp. 317-324, (2011).
Blagosklonny, M.V. et al., "Cancer and aging", Cell Cycle, vol. 7, No. 17, pp. 2615-2618, (2008).
Chow, H-M. et al., "Senescent neurons in the alzheimer's brain kill nearby healthy neurons by blocking their WNT lifeline: The continuing saga of the zombie apocalypse", Alzheimer's & Dementia, vol. 12, No. 7(S), p. P658, (2016).
Dvorakova, E. et al., "Development of monoclonal antibodies specific for glycated prion protein", Journal of Toxicology and Environmental Health, Part A, vol. 74, pp. 1469-1475, (2011).
Search Results for "Carboxy Methyl Lysine Anitbody", 7 pages, antibodies-online.com, (2018).
Awwad, S. et al., "Overview of antibody drug delivery", Pharmaceutics, vol. 10, No. 83, pp. 1-24, (2018).
Farr, J.N. et al., "Targeting cellular senescence prevents age-related bone loss in mice", Nature Medicine, vol. 23, No. 9, pp. 1072-1079, (2017).
Hoenicke, L. et al., "Immune surveillance of senescent cells—biological significance in cancer- and non-cancer pathologies", Carcinogenesis, vol. 33, No. 6, pp. 1123-1126, (2012).
Kemmler, W. et al., "Prevalence of sarcopenia in Germany and the corresponding effect of osteoarthritis in females 70 years and older living in the community: results of the FORMoSA study", Clinical Interventions in Aging, vol. 10, pp. 1565-1573, (2015).
Myrianthopoulos, V. et al., "Senescence and senotherapeutics: a new field in cancer therapy", Pharmacology & Therapeutics, vol. 193, pp. 31-49, (2019).
Salahuddin, P. et al., "The role of advanced glycation end products in various types of neurodegenerative disease: A therapeutic approach", Cellular & Molecular Biology Letters, vol. 19, pp. 407-437, (2014).
Schosserer, M. et al., "The dual role of cellular senescence in developing tumors and their response to cancer therapy", Frontiers in Oncology, vol. 7, article 278, pp. 1-13, (2017).
Bussian, T.J. et al., "Clearance of senescent glial cells prevents tau-dependent pathology and cognitive decline", Nature Letters, vol. 562, pp. 578-582, (2018).
Penney, J. et al., "Senescence mediates neurodegeneration", Nature, vol. 562, pp. 503-504, (2018).
Trivedi, P.M. et al., "Repurposed JAK1/JAK2 inhibitor reverses established autoimmune insulitis in NOD mice", Diabetes, vol. 66, p. 1650-1660, (2017).
Wang, C. et al., "DNA damage response and cellular senescence in tissues of aging mice", Aging Cell, vol. 8, pp. 311-323, (2009).
Iizuka, K. et al., "Dasatinib improves insulin sensitivity and affects lipid metabolism in a patient with chronic myeloid leukaemia", BMJ Case Rep, pp. 1-3, (2016).
Jeon, O.H. et al., "Local clearance of senescent cells attenuates the development of posttraumatic osteoarthritis and creates a pro-regenerative environment", Nature Medicine, vol. 23, pp. 775-781, (2017). Abstract Only.
Duke Health News & Media, "Duke team finds missing immune cells that could fight lethal brain tumors", Duke University School of Medicine, pp. 1-5, (2018).
Apple, S., "An old idea, revived: Starve cancer to death", NYTimes.com, pp. 1-15, (2016).
Dock, J.N. et al., "Role of CD8 T cell replicative senescence in human aging and in HIV-mediated immunosenescence", Aging and Disease, vol. 2, No. 5, pp. 382-397, (2011).
Rayavarapu, S. et al., "Idiopathic inflammatory myopathies: pathogenic mechanisms of muscle weakness", Skeletal Muscle, vol. 3, No. 13, pp. 1-13, (2013).

(56) References Cited

OTHER PUBLICATIONS

Kudryashova, E. et al., "Satellite cell senescence underlies myopathy in a mouse model of limb-girdle muscular dystrophy 2H", the Journal of Clinical Investigation, vol. 122, No. 5, pp. 1764-1776, (2012).
Ratelade, J. et al., "Neuromyelitis optica IgG and natural killer cells produce NMO lesions in mice without myelin loss", Acta Neuropathologica, vol. 123, issue 6, pp. 861-872, (2012).
Vincent, T. et al., "Functional consequences of neuromyelitis optica-IgG astrocyte interactions on blood-brain barrier permeability and granulocyte recruitment", the Journal of Immunology, vol. 181, pp. 5730-5737, (2008).
Baarine, M. et al., "ABCD1 deletion-induced mitochondrial dysfunction is corrected by SAHA: implication for adrenoleukodystrophy", Journal of Neurochemistry, vol. 133, pp. 380-396, (2015).
Durieu, I. et al., "Subepithelial fibrosis and degradation of the bronchial extracellular matrix in cystic fibrosis", American Journal of Respiratory and Critical Care Medicine, vol. 158, No. 2, pp. 580-588, (1998).
Shapiro, B.L. et al., "Premature senescence in cultured skin fibroblasts from subjects with cystic fibrosis", Science, vol. 203, issue 4386, pp. 1251-1253, (1979). Abstract Only.
Fischer, B.M. et al., "Increased expression of senescence markers in cystic fibrosis airways", American Journal of Physiology Lung Cellular and Molecular Physiology, vol. 304, No. 6, pp. L394-L400, (2013).
Thom, M. et al., "An investigation of the expression of $G_1$-phase cell cycle proteins in focal cortical dysplasia type IIB", Journal of Neuropathology and Experimental Neurology, vol. 66, No. 11, pp. 1045-1055, (2007).
Valdivieso, A.G. et al., "CFTR activity and mitochondrial function", Redox Biology, vol. 1, pp. 190-202, (2013).
Chilosi, M. et al., "Premature lung aging and cellular senescence in the pathogenesis of idiopathic pulmonary fibrosis and COPD/emphysema", Translational Research, vol. 162, issue 3, pp. 156-173, (2013). Abstract Only.
Ribeiro, C.M.P., "The role of intracellular calcium signals in inflammatory responses of polarized cystic fibrosis human airway epithelia", Drugs in R&D, vol. 7, issue 1, pp. 17-31, (2006). Abstract Only.
Velisek L. et al., "Aging: effects of aging on seizures and epilepsy", Encyclopedia of Basic Epilepsy Research, pp. 37-40, (2009). Abstract Only.
Muller, S. et al., "Analysis of senescence markers in rodent pancreatic stellate cells", the Pancreapedia, pp. 1-8, (2013).
Lim, M., "Acute immunology, temporal lobe epilepsy and other disorders", YoungEpilepsy.Org, pp. 1-70, found at http://youngepilepsy.org.uk/dmdocuments/MIND-THE-GAP2015_Ming%20Lim.pdf, (2015).
Definition of "Cachexia" printed from Wikipedia, the free encyclopedia on Dec. 28, 2015 found at http://en.wikipedia.org/wiki/Cachexia.
Lok, C., "The last illness, researchers are gaining insight into the causes of Cachexia—a devastating form of muscle wasting that is often the final stage of cancer and other diseases", Nature, vol. 528, pp. 182-183, (2015).
da Rocha, O.M. et al., "Sarcopenia in rheumatoid cachexia: definition, mechanisms, clinical consequences and potential therapies", Revista Brasileira de Reumatologia, vol. 49, No. 3, pp. 294-301, (2009).
Tisdale, M.J., "Biology of Cachexia", Journal of the National Cancer Institute, vol. 89, No. 23, pp. 1763-1773, (1997).
Romanick, M. et al., "Murine models of atrophy, cachexia, and sarcopenia in skeletal muscle", Biochimica et Biophysica Acta—Molecular Basis of Disease, vol. 1832, issue 9, pp. 1410-1420, (2013).
Ali, S. et al., "Sarcopenia, cachexia and aging: Diagnosis, mechanisms and therapeutic options", Gerontology, vol. 60, No. 4, pp. 294-305, (2014).

Angelini, P.D. et al., "Constitutive HER2 signaling promotes breast cancer metastasis through cellular senescence", Cancer Research, vol. 73, No. 1, pp. 450-458, (2013).
Arai, Y. et al., "Inflammation, but not telomere length, predicts successful ageing at extreme old age: A longitudinal study of semi-supercentenarians", EBioMedicine, vol. 2, pp. 1549-1558, (2015).
Bedard, N. et al., "Inactivation of the ubiquitin-specific protease 19 deubiquitinating enzyme protects against muscle wasting", the FASEB Journal, vol. 29, No. 9, pp. 3889-3898, (2016).
Figueroa-Clarevega, A. et al., "Malignant drosophila tumors interrupt insulin signaling to induce cachexia-like wasting", Developmental Cell, vol. 33, pp. 47-55, (2015).
Giacconi, R. et al., "Cellular senescence and inflammatory burden as determinants of mortality in elderly people until the extreme old age", EBioMedicine, vol. 2, pp. 1316-1317, (2015).
Jin, H. et al., "Protein modifications as potential biomarkers in breast cancer", Biomarker Insights, vol. 4, pp. 191-200, (2009).
Lee, S-J. et al., "Treating cancer cachexia to treat cancer", Skeletal Muscle, vol. 1, No. 2, pp. 1-5, (2011).
Mohamed, M.M. et al., "Human monocytes augment invasiveness and proteolytic activity of inflammatory breast cancer", Biological Chemistry, vol. 389, No. 8, pp. 1117-1121, (2008).
Pare, R. et al., "The significance of the senescence pathway in breast cancer progression", Journal of Clinical Pathology, vol. 66, pp. 491-495, (2013). Abstract Only.
Pinto, N.I. et al., "Cancer as a proinflammatory environment: Metastasis and cachexia", Mediators of Inflammation, vol. 2015, pp. 1-13, (2015).
Tesarova, P. et al., "Carbonyl and oxidative stress in patients with breast cancer—is there a relation to the stage of the disease?", Neoplasma, vol. 54, No. 3, pp. 219-224, (2007).
Tseng, Y-C., et al., "Preclinical investigation of the novel histone deacetylase inhibitor AR-42 in the treatment of cancer-induced cachexia", Journal of the National Cancer Institute, vol. 107, No. 12, pp. 1-14, (2015).
Wang, S. et al., "Characterization of IGFBP-3, PAI-1 and SPARC mRNA expression in senescent fibroblasts", Mechanisms of Ageing and Development, vol. 92, issues 2-3, pp. 121-132, (1996). Abstract Only.
Yang, S. et al., "Impact of oxidative stress biomarkers and carboxymethyllysine (an advanced glycation end product) on prostate cancer: A prospective study", Clinical Genitourinary Cancer, vol. 13, issue 6, pp. e347-e351, (2015).
"Global Arthritis Research Network: $4^{th}$ World Congress on Arthritis in Montreal", Arthritis Research & Therapy, vol. 6, supplement 3, meeting abstracts, pp. S1-S41, Sep. 20-22, 2004.
Miller, R.E. et al., "Osteoarthritis joint pain: The cytokine connection", Cytokine, vol. 70, No. 2, pp. 185-193, (2014).
LifeExtension, "Chronic Pain", Lifeextension.com, pp. 1-18, found at www.lifeextension.com/protocols/health-concerns/chronic-pain/page-03, (2016).
Rush University Medical Center, "Scientists home in on cause of osteoarthritis pain". Science Daily, found at www.sciencedaily.com/releases/2012/12/121227173053.htm, pp. 1-4, (2012).
Kidd, B.L. et al., "Mechanisms of inflammatory pain", British Journal of Anesthesia, vol. 87, No. 1, pp. 3-11, (2001).
Price, J.S. et al., "The role of chondrocyte senescence in osteoarthritis", Aging Cell, vol. 1, pp. 57-65, (2002).
Morales, T.I., "Chondrocyte moves: clever strategies?", OsteoArthritis and Cartilage, vol. 15, pp. 861-871, (2007).
Martin, J.A. et al., "Effects of oxidative damage and telomerase activity on human articular cartilage chondrocyte senescence", Journal of Gerontology: Biological Sciences, vol. 59A, No. 4, pp. 324-337, (2004).
Ang, D.C. et al., "MCP-1 and IL-8 as pain biomarkers in fibromyalgia: A pilot study", Pain Medicine, vol. 12, pp. 1154-1161, (2011).
Burton, D.G.A. et al., "Microarray analysis of senescent vascular smooth muscle cells: A link to atherosclerosis and vascular calcification", Experimental Gerontology, vol. 44, issue 10, pp. 659-665, (2009).

(56) References Cited

OTHER PUBLICATIONS

Konttinen, Y.T. et al., "Chondrocyte-mediated collagenolysis correlates with cartilage destruction grades in osteoarthritis", Clinical and Experimental Rheumatology, vol. 23, pp. 19-26, (2005).
"Low back pain", U.S. Department of Health and Human Services, Public Health Service National Institutes of Health, 1-28, (2014).
Bicer, F. "CCL2 (MCP-1) mediates chronic pelvic pain through mast cells in experimental autoimmune cystitis", ETD Archive, pp. 1-120, (2012).
Loeser, R.F. "Aging and osteoarthritis: The role of chondrocyte senescence and aging changes in the cartilage matrix", Osteoarthritis and Cartilage, vol. 17, No. 8, pp. 971-979, (2009).
Zhou, H-W. et al., "Expressions of p16INK4a in healthy and osteoarthritic human articular cartilage and difference analysis", Research Gate, pp. 2148-2149, found at www.researchgate.net/publication/290275008_Expressions_of_p16INK4a_in_healthy_and_osteoarthritic_human_articular_cartilage_and_difference_analysis, (2004). Abstract Only.
Martin, J.A. et al., "Post-traumatic osteoarthritis: the role of accelerated chondrocyte senescence", Biorheology, vol. 41, pp. 479-491, (2004).
Martin, J.A. et al., "Human chondrocyte senescence and osteoarthritis", Biorheology, vol. 39, No. 1,2, pp. 145-152, (2002). Abstract Only.
Forliti, M., "Mayo clinic researchers link senescent cells to most common form of arthritis", Mayo Clinic, pp. 1-2, found at www.eurekalert.org/pub_releases/2016-08/mc-mcr081016.php, (2016).
Roubenoff, R., "Sarcopenic obesity: Does muscle loss cause fat gain? Lessons from Rheumatoid arthritis and osteoarthritis", Annals of the New York Academy of Sciences, vol. 904, pp. 553-557, (2000). Abstract Only.
De Ceuninck, F. et al., "Bearing arms against osteoarthritis and sarcopenia: When cartilage and skeletal muscle find common interest in talking together", Drug Discovery Today, vol. 19, issue 3, pp. 305-311, (2014). Abstract Only.
Chatterjea, D. "Mast cells and pain", Mastcell Basophil, pp. 1-5, found at www.mastcell-basophil.net/wiki/wiki-start/mast-cells-and-pain/, (2013).
Bach, B. "New drug promises relief for inflammatory pain, scientists say", News Center, Stanford Medicine PASiN, found at med.stanford.edu/news/all-news/2014/08/new-drug-promises-relief-for-inflammatory-pain--scientists-say.html, 3 pages, (2014).
Daly, C. et al., "Monocyte chemoattractant protein-1 (CCL2) in inflammatory disease and adaptive immunity: Therapeutic opportunities and controversies", Microcirculation, vol. 10, issue 3-4, pp. 247-257, (2003).
"MMP13 gene", NIH U.S. National Library of Medicine, found at ghr.nlm.nih.gov/gene/MMP13, 4 pages, (2016).
Hayami, T. et al., "MMP-1 (Collagenase-1) and MMP-13 (Collagenase-3) differentially regulate markers of osteoblastic differentiation in osteogenic cells", Matrix Biology, vol. 27, issue 8, pp. 682-692, (2008).
Attur, M.G. et al., "Autocrine production of IL-1 beta by human osteoarthritis-affected cartilage and differential regulation of endogenous nitric oxide, IL-6, prostaglandin E2, and IL-8", Proceedings of the Association of American Physicians, vol. 110, No. 1, pp. 65-72, (1998). Abstract Only.
Xu, Y-K. et al., "The role of MCP-I-CCR2 ligand-receptor axis in chondrocyte degradation and disease progress in knee osteoarthritis", Biological Research, vol. 48, No. 64, pp. 1-8, (2015).
Goldring, M.B., "The role of the chondrocyte in osteoarthritis", Arthritis & Rheumatism, vol. 43, No. 9, pp. 1916-1926, (2000).
Mobasheri, A. et al., "Chondrocyte and mesenchymal stem cell-based therapies for cartilage repair in osteoarthritis and related orthopaedic conditions", Maturitas, vol. 78, pp. 188-198, (2014).
"What are chondrocytes?", wiseGeek, found at www.wisegeek.org/what-are-chondrocytes.htm, 1 page, printed on Nov. 29, 2016.
Woolf, A.D. et al., "Burden of major musculoskeletal conditions", Bulletin of the World Health Organization, vol. 81, No. 9, pp. 646-656, (2003).

Pereira, D. et al., "The effect of osteoarthritis definition on prevalence and incidence estimates: a systematic review", Osteoarthritis and Cartilage, vol. 19, pp. 1270-1285, (2011).
Martin, J.A. et al., "Aging, articular cartilage chondrocyte senescence and osteoarthritis", Biogerontology, vol. 3, pp. 257-264, (2002).
"What is osteoarthritis?", NIH National Institute of Arthritis and Musculoskeletal and Skin Diseases, pp. 1-4, (2014).
Definition of "Osteoarthritis" printed from Wikipedia, the free encyclopedia, found at en.wikipedia.org/wiki/Osteoarthritis, Dec. 13, 2016.
"At a glance 2016, Arthritis, Improving the quality of life for people with arthritis", National Center for Chronic Disease Prevention and Health Promotion, pp. 1-4, (2016).
"IASP Taxonomy", International Association for the Study of Pain, found at www.iasp-pain.org/Taxonomy, pp. 1-9, (2014).
"Pain: Hope through research", National Institute of Neurological Disorders and Stroke, National Institutes of Health, pp. 1-46, (2014).
Definition of "Allodynia" printed from Wikipedia, the free encyclopedia, found at en.wikipedia.org/wiki/Allodynia, Dec. 13, 2016.
Quadros, A.U. et al., "Dynamic weight bearing is an efficient and predictable method for evaluation of arthritic nociception and its pathophysiological mechanisms in mice", Nature, Scientific Reports, pp. 1-11, (2015).
Leung, L. et al., "TNF-α and neuropathic pain—a review", Journal of Neuroinflammation, vol. 7, No. 27, pp. 1-11, (2010).
Schafers, M. et al., "Tumor necrosis factor-α induces mechanical allodynia after spinal nerve ligation by activation of p38 MAPK in primary sensory neurons", the Journal of Neuroscience, vol. 23, No. 7, pp. 2517-2521, (2003).
Sun, J.L. et al., "CX3CL1/CX3CR1 regulates nerve injury-induced pain hypersensitivity through the ERK5 signaling pathway", Journal of Neuroscience Research, vol. 91, No. 4, pp. 545-553, (2013). Abstract Only.
Watkins, L.R. et al., "Mechanisms of tumor necrosis factor-α (TNF-α) hyperalgesia", Brain Research, vol. 692, issues 1-2, pp. 244-250, (1995). Abstract Only.
American Diabetes Association, "Diagnosis and classification of diabetes mellitus", Diabetes Care, vol. 31, supp. 1, pp. S55-S60, (2008).
"Global report on diabetes", World Health Organization, pp. 1-88, (2016).
"National diabetes statistics report, 2017: Estimates of diabetes and its burden in the United States", U.S. Department of Health and Human Services, Centers for Disease Control and Prevention, pp. 1-20, (2017).
O'Brien, P.D. et al., "Mouse models of diabetic neuropathy", Institute for Laboratory Animal Research Journal, vol. 54, No. 3, pp. 259-272, (2014).
O'Brien, P.D. et al., "BTBR ob/ob mice as a novel diabetic neuropathy model: Neurological characterization and gene expression analyses", Neurobiology of Disease, vol. 73, pp. 348-355, (2015).
Alpers, C.E. et al., "Mouse models of diabetic nephropathy", Current Opinion in Nephrology and Hypertension, vol. 20, No. 3, pp. 278-284, (2011).
Hudkins, K.L. et al., "BTBR ob/ob mutant mice model progressive diabetic nephropathy", Journal of the American Society of Nephrology, vol. 21, pp. 1533-1542, (2010).
O'Brien, K.D. et al., "Divergent effects of vasodilators on cardiac hypertrophy and inflammation in a murine model of diabetic cardiomyopathy", Journal of the American College of Cardiology, vol. 57, issue 17, p. e193, (2011). Abstract Only.
Lee, J-T. et al., "Macrophage metalloelastase (MMP12) regulates adipose tissue expansion, insulin sensitivity, and expression of inducible nitric oxide synthase", Endocrinology, vol. 155, No. 9, pp. 3409-3420, (2014).
Xu, X. et al., "A glimpse of matrix metalloproteinases in diabetic nephropathy", Current Medicinal Chemistry, vol. 21, No. 28, pp. 3244-3260, (2014).

(56) References Cited

OTHER PUBLICATIONS

Tsioufis, C. et al., "The role of matrix metalloproteinases in diabetes mellitus", Current Topics in Medicinal Chemistry, vol. 12, No. 10, pp. 1159-1165, (2012). Abstract Only.

Pechhold, K. et al., "Blood glucose levels regulate pancreatic β-cell proliferation during experimentally-induced and spontaneous autoimmune diabetes in mice", PLoS One, vol. 4, No. 3, pp. e4827, (2009).

Oh, K-J. et al., "Metabolic adaptation in obesity and type II diabetes: myokines, adipokines and hepatokines", International Journal of Molecular Sciences, vol. 18, No. 1, article 8, pp. 1-31, (2017).

Micov, A. et al., "Levetiracetam synergises with common analgesics in producing antinociception in a mouse model of painful diabetic neuropathy", Pharmacological Research, vol. 97, pp. 131-142, (2015). Abstract Only.

Feldman, E., "Tail flick assay", Animal Models of Diabetic Complications Consortium, pp. 1-3, (2004).

Bratwur, W., "ABT 263 was formulated in 10 ethano", found at www.selleckchem.com/blog/ABT-263-was-formulated-in-10-ethano. html, (2013). Abstract Only.

"Beta cell dysfunction", Diabetes and the Environment, found at www.diabetesandenvironment.org/home/mech/betacells, pp. 1-7, printed on Feb. 27, 2019.

Edelman, D., "Understanding beta cell exhaustion in Type 2 diabetics", Diabetes Daily, found at www.diabetesdaily.com/blog/2008/06/podcast-understanding-beta-cell-exhaustion-in-type-2-diabetics, pp. 1-6, (2008).

Cao, Y. et al., "Mechanisms of endothelial to mesenchymal transition in the retina in diabetes", Investigative Ophthalmology & Visual Science, vol. 55, pp. 7321-7331, (2014).

Palmer, A.K. et al., "Cellular senescence in Type 2 diabetes: a therapeutic opportunity", Diabetes, vol. 64, pp. 2289-2298, (2015).

Cummings, B.P. et al., "Maternal ileal interposition surgery confers metabolic improvements to offspring independent of effects on maternal body weight in UCD-T2DM rats", Obesity Surgery, vol. 23, No. 12, pp. 2042-2049, (2013).

Cummings, B.P. et al., "Development and characterization of a novel rat model of type 2 diabetes mellitus: the UC Davis type 2 diabetes mellitus UCD-T2DM rat", American Journal of Physiology Regulatory, Integrative and Comparative Physiology, vol. 295, pp. R1782-R1793, (2008).

Cummings, B.P. et al., "Bile-acid-mediated decrease in endoplasmic reticulum stress: a potential contributor to the metabolic benefits of ileal interposition surgery in UCD-T2DM rats", Disease Models & Mechanisms, vol. 6, No. 2, pp. 443-456, (2013).

Cummings, B.P. et al., "Vertical sleeve gastrectomy improves glucose and lipid metabolism and delays diabetes onset in the UCD-T2DM rats", Endocrinology, vol. 153, No. 8, pp. 3620-3632, (2012).

Cummings, B.P. et al., "Heal interposition surgery improves glucose and lipid metabolism and delays diabetes onset in the UCD-T2DM rat", Gastroenterology, vol. 138, pp. 2437-2446, (2010).

American Diabetes Association, "Standards of medical care in diabetes—2016 abridged for primary care providers", Diabetes, vol. 34, No. 1, pp. 3-21, (2016).

Definition of "Methylglyoxal" printed from Wikipedia, the free encyclopedia, found at en.wikipedia.org/wiki/Methylglyoxal, Jun. 5, 2017.

Boesten, D.M.P.H.J. et al., "Effect of Nε-carboxymethyllysine on oxidative stress and the glutathione system in beta cells", Toxicology Reports, vol. 1, pp. 973-980, (2014).

Molla, B. et al., "Two different pathogenic mechanisms, dying-back axonal neuropathy and pancreatic senescence, are present in the YG8R mouse model of Friedreich ataxia", Disease Models & Mechanisms, vol. 9, pp. 647-657, (2016).

Kender, Z. et al., "Effect of metformin on methylglyoxal metabolism in patients with type 2 diabetes", Experimental and Clinical Endocrinology & Diabetes, vol. 122, No. 5, pp. 316-319, (2014). Abstract Only.

Ehrenmann, F. et al., "IMGT/3Dstructure-DB and IMGT/DomainGapAlign: a database and a tool for immunoglobulins or antibodies, T cell receptors, MHC, IgSF and MhcSF", Nucleic Acids Research, vol. 38, pp. D301-D307, (2010).

Glover, A., "Of mice and men", European Biophamaceutical Review, pp. 30-34, (2016).

"The basic guide to magnetic bead cell separation", Sepmag.eu, pp. 1-15, found at www.sepmag.eu/free-basic-guide-magnetic-bead-cell-separation, (2017).

Su, W-S. et al., "Controllable permeability of blood-brain barrier and reduced brain injury through low-intensity pulsed ultrasound stimulation", Oncotarget, vol. 6, No. 39, pp. 42290-42299, (2015).

Haslbeck, K.M. et al., "The RAGE pathway in inflammatory myopathies and limb girdle muscular dystrophy", Acta Neuropathologica, vol. 110, issue 3, pp. 247-254, (2005).

Sternberg, Z. et al., "AGE-RAGE in multiple sclerosis brain", Immunological Investigations, vol. 40, issue 2, pp. 197-205, (2011). Abstract Only.

Miyata, T. et al., "Increased pentosidine, an advanced glycation end product, in plasma and synovial fluid from patients with rheumatoid arthritis and its relation with inflammatory markers", Biochemical and Biophysical Research Communications, vol. 244, pp. 45-49, (1998).

Mulrennan, S. et al., "The role of receptor for advanced glycation end products in airway inflammation in CF and CF related diabetes", Scientific Reports, vol. 5, No. 8931, pp. 1-9, (2015).

Weber, K. et al., "Distribution of advanced glycation end products in the cerebellar neurons of dogs", Brain Research, vol. 791, pp. 11-17, (1998).

Berg, T.J. et al., "The advanced glycation end product $N^\epsilon$-(carboxymethyl)lysine is increased in serum from children and adolescents with type 1 diabetes", Diabetes Care, vol. 21, No. 11, pp. 1997-2002, (1998).

Degenhardt, T.P. et al., "The serum concentration of the advanced glycation end-product $N^\epsilon$-(carboxymethyl)lysine is increased in uremia", Kidney International, vol. 52, pp. 1064-1067, (1997).

Hayase, F. et al., "Aging of proteins: Immunological detection of a glucose-derived pyrrole formed during maillard reaction in vivo", the Journal of Biological Chemistry, vol. 263, No. 7, pp. 3758-3764, (1989).

Ikeda, K. et al., "Immunochemical approaches to AGE-structures: characterization of anti-AGE antibodies", the Maillard Reaction in Foods and Medicine, pp. 310-315, (1998).

Kume, S. et al., "Immunohistochemical and ultrastructural detection of advanced glycation end products in atherosclerotic lesions of human aorta with a novel specific monoclonal antibody", American Journal of Pathology, vol. 147, No. 3, pp. 654-667, (1995).

Makita, A. et al., "Immunochemical detection of advanced glycosylation end products in vivo", the Journal of Biological Chemistry, vol. 267, No. 8, pp. 5133-5138, (1992).

Niwa, T. et al., "Immunohistochemical detection of advanced glycation end products in dialysis-related amyloidosis", Kidney International, vol. 48, pp. 771-778, (1995).

Papanastasiou, P. et al., "Immunological quantification of advanced glycosylation end-products in the serum of patients on hemodialysis of CAPD", Kidney International, vol. 46, pp. 216-222, (1994).

Schleicher, E.D. et al., "Increased accumulation of the glycoxidation product N(epsilon)-(carboxymethyl)lysine in human tissues in diabetes and aging", the Journal of Clinical Investigation, vol. 99, No. 3, pp. 457-468, (1997).

Takeuchi, M. et al., "Immunological detection of a novel advanced glycation end-product", Molecular Medicine, vol. 7, No. 11, pp. 783-791, (2001).

Kobayashi, S. et al., "$N^\epsilon$-(Carboxymethyl)lysine-induced choroidal angiogenic potential facilitates retinal neovascularization in advanced-diabetic rat in vitro", the Open Pharmacology Journal vol. 2, pp. 79-85, (2008).

Tamemoto, H. et al., "AGE inhibitor-recent development", Diabetes Frontier, vol. 16, No. 5, pp. 541-546, (2005).

Nagai, R. et al., "Prevention of diabetic complication by AGE inhibitors", Progress of Medicine, vol. 207, No. 9, pp. 663-667, (2003).

(56) References Cited

OTHER PUBLICATIONS

Vistoli, G. et al., "Advanced glycoxidation and lipoxidation end products (AGEs and ALEs): an overview of their mechanisms of formation", Free Radical Research, vol. 47, supple. 1, pp. 3-27, (2013).
Bachmeier, B.E. et al., "Maillard products as biomarkers in cancer", Annals of the New York Academy of Sciences, vol. 1126, No. 1, pp. 283-287, (2008). Abstract Only.
Chen, Z. et al., "Senescent cells re-engineered to express soluble programmed death receptor-1 for inhibiting programmed death receptor-1/programmed death ligand-1 as a vaccination approach against breast cancer", Cancer Science, vol. 109, pp. 1753-1763, (2018).
Leontieva, O.V. et al., "Yeast-like chronological senescence in mammalian cells: phenomenon, mechanism and pharmacological suppression", Aging, vol. 3, No. 11, pp. 1-14, (2011).
Moser, A.C. et al., "Immunoaffinity chromatography: an introduction to applications and recent developments", Bioanalysis, vol. 2, No. 4, pp. 769-790, (2010).
Prosser, C.G. et al., "$N^\epsilon$-carboxymethyllysine in nutritional milk formulas for infants", Food Chemistry, vol. 274, pp. 886-890, (2019).
Takeuchi, M. et al., "Detection of noncarboxymethyllysine and carboxymethyllysine advanced glycation end products (AGE) in serum of diabetic patients", Molecular Medicine, vol. 5, pp. 393-405, (1999).
Teodorowicz, M. et al., Immunomodulation by processed animal feed: the role of maillard reaction products and advanced glycation end-products (AGEs), Frontiers in Immunology, vol. 9, article 2088, pp. 1-15, (2018).
Kwak, T. et al., "Targeting of RAGE-ligand signaling impairs breast cancer cell invasion and metastasis", Oncogene, vol. 11, pp. 1559-1572, (2017). Abstract Only.
Inui, H. et al., "A scFv antibody-based immunoaffinity chromatography column for clean-up of bisphenol a-contaminated water samples", Journal of Agricultural and Food Chemistry, vol. 57, No. 2, pp. 353-358, (2009). Abstract Only.
Casset, F. et al., "A peptide mimetic of an anti-CD4 monoclonal antibody by rational design", Biochemical and Biophysical Research Communications, vol. 307, pp. 198-205, (2003).
Chikazawa, M. et al., "Multispecificity of immunoglobulin M antibodies raised against advanced glycation end products", the Journal of Biological Chemistry, vol. 288, No. 19, pp. 13204-13214, (2013).
De Pascalis, R. et al., "Grafting of "abbreviated" complementarity-determining regions containing specificity-determining residues essential for ligand contact to engineer a less immunogenic humanized monoclonal antibody", the Journal of Immunology, vol. 169, pp. 3076-3084, (2002).
Hirose, J. et al., "Immunohistochemical distribution of advanced glycation end products (AFEs) in human osteoarthritic cartilage", Acta Histochemica, vol. 113, No. 6, pp. 613-618, (2011).
Kumar, S. et al., "Molecular cloning and expression of the fabs of human autoantibodies in *Escherichia coli*", the Journal of Biological Chemistry, vol. 275, No. 45, pp. 35129-35136, (2000).
Lamminmaki, U. et al., "Crystal structure of a recombinant anti-estradiol fab fragment in complex with 17β-estradiol", the Journal of Biological Chemistry, vol. 276, No. 39, pp. 36687-36694, (2001).
Padlan, E.A. et al., "Structure of an antibody-antigen complex: Crystal structure of the hyhel-10 fab-lysozyme complex", Proceedings of the National Academy of Science, fol. 86, pp. 5938-5942, (1989).
Schwab, W. et al., "Immunohistochemical demonstration of $N^\epsilon$-(carboxymethyl)lysine protein adducts in normal and osteoarthritic cartilage", Histochemistry and Cell Biology, vol. 117, issue 6, pp. 541-546, (2002).
Smith-Gill, S.J. et al., "Contributions of immunoglobulin heavy and light chains to antibody specificity for lysozyme and two haptens" the Journal of Immunology, vol. 139, No. 12, pp. 4135-4144, (1987).
Song, M-K, et al., "Light chain of natural antibody plays a dominant role in protein antigen binding", Biochemical and Biophysical Research Communications, vol. 268, pp. 390-394, (2000).
Ward, E.S. et al., "Binding activities of a repertoire of single immunoglobulin variable domains secreted from *Escherichia coli*", Nature, vol. 341, pp. 544-546, (1989).
Jun. 23, 2020, U.S. Appl. No. 14/920,737.
Jun. 24, 2020 17737078.0 SIW01-011-Ep Ep.
Jun. 26, 2020 201737009367 SIW01-008-In in.
Jun. 15, 2020 2018-566505 SIW01-015-Jp Jp.
Jul. 13, 2020 19210193.9 SIW01-013-Div-Ep Ep.
Dec. 12, 2019 17708098.3 SIW01-013-Ep Ep.
Jul. 23, 2020, U.S. Appl. No. 15/720,912.
Jul. 24, 2020, U.S. Appl. No. 15/863,784.
Jul. 20, 2020, U.S. Appl. No. 15/863,811.
Jul. 24, 2020 15772116.8 SIW01-008-Ep Ep.
Aug. 4, 2020, U.S. Appl. No. 14/920,737.
Aug. 6, 2020, U.S. Appl. No. 15/953,244.
Aug. 12, 2020, U.S. Appl. No. 16/077,713.
Aug. 04, 2020 2020-106264 SIW01-013-Div-Jp Jp.
Aug. 26, 2020, U.S. Appl. No. 15/768,425.
Sep. 9, 2020, U.S. Appl. No. 16/440,747.
Sep. 16, 2020, U.S. Appl. No. 15/863,784.
Sep. 16, 2020, U.S. Appl. No. 15/953,244.
Jeon O.H. et al., "Senescent cells and osteoarthritis: a painful connection", The Journal of Clinical Investigation, vol. 128, No. 4, pp. 1229-1237, (2018).
Guan, Z. et al., "Contemporary views on inflammatory pain mechanisms: TRPing over innate and microglial pathways", F1000Research, vol. 5, pp. 1-11, (2016).
Musi, N. et al., "Tau protein aggregation is associated with cellular senescence in the brain", Aging Cell, vol. 17, pp. 1-13, (2018).
International Search Report and Written Opinion dated Nov. 25, 2019 for PCT application No. PCT/US2019/047762.
Dillon, P., "Focused ultrasound and pembrolizumab in metastatic breast cancer (breast-48)", ClinicalTrials.gov, pp. 1-7. (2017).
Masui, T. et al., "Low-intensity ultrasound enhances the anticancer activity of cetuximab in human head and neck cancer cells", Experimental and Therapeutic Medicine, vol. 5, pp. 11-16, (2013).
Khaibullina, A. et al., "Pulsed high-intensity focused ultrasound enhances uptake of radiolabeled monoclonal antibody to human epidermoid tumor in nude mice", The Journal of Nuclear Medicine, vol. 49, pp. 295-302, (2008).
Liao, A-H. et al., "Enhanced therapeutic epidermal growth factor receptor (EGFR) antibody delivery via pulsed ultrasound with targeting microbubbles for glioma treatment", Journal of Medical and Biological Engineering, vol. 35, pp. 156-164, (2015).
Liu, H-L. et al., "Focused ultrasound enhances central nervous system delivery of bevacizumab for malignant glioma treatment", Radiology, vol. 281, No. 1, pp. 99-108, (2016).
Kobus, T. et al., "Growth inhibition in a brain metastasis model by antibody delivery using focused ultrasound-mediated blood-brain barrier disruption", Journal of Controlled Release, vol. 238, pp. 281-288, (2016).
Linetsky, M. et al., "UVA light-excited kynurenines oxidize ascorbate and modify lens proteins through the formation of advanced glycation end products, Implications for Human Lens Aging and Cataract Formation", Journal of Biological Chemistry, vol. 289, No. 24, pp. 17111-17123, (2014).
Chaudhary, M.K. et al., "Redox imbalance in a model of rat mimicking Hutchinson-Gilford progeria syndrome", Biochemical and Biophysical Research Communications, vol. 491, No. 2, pp. 361-367, (2017). Abstract Only.
Hause F. et al., "Accumulation of glycated proteins suggesting premature ageing in lamin B receptor deficient mice", Biogerontology, vol. 19, No. 1, pp. 95-100, (2017). Abstract Only.
International Search Report and Written Opinion dated Nov. 27, 2019 for PCT application No. PCT/US2019/043071.
Zhang, J-M. et al., "Cytokines, Inflammation and Pain", International Anesthesiology Clinics, vol. 45, No. 2, pp. 27-37, (2007).
Bhatt A.N. et al., "Transient elevation of glycolysis confers radio-resistance by facilitating DNA repair in cells", BMC Cancer, vol. 15, Article 335, pp. 1-12, (2015).

(56) References Cited

OTHER PUBLICATIONS

Callier, V., "Cancer cells can't proliferate and invade at the same time", Scientific American, pp. 1-5, (2016), found at www.scientificamerican.com/article/cancer-cells-can-t-proliferate-and-invade-at-the-same-time.
Drews, G. et al., "Oxidative stress and beta-cell dysfunction", European Journal of Physiology, vol. 460, pp. 703-718, (2010).
Huang, C-C. et al., "Glycolytic inhibitor 2-deoxyglucose simultaneously targets cancer and endothelial cells to suppress neuroblastoma growth in mice", Disease Models and Mechanisms, vol. 8, pp. 1247-1254, (2015).
Kehm, R. et al., "age-related oxidative changes in pancreatic islets are predominantly located in the vascular system", Redox Biology, vol. 15, pp. 387-393, (2018).
Kohrman, A.Q. et al., "Divide or conquer: Cell cycle regulation of invasive behavior", Trends in Cell Biology, vol. 27, issue 1, pp. 12-25, (2017).
Menini, S. et al., "The advanced glycation end-product Nɛ-carboxymethyllysine promotes progression of pancreatic cancer: implications for diabetes-associated risk and its prevention", Journal of Pathology, vol. 245, pp. 197-208, (2018).
Wang, J. et al., "Oxidative stress in pancreatic beta cell regeneration", Oxidative Medicine and Cellular Longevity, vol. 2017, Article id 1930261, pp. 1-9, (2017).
Nerlich, A.G. et al., "Nɛ-(carboxymethyl)lysine in atherosclerotic vascular lesions as a marker for local oxidative stress", Atherosclerosis, vol. 144, issue 1, pp. 41-47, (1999). Abstract Only.
Soreide, K. et al., "Epidemiological-molecular evidence of metabolic reprogramming on proliferation, autophagy and cell signaling in pancreas cancer", Cancer Letters, vol. 356, issue 2, part A, pp. 281-288, (2015) Abstract Only.
Krautwald, M. et al., "Advanced glycation end products as biomarkers and gerontotoxins—a basis to explore methylglyoxal-lowering agents for Alzheimer's disease?", Experimental Gerontolosy, vol. 45, issue 10, pp. 744-751, (2010). Abstract Only.
Leclerc, E., "Development of monoclonal antibodies to inhibit Rage activation in pancreatic tumors", North Dakota State University, Center for diagnostic and therapeutic strategies in pancreatic cancer, 1 page, (2019), found at www.ndsu.edu/centers/pancreaticcancer/former investigators/leclerc_project/.
Yamagishi, S-I., et al., "DNA-aptamers raised against AGEs as a blocker of various aging- related disorders", Glycoconjugate Journal, vol. 33, pp. 683-690, (2016).
Kawaguchi, M. et al., "Glyoxal inactivates glutamate transporter-1 in cultured rat astrocytes", Neuropathology, vol. 25, pp. 27-36, (2005).
Scicchitano, B.M. et al., "Counteracting muscle wasting in aging and neuromuscular diseases: the critical role of Igf-1", Aging, vol. 1, no. 5, pp. 451-457, (2009).
Southern, L. et al., "Immunohistochemical study of N-epsilon-carboxymethyl lysine (CML) in human brain: relation to vascular dementia", BMC Neuology, vol. 7, article No. 35, pp. 1-8, (2007).
Hanssen, N. M. J. et al., "Higher levels of advanced glycation endproducts in human carotid atherosclerotic plaques are associated with a rupture-prone phenotype", European Heart Journal, vol. 35, pp. 1137-1146, (2014).
Ramunas, J. et al., "Transient delivery of modified mRNA encoding Tert rapidly extends telomeres in human cells", The FASEB Journal, vol. 29, No. 5, pp. 1930-1939, (2015).
Gutierrez-Reyes, G. et al., "Cellular senescence in livers from children with end stage liver disease", Plos One, vol. 5, issue 4, pp. 1-5, (2010).
Extended European Search Report dated May 29, 2020 for European application No. 19210193.9-1111, 8 pages.
Taguchi, A. et al., "Blockade of Rage-amphoterin signalling suppresses tumour growth and metastases", Nature, vol. 405, pp. 354-360, (2000).
Janeway, C. A. Jr. et al., "Appendix I. Immunologists' toolbox", Immunobiology: The immune system in health and disease, 5th edition, Garland Science, (2001), found at www.ncbi.nim.nih.gov/books/NBK10755/, (2001).
Haus, J. M. et al., "Collagen, cross-linking, and advanced glycation end products in aging human skeletal muscle", Journal of Applied Physiology, vol. 103, pp. 2068-2076, (2007).
Yi, H-S. et al., "T-cell senescence contributes to abnormal glucose homeostasis in humans and mice", Cell Death and Disease, vol. 10, No. 249, pp. 1-15, (2019).
Al-Motawa, M. et al., "Vulnerabilities of the SARS-CoV-2 virus to proteotoxicity—opportunity for repurposed chemotherapy of Covid-19 infection", Cell-Reports, 43 pages, found at www.ssrn.com/abstract=3582068, (2020).
d'Adda di Fagagna, F., "Living on a break: cellular senescence as a DNA-damage response", Nature Reviews Cancer, vol. 8, pp. 512-522, (2008).
"New biomarker for the prevention of arteriosclerosis", Atherosclerosis Prevention, vol. 14, No. 1, pp. 22-27, (2015).
Baxevanis, C.N. "Antibody-based cancer therapy", Expert Opinion Drug Discovery, vol. 3, No. 4, pp. 441-452, (2008).
U.S. Appl. No. 14/932,200, filed Nov. 4, 2015.
U.S. Appl. No. 15/720,912, filed Sep. 29, 2017.
U.S. Appl. No. 16/265,875, filed Feb. 1, 2019.
U.S. Appl. No. 14/920,737, filed Oct. 22, 2015.
U.S. Appl. No. 16/440,747, filed Jun. 13, 2019.
U.S. Appl. No. 15/511,731, filed Sep. 15, 2015.
U.S. Appl. No. 15/977,587, filed May 11, 2018.
U.S. Appl. No. 16/092,743, filed Apr. 14, 2017.
U.S. Appl. No. 16/077,713, filed Feb. 16, 2017.
U.S. Appl. No. 15/768,425, filed May 27, 2016.
U.S. Appl. No. 16/311,149, filed Dec. 18, 2018.
U.S. Appl. No. 15/863,784, filed Jan. 5, 2018.
U.S. Appl. No. 15/863,811, filed Jan. 5, 2018.
U.S. Appl. No. 15/863,828, filed Jan. 5, 2018.
U.S. Appl. No. 16/228,293, filed Dec. 20, 2018.
U.S. Appl. No. 15/953,244, filed Apr. 13, 2018.
U.S. Appl. No. 16/383,348, filed Apr. 12, 2019.
Malatesta, M. "skeletal muscle features in myotonic dystrophy and sarcopenia: do similar nuclear mechanisms lead to skeletal wasting?", European Journal of Histochemistry, vol. 56, pp. 228-230, (2012).
Wingerchuk, D. M. et al., "Multiple sclerosis: Current and emerging disease-modifying therapies and treatment strategies", Mayo Clinic Proceedings, vol. 89, No. 2, pp. 225-240, (2014).
Matias-Guiu J.A. et al., "Amyloid proteins and their role in multiple sclerosis. Considerations in the use of amyloid-PET imaging", Frontiers in Neurology, vol. 7, article 53, pp. 1-7, (2016).
Sternberg, Z. et al., "Diagnostic potential of plasma carbxymethyllysine and carboxyethyllysine in multiple sclerosis", Journal of Neuroinflammation, vol. 7, No. 72, pp. 1-8, (2010).
6 pages, Sep. 29, 2020, U.S. Appl. No. 15/768,425.
6 pages, Sep. 29, 2020, U.S. Appl. No. 15/863,811.
67 pages, Sep. 17, 2020, U.S. Appl. No. 15/863,828.
63 pages, Oct. 21, 2020, U.S. Appl. No. 16/311,149.
11 pages, Oct. 22, 2020, U.S. Appl. No. 15/863,811.
4 pages, Oct. 27, 2020, U.S. Appl. No. 15/863,828.
74 pages, Nov. 6, 2020, U.S. Appl. No. 16/092,743.
3 pages, Nov. 12, 2020, U.S. Appl. No. 15/953,244.
47 pages, Nov. 9, 2020, U.S. Appl. No. 14/920,737.
5 pages, Nov. 19, 2020, U.S. Appl. No. 16/228,293.
4 pages, Nov. 24, 2020, JP Application No. 2020-106264.
5 pages, Nov. 24, 2020, U.S. Appl. No. 15/768,425.
U.S. Appl. No. 17/089,999, filed Nov. 5, 2020.
15 pages, Sep. 30, 2019, U.S. Appl. No. 15/863,784.
12 pages, Oct. 7, 2019, U.S. Appl. No. 15/863,828.
6 pages, Oct. 11, 2019, U.S. Appl. No. 15/953,244.
10 pages, Oct. 11, 2019, U.S. Appl. No. 15/768,425.
7 pages, Oct. 15, 2019, U.S. Appl. No. 16/092,743.
12 pages, Oct. 21, 2019, U.S. Appl. No. 15/511,731.
38 pages, Oct. 30, 2019, U.S. Appl. No. 15/720,912.
4 pages, Nov. 1, 2019, U.S. Appl. No. 15/863,811.
Nov. 14, 2019 PCT/US2018/030931 SIW01-025-Wo Wo.
28 pages, Nov. 20, 2019, U.S. Appl. No. 14/932,200.

(56) References Cited

OTHER PUBLICATIONS 3 pages, Nov. 21, 2019, U.S. Appl. No. 15/863,784.
Jan. 23, 2019 18184822.7 SIW01-002-Div-Ep Ep.
Feb. 04, 2019 15772116.8 SIW01-008-Ep Ep.
Feb. 14, 2019 11776932.3 SIW01-002-Ep Ep.
8 pages, Dec. 11, 2019, U.S. Appl. No. 15/977,587.
Dec. 11, 2019 18726656.4 SIW01-025-Ep Ep.
3 pages, Dec. 20, 2019, U.S. Appl. No. 15/863,828.
3 pages, Jan. 13, 2020, U.S. Appl. No. 14/920,737.
6 pages, Jan. 27, 2020, U.S. Appl. No. 15/511,731.
7 pages, Feb. 7, 2020, U.S. Appl. No. 15/863,784.
56 pages, Feb. 11, 2020, U.S. Appl. No. 15/863,811.
8 pages, Mar. 17, 2020, U.S. Appl. No. 15/768,425.
6 pages, Mar. 20, 2020, U.S. Appl. No. 15/953,244.
11 pages, Mar. 31, 2020, U.S. Appl. No. 14/920,737.
79 pages, Mar. 18, 2020, U.S. Appl. No. 16/092,743.
7 pages, Apr. 16, 2020, U.S. Appl. No. 15/863,828.
4 pages, May 18, 2020, U.S. Appl. No. 15/720,912.
17 pages, May 19, 2020, U.S. Appl. No. 14/932,200.
76 pages, May 28, 2020, U.S. Appl. No. 15/977,587.
10 pages, Jun. 2, 2020, U.S. Appl. No. 16/077,713.
65 pages, Jun. 18, 2020, U.S. Appl. No. 15/863,784.
Gunawan, M. et al., "A novel human systemic lupus erythematosus model in humanised mice", Nature Scientific Reports, vol. 7, pp. 1-11, (2017).
9 pages, Dec. 3, 2020, U.S. Appl. No. 15/863,784.
4 pages, Dec. 9, 2020, U.S. Appl. No. 15/768,425.
7 pages, Dec. 17, 2020, U.S. Appl. No. 15/863,784.
9 pages, Dec. 17, 2020, U.S. Appl. No. 15/863,784.

\* cited by examiner

VACCINES FOR USE IN TREATING JUVENILE DISORDERS ASSOCIATED WITH INFLAMMATION

BACKGROUND

Senescent cells are cells that are partially-functional or non-functional and are in a state of proliferative arrest. Senescence is a distinct state of a cell, and is associated with biomarkers, such as activation of the biomarker $p16^{Ink4a}$, and expression of β-galactosidase. Senescence begins with damage or stress (such as overstimulation by growth factors) of cells.

Advanced glycation end-products (AGEs; also referred to as AGE-modified proteins, or glycation end-products) arise from a non-enzymatic reaction of sugars with protein sidechains (Ando, K. et al., Membrane Proteins of Human Erythrocytes Are Modified by Advanced Glycation End Products during Aging in the Circulation, *Biochem Biophys Res Commun.*, Vol. 258, 123, 125 (1999)). This process begins with a reversible reaction between the reducing sugar and the amino group to form a Schiff base, which proceeds to form a covalently-bonded Amadori rearrangement product. Once formed, the Amadori product undergoes further rearrangement to produce AGEs. Hyperglycemia, caused by diabetes mellitus (DM), and oxidative stress promote this post-translational modification of membrane proteins (Lindsey J B, et al., "Receptor For Advanced Glycation End-Products (RAGE) and soluble RAGE (sRAGE): Cardiovascular Implications," *Diabetes Vascular Disease Research*, Vol. 6(1), 7-14, (2009)). AGEs may also be formed from other processes. For example, the advanced glycation end product, $N^\varepsilon$-(carboxymethyl)lysine, is a product of both lipid peroxidation and glycoxidation reactions. AGEs have been associated with several pathological conditions including diabetic complications, inflammation, retinopathy, nephropathy, atherosclerosis, stroke, endothelial cell dysfunction, and neurodegenerative disorders (Bierhaus A, "AGEs and their interaction with AGE-receptors in vascular disease and diabetes mellitus. I. The AGE concept," Cardiovasc Res, Vol. 37(3), 586-600 (1998)).

AGE-modified proteins are also a marker of senescent cells. This association between glycation end-product and senescence is well known in the art. See, for example, Gruber, L. (WO 2009/143411, 26 Nov. 2009), Ando, K. et al. (Membrane Proteins of Human Erythrocytes Are Modified by Advanced Glycation End Products during Aging in the Circulation, *Biochem Biophys Res Commun.*, Vol. 258, 123, 125 (1999)), Ahmed, E. K. et al. ("Protein Modification and Replicative Senescence of WI-38 Human Embryonic Fibroblasts" *Aging Cells*, vol. 9, 252, 260 (2010)), Vlassara, H. et al. (Advanced Glycosylation Endproducts on Erythrocyte Cell Surface Induce Receptor-Mediated Phagocytosis by Macrophages, *J. Exp. Med.*, Vol. 166, 539, 545 (1987)) and Vlassara et al. ("High-affinity-receptor-mediated Uptake and Degradation of Glucose-modified Proteins: A Potential Mechanism for the Removal of Senescent Macromolecules" *Proc. Natl. Acad. Sci. USAI*, Vol. 82, 5588, 5591 (1985)). Furthermore, Ahmed, E. K. et al. indicates that glycation end-products are "one of the major causes of spontaneous damage to cellular and extracellular proteins" (Ahmed, E. K. et al., see above, page 353). Accordingly, the accumulation of glycation end-products is associated with senescence and lack of function.

The damage or stress that causes cellular senescence also negatively impacts mitochondrial DNA in the cells to cause them to produce free radicals which react with sugars in the cell to form methyl glyoxal (MG). MG in turn reacts with proteins or lipids to generate advanced glycation end products. In the case of the protein component lysine, MG reacts to form carboxymethyllysine, which is an AGE.

Damage or stress to mitochondrial DNA also sets off a DNA damage response which induces the cell to produce cell cycle blocking proteins. These blocking proteins prevent the cell from dividing. Continued damage or stress causes mTOR production, which in turn activates protein synthesis and inactivates protein breakdown. Further stimulation of the cells leads to programmed cell death (apoptosis).

p16 is a protein involved in regulation of the cell cycle, by inhibiting the S phase (synthesis phase). It can be activated during ageing or in response to various stresses, such as DNA damage, oxidative stress or exposure to drugs. p16 is typically considered a tumor suppressor protein, causing a cell to become senescent in response to DNA damage and irreversibly preventing the cell from entering a hyperproliferative state. However, there has been some ambiguity in this regard, as some tumors show overexpression of p16, while other show downregulated expression. Evidence suggests that overexpression of p16 is some tumors results from a defective retinoblastoma protein ("Rb"). p16 acts on Rb to inhibit the S phase, and Rb downregulates p16, creating negative feedback. Defective Rb fails to both inhibit the S phase and downregulate p16, thus resulting in overexpression of p16 in hyperproliferating cells (Romagosa, C. et al., $p16^{Ink4a}$ overexpression in cancer: a tumor suppressor gene associated with senescence and high-grade tumors, *Oncogene*, Vol. 30, 2087-2097 (2011)).

Senescent cells are associated with secretion of many factors involved in intercellular signaling, including pro-inflammatory factors; secretion of these factors has been termed the senescence-associated secretory phenotype, or SASP (Freund, A. "Inflammatory networks during cellular senescence: causes and consequences" Trends Mol Med. 2010 May; 16(5):238-46). Autoimmune diseases, such as osteoarthritis, Crohn's disease, and rheumatoid arthritis are associated with chronic inflammation (Ferraccioli, G. et al. "Interleukin-1β and Interleukin-6 in Arthritis Animal Models: Roles in the Early Phase of Transition from Acute to Chronic Inflammation and Relevance for Human Rheumatoid Arthritis" Mol Med. 2010 November-December; 16(11-12): 552-557). Chronic inflammation may be characterized by the presence of pro-inflammatory factors at levels higher than baseline near the site of pathology, but lower than those found in acute inflammation. Examples of these factors include TNF, IL-1α, IL-1β, IL-5, IL-6, IL-8, IL-12, IL-23, CD2, CD3, CD20, CD22, CD52, CD80, CD86, C5 complement protein, BAFF, APRIL, IgE, α4β1 integrin and α4β7 integrin. Because senescent cells produce pro-inflammatory factors, removal of these cells alone produces a profound reduction in inflammation as well as the amount and concentration of pro-inflammatory factors.

Senescent cells secrete reactive oxygen species ("ROS") as part of the SASP. ROS is believed to play an important role in maintaining senescence of cells. The secretion of ROS creates a bystander effect, where senescent cells induce senescence in neighboring cells: ROS create the very cellular damage known to activate p16 expression, leading to senescence (Nelson, G., A senescent cell bystander effect: senescence-induced senescence, *Aging Cell*, Vo. 11, 345-349 (2012)). The p16/Rb pathway leads to the induction of ROS, which in turn activates the protein kinase C delta creating a positive feedback loop that further enhance ROS, helping maintain the irreversible cell cycle arrest; it has even been suggested that exposing cancer cells to ROS might be effective to treat cancer by inducing cell phase arrest in hyperproliferating cells (Rayess, H. et al., Cellular senescence and tumor suppressor gene p16, *Int J Cancer*, Vol. 130, 1715-1725 (2012)).

A number of juvenile disorders have been associated with inflammation, and many are also associated with autoimmunity. These disorders are characterized by progression and worsen over time. Examples of juvenile disorders that have been associated with inflammation and autoimmunity include juvenile rheumatoid arthritis, idiopathic myopathies, multiple sclerosis, muscular dystrophy, neuromyelitis optica, X-linked adrenoleukodystrophy, cystic fibrosis and epilepsy.

Rheumatoid arthritis is one of the most well-known inflammatory autoimmune diseases and is referred to as juvenile rheumatoid arthritis (also known as JRA, juvenile idiopathic arthritis, JIA, juvenile chronic arthritis or JCA) when present in juveniles. Idiopathic myopathies, such as idiopathic inflammatory myopathy, idiopathic inflammatory myositis, polymyositis, dermatomyositis, sporadic inclusion body myositis and juvenile myositis, are diseases characterized by progressive muscle weakness and damage. It is believed that these diseases are autoimmune diseases, or that autoimmune responses contribute to their development and progression (Rayavarapu, S. et al., "Idiopathic inflammatory myopathies: pathogenic mechanisms of muscle weakness", Skeletal Muscle, Vol. 3, 13 pages (June 2013)).

Juvenile disorders of the central nervous system have also been associated with inflammation. Multiple sclerosis (MS) is the most common autoimmune disorder affecting the central nervous system. Multiple sclerosis is both an inflammatory and a neurodegenerative disease, and many current therapies and novel therapies in clinical development focus on reducing inflammation by administration of antibodies (Luessi, F., et al. "Neurodegeneration in multiple sclerosis: novel treatment strategies" *Expert Rev. Neurother.*, Vol 9, pp. 1061-1077 (2012)). Muscular dystrophy (MD) refers to a group of more than 30 diseases characterized by progressive weakness and degeneration of the skeletal muscles that control movement. Senescence of muscle satellite cells may be triggered by cellular stress and has been identified as a pathogenic feature of muscular dystrophy (Kudryashova, E. et al. Satellite cell senescence underlies myopathy in a mouse model of limb-girdle muscular dystrophy 2H; *J Clin Invest.* 2012; 122(5):1764-1776 (2012)). Neuromyelitis optica (also known as NMO, Devic's disease and Devic's syndrome) is an inflammatory demyelinating disease of the central nervous system in which autoantibodies (NMO-IgG) target aquaporin-4, the major water channel of astrocytes in the central nervous system (Ratelade, J. et al., "Neuromyelitis optica IgG and natural killer cells produce NMO lesions in mice without myelin loss", Acta Neuropathologica, Vol. 123, No. 6, pp. 861-872 (June 2012)). NMO-IgG binds to human fetal astrocytes and can result in natural killer cell degranulation, astrocyte killing by antibody-dependent cell-mediated cytotoxicity (ADCC) and complement-dependent granulocyte attraction through the blood-brain barrier (Vincent, T. et al., "Functional consequences of neuromyelitis optica-IgG astrocyte interactions on blood-brain barrier permeability and granulocyte recruitment", The Journal of Immunology, Vol. 181, pp. 5730-5737 (2008)).

Peroxisomal disorders are medical conditions caused by defects in peroxisome functions that affect the nervous system and may also be correlated with inflammation. X-linked adrenoleukodystrophy (X-ALD) is the most common peroxisomal disorder and results from mutation or deletion of the ABCD1 gene (Baarine, M. et al., "ABCD1 deletion-induced mitochondrial dysfunction is corrected by SAHA: implication for adrenoleukodystrophy", Journal of Neurochemistry, Vol. 133, No. 3, pp. 380-396 (2015)). In juveniles, adrenoleukodystrophy may be present as the fatal disease cerebral ALD (cALD), which is characterized by progressive cerebral demyelination with a strong inflammatory response in the white matter (Id.).

Cystic fibrosis (CF) is a lethal disease that results from mutations of the cystic fibrosis transmembrane conductance regulator (CFTR) gene and is characterized by chronic inflammation of the airways and lung tissue (Durieu, S. et al., "Subepithelial fibrosis and degradation of the bronchial extracellular matrix in cystic fibrosis", American Journal of Respiratory and Critical Care Medicine, Vol. 158, pp. 580-588 (1998)). Cystic fibrosis has been associated with cellular senescence (Shapiro, B. L. et al., "Premature senescence in cultured skin fibroblasts from subjects with cystic fibrosis", Science, Vol. 203, Issue 4386, pp. 1251-1253 (1979)). Neutrophil elastase is known to trigger cell cycle arrest, which may lead to senescence and inflammation, and research suggests that neutrophil elastase triggers expression of senescence markers in cystic fibrosis airway epithelial cells (Fischer, B. M. et al., "Increased expression of senescence markers in cystic fibrosis airways", American Journal of Physiology Lung Cellular and Molecular Physiology, Vol. 304, pp. L394-L400 (2013)).

Epilepsy may be a symptom of a separate juvenile disorder, or may be a distinct diagnosis. Symptomatic epilepsy, like cystic fibrosis, has been associated with cellular senescence. For example, focal cortical dysplasia type IIB is a malformation of the front lobe of the brain and is characterized by the presence of balloon cells. The balloon cells have an abnormal cell cycle and exhibit premature and hypertrophic senescence (Thom, M. et al., "An investigation of the expression of G1-phase cell cycle proteins in focal cortical dysplasia type IIB", Journal of Neuropathology & Experimental Neurology, Vol. 66, No. 11, pp. 1045-1055 (November 2007)).

Recent research demonstrates the therapeutic benefits of removing senescent cells. In vivo animal studies at the Mayo Clinic in Rochester, Minn., found that elimination of senescent cells in transgenic mice carrying a biomarker for elimination delayed age-related disorders associated with cellular senescence. Eliminating senescent cells in fat and muscle tissues substantially delayed the onset of sarcopenia and cataracts and reduced senescence indicators in skeletal muscle and the eye (Baker, D. J. et al., "Clearance of $p16^{Ink4a}$-positive senescent cells delays ageing-associated disorders", Nature, Vol. 479, pp. 232-236, (2011)). Mice that were treated to induce senescent cell elimination were found to have larger diameters of muscle fibers as compared to untreated mice. Treadmill exercise tests indicated that treatment also preserved muscle function. Continuous treatment of transgenic mice for removal of senescent cells had no negative side effects and selectively delayed age-related phenotypes that depend on cells. This data demonstrates that removal of senescent cells produces beneficial therapeutic effects and shows that these benefits may be achieved without adverse effects.

Additional In vivo animal studies in mice found that senescent cells using senolytic agents treats aging-related disorders and atherosclerosis. Short-term treatment with senolytic drugs in chronologically aged or progeroid mice alleviated several aging-related phenotypes (Zhu, Y. et al., "The Achilles' heel of senescent cells: from transcriptome to senolytic drugs", Aging Cell, vol. 14, pp. 644-658 (2015)).

Long-term treatment with senolytic drugs improved vasomotor function in mice with established atherosclerosis and reduced intimal plaque calcification (Roos, C. M. et al., "Chronic senolytic treatment alleviates established vasomotor dysfunction in aged or atherosclerotic mice", Aging Cell (2016)). This data further demonstrates the benefits of removing senescent cells.

Vaccines have been widely used since their introduction by Edward Jenner in the 1770s to confer immunity against a wide range of diseases and afflictions. Vaccine preparations contain a selected immunogenic agent capable of stimulating immunity to an antigen. Typically, antigens are used as the immunogenic agent in vaccines, such as, for example, viruses, either killed or attenuated, and purified viral components. Antigens used in the production of cancer vaccines include, for example, tumor-associated carbohydrate antigens (TACAs), dendritic cells, whole cells and viral vectors. Different techniques are employed to produce the desired amount and type of antigen being sought. For example, pathogenic viruses are grown either in eggs or cells. Recombinant DNA technology is often utilized to generate attenuated viruses for vaccines.

Vaccines may therefore be used to stimulate the production of antibodies in the body and provide immunity against antigens. When an antigen is introduced to a subject that has been vaccinated and developed immunity to that antigen, the immune system may destroy or remove cells that express the antigen.

SUMMARY

In a first aspect, the invention is a method of treating or preventing the onset of a juvenile disorder associated with inflammation comprising immunizing a subject in need thereof against AGE-modified proteins or peptides of a cell.

In a second aspect, the invention is a method of treating a subject with a juvenile disorder associated with inflammation comprising administering a first vaccine comprising a first AGE antigen and, optionally, administering a second vaccine comprising a second AGE antigen. The second AGE antigen is different from the first AGE antigen.

In a third aspect, the invention is use of an AGE antigen for the manufacture of a medicament for treating or preventing the onset of a juvenile disorder associated with inflammation.

In a fourth aspect, the invention is a composition comprising an AGE antigen for use in treating or preventing the onset of a juvenile disorder associated with inflammation.

In a fifth aspect, the invention is a composition comprising an AGE antigen for use in treating or preventing the onset of muscular dystrophy.

In a sixth aspect, the invention is a composition comprising an AGE antigen for use in treating or preventing the onset of cystic fibrosis.

In a seventh aspect, the invention is a composition comprising an AGE antigen for use in treating or preventing the onset of juvenile rheumatoid arthritis.

In an eighth aspect, the invention is a composition comprising an AGE antigen for use in treating or preventing the onset of neuromyelitis optica.

In a ninth aspect, the invention is a composition comprising an AGE antigen for use in treating or preventing the onset of idiopathic myopathies.

In a tenth aspect, the invention is a composition comprising an AGE antigen for use in treating or preventing the onset of multiple sclerosis.

In an eleventh aspect, the invention is a composition comprising an AGE antigen for use in treating or preventing the onset of epilepsy.

In a twelfth aspect, the invention is a composition comprising an AGE antigen for use in treating or preventing the onset of cerebral adrenoleukodystrophy.

In a thirteenth aspect, the invention is a method of treating or preventing the onset of a juvenile disorder associated with inflammation comprising immunizing a woman against AGE-modified proteins or peptides of a cell. The woman is pregnant with a subject in need of treatment or prevention of the juvenile disorder associated with inflammation, or the woman is breastfeeding the subject in need of treatment or prevention of the juvenile disorder associated with inflammation.

Definitions

The term "peptide" means a molecule composed of 2-50 amino acids.

The term "protein" means a molecule composed of more than 50 amino acids.

The terms "advanced glycation end-product," "AGE," "AGE-modified protein or peptide," and "glycation end-product" refer to modified proteins or peptides that are formed as the result of the reaction of sugars with protein side chains that further rearrange and form irreversible cross-links. This process begins with a reversible reaction between a reducing sugar and an amino group to form a Schiff base, which proceeds to form a covalently-bonded Amadori rearrangement product. Once formed, the Amadori product undergoes further rearrangement to produce AGEs. AGE-modified proteins and antibodies to AGE-modified proteins are described in U.S. Pat. No. 5,702,704 to Bucala ("Bucala") and U.S. Pat. No. 6,380,165 to Al-Abed et al. ("Al-Abed"). Glycated proteins or peptides that have not undergone the necessary rearrangement to form AGEs, such as N-deoxyfructosyllysine found on glycated albumin, are not AGEs. AGEs may be identified by the presence of AGE modifications (also referred to as AGE epitopes or AGE moieties) such as 2-(2-furoyl)-4(5)-(2-furanyl)-1H-imidazole ("FFI"); 5-hydroxymethyl-1-alkylpyrrole-2-carbaldehyde ("Pyrraline"); 1-alkyl-2-formyl-3,4-diglycosyl pyrrole ("AFGP"), a non-fluorescent model AGE; carboxymethyllysine; carboxyethyllysine; and pentosidine. ALI, another AGE, is described in Al-Abed.

The term "AGE antigen" means a substance that elicits an immune response against an AGE-modified protein or peptide of a cell. The immune response against an AGE-modified protein or peptide of a cell does not include the production of antibodies to the non-AGE-modified protein or peptide.

The term "AGE antibody" means an antibody specific for an AGE-modified protein or peptide of a cell.

The term "senescent cell" means a cell which is in a state of proliferative arrest and expresses one or more biomarkers of senescence, such as activation of p16$^{Ink4a}$ or expression of β-galactosidase. Also included are cells which express one or more biomarkers of senescence, do not proliferate in vivo, but may proliferate in vitro under certain conditions, such as some satellite cells found in the muscles of ALS patients.

The term "juvenile" means an individual that has not completed puberty.

The term "juvenile disorder" means a disease or disorder that has an onset in individuals that have not completed puberty.

The term "juvenile disorder associated with inflammation" means a juvenile disease or disorder that causes inflammation or is intensified by inflammation. Juvenile disorders associated with inflammation are characterized by progression, meaning they worsen over time. Preferably, the juvenile disorder associated with inflammation is a genetic disorder. Genetic disorders are those which are caused by a chromosome abnormality. The chromosome abnormality may be hereditary or may be the result of a chromosome mutation.

The term "breastfeeding" includes feeding a juvenile directly from a lactating woman's breast as well as feeding a juvenile with expressed breastmilk from a bottle or similar administration device.

DETAILED DESCRIPTION

The observation of inflammation, as well as autoimmunity, in juvenile disorders implicates cellular senescence. Senescent cells are known to promote inflammation and secrete inflammatory factors as part of the senescence-associated secretory phenotype (SASP). The positive feedback loop that exists between senescent cells and reactive oxygen species is indicative of the progressive nature of juvenile disorders associated with inflammation. These characteristics suggest that cellular senescence is a causative factor in the onset and progression of juvenile disorders associated with inflammation.

The therapeutic benefits of removing senescent cells has been demonstrated in atherosclerosis and in age-related diseases, such as sarcopenia. The identification of a link between cellular senescence and juvenile disorders associated with senescence allows for similar treatment possibilities. For example, if the immunogenic agent of a vaccine is an AGE-modified protein or peptide, the immune system of an immunized subject may kill or induce apoptosis in cells expressing the AGE-modified protein or peptide. The removal of senescent cells will inhibit the progression of juvenile disorders associated with inflammation, and will prevent the onset of juvenile disorders in subjects with sub-clinical inflammation or autoimmunity.

The present invention uses enhanced clearance of cells expressing AGE-modified proteins or peptides (AGE-modified cells) to treat, ameliorate or prevent the onset of juvenile disorders associated with inflammation. Vaccination against AGE-modified proteins or peptides of a cell produces the desired result of controlling the presence of AGE-modified cells in a subject in need thereof. The continuous and virtually ubiquitous surveillance exercised by the immune system in the body in response to a vaccination allows maintaining low levels of AGE-modified cells in the body. Vaccination against AGE-modified proteins or peptides of a cell removes or kills senescent cells. The process of senescent cell removal or destruction allows vaccination against AGE-modified proteins or peptides of a cell to be used therapeutically in the treatment of juvenile disorders associated with inflammation. The vaccines may be administered to children, or may be administered to pregnant or breastfeeding women who will pass the antibodies to their fetuses or breastfeeding infants.

Juvenile disorders associated with inflammation include juvenile rheumatoid arthritis (also known as JRA, juvenile idiopathic arthritis, JIA, juvenile chronic arthritis or JCA), idiopathic myopathies, multiple sclerosis (MS), muscular dystrophy (MD), neuromyelitis optica (also known as NMO, Devic's disease and Devic's syndrome), X-linked adrenoleukodystrophy, cystic fibrosis (CF) and epilepsy. In some cases, such as cystic fibrosis and epilepsy, senescent cells have been directly implicated in the etiology of the juvenile disorder. Preferably, the juvenile disorder associated with inflammation is a genetic disorder.

Vaccines against AGE-modified proteins or peptides contain an AGE antigen, an adjuvant, optional preservatives and optional excipients. Examples of AGE antigens include AGE-modified proteins or peptides such as AGE-antithrombin III, AGE-calmodulin, AGE-insulin, AGE-ceruloplasmin, AGE-collagen, AGE-cathepsin B, AGE-albumin such as AGE-bovine serum albumin (AGE-BSA), AGE-human serum albumin and ovalbumin, AGE-crystallin, AGE-plasminogen activator, AGE-endothelial plasma membrane protein, AGE-aldehyde reductase, AGE-transferrin, AGE-fibrin, AGE-copper/zinc SOD, AGE-apo B, AGE-fibronectin, AGE-pancreatic ribose, AGE-apo A-I and II, AGE-hemoglobin, AGE-Na$^+$/K$^+$-ATPase, AGE-plasminogen, AGE-myelin, AGE-lysozyme, AGE-immunoglobulin, AGE-red cell Glu transport protein, AGE-β-N-acetyl hexominase, AGE-apo E, AGE-red cell membrane protein, AGE-aldose reductase, AGE-ferritin, AGE-red cell spectrin, AGE-alcohol dehydrogenase, AGE-haptoglobin, AGE-tubulin, AGE-thyroid hormone, AGE-fibrinogen, AGE-$β_2$-microglobulin, AGE-sorbitol dehydrogenase, AGE-$α_1$-antitrypsin, AGE-carbonate dehydratase, AGE-RNAse, AGE-low density lipoprotein, AGE-hexokinase, AGE-apo C-I, AGE-RNAse, AGE-hemoglobin such as AGE-human hemoglobin, AGE-low density lipoprotein (AGE-LDL) and AGE-collagen IV. AGE-modified cells, such as AGE-modified erythrocytes, whole, lysed, or partially digested, may also be used as AGE antigens. Suitable AGE antigens also include proteins or peptides that exhibit AGE modifications (also referred to as AGE epitopes or AGE moieties) such as carboxymethyllysine (CML), carboxyethyllysine (CEL), pentosidine, pyrraline, FFI, AFGP and ALI. The AGE antigen may be an AGE-protein conjugate, such as AGE conjugated to keyhole limpet hemocyanin (AGE-KLH). Further details of some of these AGE-modified proteins or peptides and their preparation are described in Bucala.

Particularly preferred AGE antigens include proteins or peptides that exhibit a carboxymethyllysine or carboxyethyllysine AGE modification. Carboxymethyllysine (also known as N(epsilon)-(carboxymethyl)lysine, N(6)-carboxymethyllysine, or 2-Amino-6-(carboxymethylamino) hexanoic acid) and carboxyethyllysine (also known as N-epsilon-(carboxyethyl)lysine) are found on proteins or peptides and lipids as a result of oxidative stress and chemical glycation. CML- and CEL-modified proteins or peptides are recognized by the receptor RAGE which is expressed on a variety of cells. CML and CEL have been well-studied and CML- and CEL-related products are commercially available. For example, Cell Biolabs, Inc. sells CML-BSA antigens, CML polyclonal antibodies, CML immunoblot kits, and CML competitive ELISA kits (www.cellbiolabs.com/cml-assays) as well as CEL-BSA antigens and CEL competitive ELISA kits (www.cellbiolabs.com/cel-n-epsilon-carboxyethyl-lysine-assays-and-reagents).

AGE antigens may be conjugated to carrier proteins to enhance antibody production in a subject. Antigens that are not sufficiently immunogenic alone may require a suitable carrier protein to stimulate a response from the immune system. Examples of suitable carrier proteins include keyhole limpet hemocyanin (KLH), serum albumin, bovine thyroglobulin, cholera toxin, labile enterotoxin, silica particles and soybean trypsin inhibitor. Preferably, the carrier protein is KLH (AGE-KLH). KLH has been extensively studied and has been identified as an effective carrier protein in experimental cancer vaccines. Preferred AGE antigen-carrier protein conjugates include AGE-KLH; particularly preferred AGE antigen-carrier protein conjugates include CML-KLH and CEL-KLH.

The administration of an AGE antigen allows the immune system to develop immunity to the antigen. Immunity is a long-term immune response, either cellular or humoral. A cellular immune response is activated when an antigen is presented, preferably with a co-stimulator to a T-cell which causes it to differentiate and produce cytokines. The cells involved in the generation of the cellular immune response are two classes of T-helper (Th) cells, Th1 and Th2. Th1 cells stimulate B cells to produce predominantly antibodies of the IgG2A isotype, which activates the complement cascade and binds the Fc receptors of macrophages, while Th2 cells stimulate B cells to produce IgG1 isotype antibodies in mice, IgG4 isotype antibodies in humans, and IgE isotype antibodies. The human body also contains "professional" antigen-presenting cells such as dendritic cells, macrophages, and B cells.

A humoral immune response is triggered when a B cell selectively binds to an antigen and begins to proliferate, leading to the production of a clonal population of cells that produce antibodies that specifically recognize that antigen and which may differentiate into antibody-secreting cells, referred to as plasma-cells or memory-B cells. Antibodies are molecules produced by B-cells that bind a specific antigen. The antigen-antibody complex triggers several responses, either cell-mediated, for example by natural killers (NK) or macrophages, or serum-mediated, for example by activating the complement system, a complex of several serum proteins that act sequentially in a cascade that result in the lysis of the target cell.

Immunological adjuvants (also referred to simply as "adjuvants") are the component(s) of a vaccine which augment the immune response to the immunogenic agent. Adjuvants function by attracting macrophages to the immunogenic agent and then presenting the agent to the regional lymph nodes to initiate an effective antigenic response. Adjuvants may also act as carriers themselves for the immunogenic agent. Adjuvants may induce an inflammatory response, which may play an important role in initiating the immune response.

Adjuvants include mineral compounds such as aluminum salts, oil emulsions, bacterial products, liposomes, immunostimulating complexes and squalene. Aluminum compounds are the most widely used adjuvants in human and veterinary vaccines. These aluminum compounds include aluminum salts such as aluminum phosphate ($AlPO_4$) and aluminum hydroxide ($Al(OH)_3$) compounds, typically in the form of gels, and are generically referred to in the field of vaccine immunological adjuvants as "alum." Aluminum hydroxide is a poorly crystalline aluminum oxyhydroxide having the structure of the mineral boehmite. Aluminum phosphate is an amorphous aluminum hydroxyphosphate. Negatively charged species (for example, negatively charged antigens) can absorb onto aluminum hydroxide gels at neutral pH, whereas positively charged species (for example, positively charged antigens) can absorb onto aluminum phosphate gels at neutral pH. It is believed that these aluminum compounds provide a depot of antigen at the site of administration, thereby providing a gradual and continuous release of antigen to stimulate antibody production. Aluminum compounds tend to more effectively stimulate a cellular response mediated by Th2, rather than Th1 cells.

Emulsion adjuvants include water-in-oil emulsions (for example, Freund's adjuvants, such as killed mycobacteria in oil emulsion) and oil-in-water emulsions (for example, MF-59). Emulsion adjuvants include an immunogenic component, for example squalene (MF-59) or mannide oleate (Incomplete Freund's Adjuvants), which can induce an elevated humoral response, increased T cell proliferation, cytotoxic lymphocytes and cell-mediated immunity.

Liposomal or vesicular adjuvants (including paucilamellar lipid vesicles) have lipophilic bilayer domains and an aqueous milieu which can be used to encapsulate and transport a variety of materials, for example an antigen. Paucilamellar vesicles (for example, those described in U.S. Pat. No. 6,387,373) can be prepared by mixing, under high pressure or shear conditions, a lipid phase comprising a non-phospholipid material (for example, an amphiphile surfactant; see U.S. Pat. Nos. 4,217,344; 4,917,951; and 4,911,928), optionally a sterol, and any water-immiscible oily material to be encapsulated in the vesicles (for example, an oil such as squalene oil and an oil-soluble or oil-suspended antigen); and an aqueous phase such as water, saline, buffer or any other aqueous solution used to hydrate the lipids. Liposomal or vesicular adjuvants are believed to promote contact of the antigen with immune cells, for example by fusion of the vesicle to the immune cell membrane, and preferentially stimulate the Th1 sub-population of T-helper cells.

Other types of adjuvants include *Mycobacterium bovis* bacillus Calmette-Guerin (BCG), quill-saponin and unmethylated CpG dinucleotides (CpG motifs). Additional adjuvants are described in U.S. Patent Application Publication Pub. No. US 2010/0226932 (Sep. 9, 2010) and Jiang, Z-H. et al. "Synthetic vaccines: the role of adjuvants in immune targeting", *Current Medicinal Chemistry*, Vol. 10(15), pp. 1423-39 (2003). Preferable adjuvants include Freund's complete adjuvant and Freund's incomplete adjuvant.

The vaccine may optionally include one or more preservatives, such as antioxidants, antibacterial and antimicrobial agents, as well as combinations thereof. Examples include benzethonium chloride, ethylenediamine-tetraacetic acid sodium (EDTA), thimerosal, phenol, 2-phenoxyethanol, formaldehyde and formalin; antibacterial agents such as amphotericin B, chlortetracycline, gentamicin, neomycin, polymyxin B and streptomycin; antimicrobial surfactants such as polyoxyethylene-9, 10-nonyl phenol (Triton N-101, octoxynol-9), sodium deoxycholate and polyoxyethylated octyl phenol (Triton X-100). The production and packaging of the vaccine may eliminate the need for a preservative. For example, a vaccine that has been sterilized and stored in a sealed container may not require a preservative.

Other components of vaccines include pharmaceutically acceptable excipients, such as stabilizers, thickening agents, toxin detoxifiers, diluents, pH adjusters, tonicity adjustors, surfactants, antifoaming agents, protein stabilizers, dyes and solvents. Examples of such excipients include hydrochloric acid, phosphate buffers, sodium acetate, sodium bicarbonate, sodium borate, sodium citrate, sodium hydroxide, potassium chloride, potassium chloride, sodium chloride, polydimethylsilozone, brilliant green, phenol red (phenolsulfonphthalein), glycine, glycerin, sorbitol, histidine, monosodium glutamate, potassium glutamate, sucrose, urea, lactose, gelatin, sorbitol, polysorbate 20, polysorbate 80 and glutaraldehyde. A variety of these components of vaccines, as well as adjuvants, are described in www.cdc.gov/vaccines/pubs/pinkbook/downloads/appendices/Blexcipient-table-2.pdf and Vogel, F. R. et al., "A compendium of vaccine adjuvants and excipients", *Pharmaceutical Biotechnology*, Vol. 6, pp. 141-228 (1995).

The vaccine may contain from 1 µg to 100 mg of at least one AGE antigen, including 10, 20, 30, 40, 50, 60, 70, 80, 90, 100, 200, 400, 800 or 1000 µg, or 2, 3, 4, 5, 6, 7, 8, 9, 10, 20, 30, 40, 50, 60, 70, 80 or 90 mg. The amount used for a single injection corresponds to a unit dosage.

The vaccine may be provided in unit dosage form or in multidosage form, such as 2-100 or 2-10 doses. The unit dosages may be provided in a vial with a septum, or in a syringe with or without a needle. The vaccine may be administered intravenously, subdermally or intraperitoneally. Preferably, the vaccine is sterile.

The vaccine may be administered one or more times, such as 1 to 10 times, including 2, 3, 4, 5, 6, 7, 8 or 9 times, and may be administered over a period of time ranging from 1 week to 1 year, 2-10 weeks or 2-10 months. Furthermore, booster vaccinations may be desirable, over the course of 1 year to 20 years, including 2, 5, 10 and 15 years.

A subject that receives a vaccine for AGE-modified proteins or peptides of a cell may be tested to determine if he or she has developed an immunity to the AGE-modified proteins or peptides. Suitable tests may include blood tests for detecting the presence of an antibody, such as immunoassays or antibody titers. Alternatively, an immunity to AGE-modified proteins or peptides may be determined by monitoring the progression of symptoms of a juvenile disorder over time. For example, a baseline skeletal muscle mass in a subject with muscular dystrophy may be measured followed by administration of the vaccine for AGE-modified proteins or peptides of a cell. Immunity to AGE-modified proteins or peptides may be determined by periodically measuring skeletal muscle mass in the subject and comparing the subsequent measurements to the baseline measurement. A subject may be considered to have developed an immunity to AGE-modified proteins or peptides if he or she does not demonstrate loss of skeletal muscle mass between subsequent measurements or over time. Similarly, a reduction in inflammatory factors would be indicative of the development of an immunity to AGE-modified proteins or peptides improvement in a subject with juvenile rheumatoid arthritis. An immunity to AGE-modified proteins or peptides may also be determined by directly monitoring the concentration and/or number of senescent cells over time. In addition to testing for the development of an immunity to AGE-modified proteins or peptides, a subject may also be tested to determine if the vaccination has been effective to treat a juvenile disorder associated with inflammation. The effectiveness of the vaccination may be determined by vaccinating a subject followed by periodic testing, such as by measuring the skeletal muscle mass of a subject with muscular dystrophy over time or measuring the concentration and/or number of inflammatory factors or senescent cells in a subject with cystic fibrosis. Vaccination and subsequent testing may be repeated until the desired therapeutic result is achieved.

The vaccination process may be designed to provide immunity against multiple AGE moieties. A single AGE antigen may induce the production of AGE antibodies which are capable of binding to multiple AGE moieties. Alternatively, the vaccine may contain multiple AGE antigens. In addition, a subject may receive multiple vaccines, where each vaccine contains a different AGE antigen.

Any mammal that could develop juvenile disorders associated with inflammation may be treated by the methods herein described. Humans are a preferred mammal for treatment. Other mammals that may be treated include mice, rats, goats, sheep, cows, horses and companion animals, such as dogs or cats. The vaccine may be administered directly to a juvenile mammal. Alternatively, or in addition, the vaccine may be administered to a pregnant or breastfeeding woman. Vaccinating a pregnant woman will allow her immune system to generate antibodies and pass these antibodies to her fetus. The pregnant woman may be the biological mother of the child, or may be the non-biological mother of the child, such as a surrogate. Similarly, vaccinating a breastfeeding woman will allow her immune system to generate antibodies that may be passed to a breastfeeding infant. The breastfeeding woman may be the biological mother of the child, or may be a lactating woman that is not the biological mother, such as a wet nurse or an adoptive mother.

A subject may be identified as in need of treatment based on genetic testing. A juvenile or a fetus may be diagnosed with a juvenile disorder associated with inflammation, or may undergo genetic testing to identify a genetic predisposition for developing a juvenile disorder associated with inflammation. Any party that is genetically related to the subject may be genetically tested to determine the presence of, or genetic predisposition to, a juvenile disorder associated with inflammation. Genetically related parties that could be subjected to genetic testing include the mother and father who conceived the child, a party that participated in donor-assisted reproduction, such as a sperm donor or egg donor, and family members who are genetically related to these individuals. Any genetic test that is capable of diagnosing or identifying a predisposition to developing a juvenile disorder associated with inflammation may be used. Examples of genetic tests that may be carried out include newborn screening, diagnostic testing, carrier testing, pre-implantation genetic diagnosis, prenatal diagnosis, predictive and pre-symptomatic testing and pharmacogenomics.

Alternatively, a subject may be identified as in need of treatment based on a familial history of a juvenile disorder associated with inflammation. For example, a child who has two siblings with muscular dystrophy may be vaccinated based on a suspected hereditary risk of also developing muscular dystrophy. Similarly, a child from a family with a high prevalence of autoimmune diseases may be vaccinated based on a likelihood of developing a juvenile disorder associated with inflammation that is considered to be an autoimmune disease, such as neuromyelitis optica. In addition, a subject that belongs to a racial or ethnic group that is known to have a high prevalence of a particular juvenile disorder associated with inflammation may be vaccinated against that disorder.

EXAMPLES

Example 1 (Prophetic): An AGE-RNAse Containing Vaccine in a Human Subject

AGE-RNAse is prepared by incubating RNAse in a phosphate buffer solution containing 0.1-3 M glucose, glucose-6-phosphate, fructose or ribose for 10-100 days. The AGE-RNAse solution is dialyzed and the protein content is measured. Aluminum hydroxide or aluminum phosphate, as an adjuvant, is added to 100 µg of the AGE-RNAse. Formaldehyde or formalin is added as a preservative to the preparation. Ascorbic acid is added as an antioxidant. The vaccine also includes phosphate buffer to adjust the pH and glycine as a protein stabilizer. The composition is injected into a human juvenile subject subcutaneously.

Example 2 (Prophetic): Injection Regimen for an AGE-RNAse Containing Vaccine in a Human Subject The same vaccine as described in Example 1 is injected into a human juvenile subject. The titer of antibodies to AGE-RNAse is determined by ELISA after two weeks. Additional injections are performed after three weeks and six weeks, respectively. Further titer determination is performed two weeks after each injection.

Example 3 (Prophetic): An AGE-Hemoglobin Containing Vaccine in a Human Subject

AGE-hemoglobin is prepared by incubating human hemoglobin in a phosphate buffer solution containing 0.1-3 M glucose, glucose-6-phosphate, fructose or ribose for 10-100 days. The AGE-hemoglobin solution is dialyzed and the protein content is measured. All vaccine components are the same as in Example 1, except AGE-hemoglobin is substituted for AGE-RNAse. Administration is carried out as in Example 1, or as in Example 2.

Example 4 (Prophetic): An AGE-Human Serum Albumin Containing Vaccine in a Human Subject AGE-human serum albumin is prepared by incubating human serum albumin in a phosphate buffer solution containing 0.1-3 M glucose, glucose-6-phosphate, fructose or ribose for 10-100 days. The AGE-human serum albumin solution is dialyzed and the protein content is measured. All vaccine components are the same as in Example 1, except AGE-human serum albumin is substituted for AGE-RNAse. Administration is carried out as in Example 1, or as in Example 2.

Example 5: In Vivo Study of the Administration of Anti-AGE Antibody

To examine the effects of an anti-AGE antibody, the antibody was administered to the aged CD1(ICR) mouse (Charles River Laboratories), twice daily by intravenous injection, once a week, for three weeks (Days 1, 8 and 15), followed by a 10 week treatment-free period. The test antibody was a commercially available mouse anti-AGE antibody raised against carboxymethyl lysine conjugated with keyhole limpet hemocyanin. A control reference of physiological saline was used in the control animals.

Mice referred to as "young" were 8 weeks old, while mice referred to as "old" were 88 weeks (±2 days) old. No adverse events were noted from the administration of the antibody. The different groups of animals used in the study are shown in Table 1.

TABLE 1

The different groups of animals used in the study

| Group No. | Test Material | Mice | Dose Level (μg/gm/BID/week) | Number of Animals Main Study Females | Number of Animals Treatment-Free Females |
|---|---|---|---|---|---|
| 1 | Saline | young | 0 | 20 | — |
| 2 | Saline | old | 0 | 20 | 20 |
| 3 | Antibody | old | 2.5 | 20 | 20 |
| 4 | None | old | 0 | 20 | pre |
| 5 | Antibody | old | 5.0 | 20 | 20 |

— = Not Applicable,
Pre = Subset of animals euthanized prior to treatment start for collection of adipose tissue.

$p16^{INK4a}$ mRNA, a marker for senescent cells, was quantified in adipose tissue of the groups by Real Time-qPCR. The results are shown in Table 2. In the table $\Delta\Delta Ct = \Delta Ct$ mean control Group (2)$-\Delta Ct$ mean experimental Group (1 or 3 or 5); Fold Expression=$2^{-\Delta\Delta Ct}$.

TABLE 2

$P16^{INK4a}$ mRNA quantified in adipose tissue

| Calculation (unadjusted to Group 4: 5.59) | Group 2 vs Group 1 | | Group 2 vs Group 3 | | Group 2 vs Group 5 | |
|---|---|---|---|---|---|---|
| | Group 2 | Group 1 | Group 2 | Group 3 | Group 2 | Group 5 |
| Mean ΔCt | 5.79 | 7.14 | 5.79 | 6.09 | 5.79 | 7.39 |
| ΔΔCt | | −1.35 | | −0.30 | | −1.60 |
| Fold Expression | | 2.55 | | 1.23 | | 3.03 |

The table above indicates that untreated old mice (Control Group 2) express 2.55-fold more $p16^{Ink4a}$ mRNA than the untreated young mice (Control Group 1), as expected. This was observed when comparing Group 2 untreated old mice euthanized at end of recovery Day 85 to Group 1 untreated young mice euthanized at end of treatment Day 22. When results from Group 2 untreated old mice were compared to results from Group 3 treated old mice euthanized Day 85, it was observed that $p16^{Ink4a}$ mRNA was 1.23-fold higher in Group 2 than in Group 3. Therefore, the level of $p16^{Ink4a}$ mRNA expression was lower when the old mice were treated with 2.5 μg/gram/BID/week of antibody.

When results from Group 2 (Control) untreated old mice were compared to results from Group 5 (5 μg/gram) treated old mice euthanized Day 22, it was observed that $p16^{Ink4a}$ mRNA was 3.03-fold higher in Group 2 (controls) than in Group 5 (5 μg/gram). This comparison indicated that the Group 5 animals had lower levels of $p16^{Ink4a}$ mRNA expression when they were treated with 5.0 μg/gram/BID/week, providing $p16^{Ink4a}$ mRNA expression levels comparable to that of the young untreated mice (Group 1). Unlike Group 3 (2.5 μg/gram) mice that were euthanized at end of recovery Day 85, Group 5 mice were euthanized at end of treatment Day 22.

These results indicate the antibody administration resulted in the killing of senescent cells.

The mass of the gastrocnemius muscle was also measured, to determine the effect of antibody administration on a classic sign of aging, sarcopenia. The results are shown in Table 3. The results indicate that administration of the antibody increased muscle mass as compared to controls, but only at the higher dosage of 5.0 μg/gm/BID/week.

TABLE 3

Effect of antibody administration on mass of the gastrocnemius muscle

| Group | Summary Information | Absolute weight of Gastrocnemius Muscle | Weight relative to body mass of Gastrocnemius Muscle |
|---|---|---|---|
| 1 | Mean | 0.3291 | 1.1037 |
|   | SD   | 0.0412 | 0.1473 |
|   | N    | 20     | 20     |
| 2 | Mean | 0.3304 | 0.7671 |
|   | SD   | 0.0371 | 0.1246 |
|   | N    | 20     | 20     |
| 3 | Mean | 0.3410 | 0.7706 |
|   | SD   | 0.0439 | 0.0971 |
|   | N    | 19     | 19     |
| 5 | Mean | 0.4074 | 0.9480 |
|   | SD   | 0.0508 | 0.2049 |
|   | N    | 9      | 9      |

These results demonstrate that administration of antibodies that bind to AGEs of a cell resulted in a reduction of cells expressing $p16^{Ink4a}$, a biomarker of senescence. The data show that reducing senescent cells leads directly to an increase in muscle mass in aged mice. These results indicate that the loss of muscle mass, a classic sign of sarcopenia, can be treated by administration of antibodies that bind to AGEs of a cell.

Example 6: Carboxymethyllysine-Modified Protein Vaccine for a Human Subject (Prophetic)

A vaccine may be prepared by combining a carboxymethyllysine-modified protein as an AGE antigen, aluminum hydroxide as an adjuvant, formaldehyde as a preservative, ascorbic acid as an antioxidant, a phosphate buffer to adjust the pH of the vaccine and glycine as a protein stabilizer. The vaccine may be injected subcutaneously into a juvenile who has been identified as likely to develop cystic fibrosis based on genetic testing.

Example 7: Carboxyethyllysine-Modified Peptide Vaccine for a Human Subject (Prophetic)

A vaccine may be prepared by combining a carboxyethyllysine-modified peptide conjugated to KLH as an AGE antigen, aluminum hydroxide as an adjuvant, formaldehyde as a preservative, ascorbic acid as an antioxidant, a phosphate buffer to adjust the pH of the vaccine and glycine as a protein stabilizer. The vaccine may be injected subcutaneously into a pregnant mother who has a family history of idiopathic myopathies.

REFERENCES

1. International Application Pub. No. WO 2009/143411 to Gruber (26 Nov. 2009).
2. U.S. Pat. No. 5,702,704 to Bucala (issued Dec. 30, 1997).
3. U.S. Pat. No. 6,380,165 to Al-Abed et al. (issued Apr. 30, 2002).
4. U.S. Pat. No. 6,387,373 to Wright et al. (issued May 14, 2002).
5. U.S. Pat. No. 4,217,344 to Vanlerberghe et al. (issued Aug. 12, 1980).
6. U.S. Pat. No. 4,917,951 to Wallach (issued Apr. 17, 1990).
7. U.S. Pat. No. 4,911,928 to Wallach (issued Mar. 27, 1990).
8. U.S. Patent Application Publication Pub. No. US 2010/0226932 to Smith et al. (Sep. 9, 2010).
9. Baker, D. J. et al., "Clearance of $p16^{Ink4a}$-positive senescent cells delays ageing-associated disorders", Nature, Vol. 479, pp. 232-236, (2011).
10. Ando, K. et al., "Membrane Proteins of Human Erythrocytes Are Modified by Advanced Glycation End Products during Aging in the Circulation", Biochem. Biophys. Res. Commun., Vol. 258, 123, 125 (1999).
11. Lindsey, J. B. et al., "Receptor For Advanced Glycation End-Products (RAGE) and soluble RAGE (sRAGE): Cardiovascular Implications", Diabetes Vascular Disease Research, Vol. 6(1), 7-14, (2009).
12. Bierhaus, A., "AGEs and their interaction with AGE-receptors in vascular disease and diabetes mellitus. I. The AGE concept", Cardiovasc. Res., Vol. 37(3), 586-600 (1998).
13. Ahmed, E. K. et al., "Protein Modification and Replicative Senescence of WI-38 Human Embryonic Fibroblasts", Aging Cells, Vol. 9, 252, 260 (2010).
14. Vlassara, H. et al., "Advanced Glycosylation Endproducts on Erythrocyte Cell Surface Induce Receptor-Mediated Phagocytosis by Macrophages", J. Exp. Med., Vol. 166, 539, 545 (1987).
15. Vlassara, H. et al., "High-affinity-receptor-mediated Uptake and Degradation of Glucose-modified Proteins: A Potential Mechanism for the Removal of Senescent Macromolecules", Proc. Natl. Acad. Sci. USA, Vol. 82, 5588, 5591 (1985).
16. Roll, P. et al., "Anti-CD20 Therapy in Patients with Rheumatoid Arthritis", Arthritis & Rheumatism, Vol. 58, No. 6, 1566-1575 (2008).
17. Kajstura, J. et al., "Myocite Turnover in the Aging Human Heart", Circ. Res., Vol. 107(11), 1374-86, (2010).
18. de Groot, K. et al., "Vascular Endothelial Damage and Repair in Antineutrophil Cytoplasmic Antibody-Associated Vasculitis", Arthritis and Rheumatism, Vol. 56(11), 3847, 3847 (2007).
19. Manesso, E. et al., "Dynamics of p-Cell Turnover: Evidence for β-Cell Turnover and Regeneration from Sources of β-Cells other than β-cell Replication in the HIP Rat", Am. J. Physiol. Endocrinol. Metab., Vol. 297, E323, E324 (2009).
20. Kirstein, M. et al., "Receptor-specific Induction of Insulin-like Growth Factor I in Human Monocytes by Advanced Glycosylation End Product-modified Proteins", J. Clin. Invest., Vol. 90, 439, 439-440 (1992).
21. Murphy, J. F., "Trends in cancer immunotherapy", Clinical Medical Insights: Oncology, Vol. 14(4), 67-80 (2010).
22. Flint, S. J. et al., "Principles of Virology", ASM Press (2000).
23. Buskas, T. et al., "Immunotherapy for Cancer: Synthetic Carbohydrate-based Vaccines", Chem. Commun., Vol. 28(36), 5335-349 (2009).
24. Beier, K. C. et al., "Master Switches of T-cell Differentiation", Eur. Respir. J., Vol. 29, 804-12 (2007).
25. Schmidlin H. et al., "New Insights in the Regulation of Human B Cell Differentiation", Trends Immunol., Vol. 30(6), 277-85 (2009).
26. Vogel, F. R. et al., "A compendium of vaccine adjuvants and excipients", Pharmaceutical Biotechnology, Vol. 6, pp. 141-228 (1995).
27. Coler, R. N. et al., "Development and Characterization of Synthetic Glucopyranosyl Lipid Adjuvant System as a Vaccine Adjuvant", PLoS ONE, Vol. 6(1): e16333 (2011).
28. Cheadle, E. J. et al., "Bugs as Drugs for Cancer", Immunology, Vol. 107, 10-19 (2002).

29. Jiang, Z-H. et al. "Synthetic vaccines: the role of adjuvants in immune targeting", *Current Medicinal Chemistry*, Vol. 10(15), pp. 1423-39 (2003).
30. Virella, G. et al., "Autoimmune Response to Advanced Glycosylation End-Products of Human LDL", *Journal of Lipid Research*, Vol. 44, 487-493 (2003).
31. Ameli, S. et al., "Effect of Immunization With Homologous LDL and Oxidized LDL on Early Atherosclerosis in Hypercholesterolemic Rabbits", *Arteriosclerosis, Thrombosis, and Vascular Biology*, Vol. 16, 1074 (1996).
32. "Vaccine Excipient & Media Summary", available online at www.cdc.gov/vaccines/pubs/pinkbook/downloads/appendices/B/excipient-table-2.pdf (The Pink Book, Epidemiology and Prevention of Vaccine-Preventable Diseases, 12$^{th}$Ed. Second Printing, September 2013).
33. "Sarcopenia", available online at en.wikipedia.org/wiki/Sarcopenia (Nov. 14, 2014).
34. "What is sarcopenia?", available online at www.iofbonehealth.org/what-sarcopenia (2014).
35. Blahd, W., "Sarcopenia with aging", available online at www.webmd.com/healthy-aging/sarcopenia-with-aging (Aug. 3, 2014).
36. "Keyhole limpet hemocyanin", available online at en.wikipedia.org/wiki/Keyhole_limpet_hemocyanin (Apr. 18, 2014).
37. "CML-BSA Product Data Sheet", available online at www.cellbiolabs.com/sites/default/files/STA-314-cml-bsa.pdf (2010).
38. "CML (N-epsilon-(Carboxymethyl)Lysine) Assays and Reagents", available online at www.cellbiolabs.com/cml-assays (Accessed on Dec. 15, 2014).
39. Cruz-Jentoft, A. J. et al., "Sarcopenia: European consensus on definition and diagnosis", *Age and Ageing*, Vol. 39, pp. 412-423 (Apr. 13, 2010).
40. Rolland, Y. et al., "Sarcopenia: its assessment, etiology, pathogenesis, consequences and future perspectives", *J. Nutr. Health Aging*, Vol. 12(7), pp. 433-450 (2008).
41. Mera, K. et al., "An autoantibody against $N^\varepsilon$-(carboxyethyl)lysine (CEL): Possible involvement in the removal of CEL-modified proteins by macrophages", *Biochemical and Biophysical Research Communications*, Vol. 407, pp. 420-425 (Mar. 12, 2011).
42. Reddy, S. et al., "$N^\varepsilon$-(carboxymethyl)lysine is a dominant advanced glycation end product (AGE) antigen in tissue proteins", *Biochemistry*, Vol. 34, pp. 10872-10878 (Aug. 1, 1995).
43. Naylor, R. M. et al., "Senescent cells: a novel therapeutic target for aging and age-related diseases", *Clinical Pharmacology & Therapeutics*, Vol. 93(1), pp. 105-116 (Dec. 5, 2012).
44. Katcher, H. L., "Studies that shed new light on aging", *Biochemistry (Moscow)*, Vol. 78(9), pp. 1061-1070 (2013).
45. Fielding, R. A., et al., "Sarcopenia: an undiagnosed condition in older adults. Current consensus definition: prevalence, etiology, and consequences", *Journal of the American Medical Directors Association*, Vol. 12(4), pp. 249-256 (May 2011).
46. Fu, M-X., et al., "The advanced glycation end product, $N^\varepsilon$-(carboxymethyl)lysine, is a product of both lipid peroxidation and glycoxidation reactions", The Journal of Biological Chemistry, Vol. 271, No. 17, pp. 9982-9986 (Apr. 26, 1996).
47. Kudryashova, E. et al., "Satellite cell senescence underlies myopathy in a mouse model of limb-girdle muscular dystrophy 2H", The Journal of Clinical Investigation, Vol. 122, No. 5, pp. 1764-1776 (May 2012).
48. Ratelade, J. et al., "Neuromyelitis optica IgG and natural killer cells produce NMO lesions in mice without myelin loss", Acta Neuropathologica, Vol. 123, No. 6, pp. 861-872 (June 2012).
49. Vincent, T. et al., "Functional consequences of neuromyelitis optica-IgG astrocyte interactions on blood-brain barrier permeability and granulocyte recruitment", The Journal of Immunology, Vol. 181, pp. 5730-5737 (2008).
50. Xu, M. et al., "Transplanted senescent cells induce an osteoarthritis-like condition in mice", Journals of Gerontology: Biological Sciences, Vol. 00, No. 00, 1-6 (2016).
51. Rayavarapu, S. et al., "Idiopathic inflammatory myopathies: pathogenic mechanisms of muscle weakness", Skeletal Muscle, Vol. 3, 13 pages (June 2013).
52. Luessi, F., et al. "Neurodegeneration in multiple sclerosis: novel treatment strategies" *Expert Rev. Neurother.*, Vol 9, pp. 1061-1077 (2012).
53. Durieu, S. et al., "Subepithelial fibrosis and degradation of the bronchial extracellular matrix in cystic fibrosis", American Journal of Respiratory and Critical Care Medicine, Vol. 158, pp. 580-588 (1998).
54. Shapiro, B. L. et al., "Premature senescence in cultured skin fibroblasts from subjects with cystic fibrosis", Science, Vol. 203, Issue 4386, pp. 1251-1253 (1979).
55. Fischer, B. M. et al., "Increased expression of senescence markers in cystic fibrosis airways", American Journal of Physiology Lung Cellular and Molecular Physiology, Vol. 304, pp. L394-L400 (2013).
56. Romagosa, C. et al., $p16^{Ink4a}$ overexpression in cancer: a tumor suppressor gene associated with senescence and high-grade tumors, Oncogene, Vol. 30, 2087-2097 (2011).
57. Thom, M. et al., "An investigation of the expression of G1-phase cell cycle proteins in focal cortical dysplasia type IIB", Journal of Neuropathology & Experimental Neurology, Vol. 66, No. 11, pp. 1045-1055 (November 2007).
58. Baarine, M. et al., "ABCD1 deletion-induced mitochondrial dysfunction is corrected by SAHA: implication for adrenoleukodystrophy", Journal of Neurochemistry, Vol. 133, No. 3, pp. 380-396 (2015).
59. Zhu, Y. et al., "The Achilles' heel of senescent cells: from transcriptome to senolytic drugs", Aging Cell, vol. 14, pp. 644-658 (2015).
60. Roos, C. M. et al., "Chronic senolytic treatment alleviates established vasomotor dysfunction in aged or atherosclerotic mice", Aging Cell (2016).

What is claimed is:

1. A method of treating a juvenile disorder associated with inflammation, comprising immunizing a subject in need thereof against AGE-modified proteins or peptides of a cell,
   wherein the juvenile disorder associated with inflammation is selected from the group consisting of muscular dystrophy, juvenile rheumatoid arthritis, and multiple sclerosis,
   the juvenile disorder has an onset in individuals that have not completed puberty,
   the immunizing comprises administering a vaccine comprising an AGE antigen, and
   the AGE antigen comprises at least one protein or peptide that exhibits at least one AGE modification selected from the group consisting of carboxymethyllysine, carboxyethyllysine, pentosidine, pyrraline, FFI, and AFGP.

2. The method of claim 1, wherein the vaccine comprises
(a) the AGE antigen,
(b) an adjuvant,
(c) optionally, a preservative, and
(d) optionally, an excipient.

3. The method of claim 1, wherein the AGE antigen is an AGE-modified protein or peptide selected from the group consisting of AGE-RNAse, AGE-human hemoglobin, AGE-human serum albumin, AGE-low density lipoprotein, AGE-collagen IV, AGE-antithrombin III, AGE-calmodulin, AGE-insulin, AGE-ceruloplasmin, AGE-collagen, AGE-cathepsin B, AGE-albumin, AGE-BSA, AGE-human serum albumin, AGE-ovalbumin, AGE-crystallin, AGE-plasminogen activator, AGE-endothelial plasma membrane protein, AGE-aldehyde reductase, AGE-transferrin, AGE-fibrin, AGE-copper/zinc SOD, AGE-apo B, AGE-fibronectin, AGE-pancreatic ribose, AGE-apo A-I and II, AGE-hemoglobin, AGE-Na$^+$/K$^+$-ATPase, AGE-plasminogen, AGE-myelin, AGE-lysozyme, AGE-immunoglobulin, AGE-red cell Glu transport protein, AGE-β-N-acetyl hexokinase, AGE-apo E, AGE-red cell membrane protein, AGE-aldose reductase, AGE-ferritin, AGE-red cell spectrin, AGE-alcohol dehydrogenase, AGE-haptoglobin, AGE-tubulin, AGE-thyroid hormone, AGE-fibrinogen, AGE-$β_2$-microglobulin, AGE-sorbitol dehydrogenase, AGE-$α_1$-antitrypsin, AGE-carbonate dehydratase, AGE-hexokinase, AGE-apo C-I, AGE-KLH and mixtures thereof.

4. The method of claim 1, wherein the AGE antigen comprises a carboxymethyllysine-modified protein or peptide.

5. The method of claim 1, wherein the AGE antigen comprises a carboxyethyllysine-modified protein or peptide.

6. The method of claim 1, wherein
the vaccine is sterile, and
the vaccine is in unit dosage form.

7. The method of claim 1, further comprising testing the patient to determine if the juvenile disorder associated with inflammation has been ameliorated, and
repeating the immunizing, if necessary.

8. The method of claim 1, wherein the AGE antigen comprises carboxymethyllysine conjugated with keyhole limpet hemocyanin (CML-KLH).

9. The method of claim 1, wherein the juvenile disorder associated with inflammation comprises muscular dystrophy.

10. The method of claim 1, wherein the juvenile disorder associated with inflammation comprises juvenile rheumatoid arthritis.

11. The method of claim 1, wherein the juvenile disorder associated with inflammation comprises multiple sclerosis.

12. The method of claim 1, wherein the subject is selected from the group consisting of humans, goats, sheep, cows, horses, dogs, and cats.

13. A method of treating a subject with a juvenile disorder associated with inflammation, comprising:
administering a first vaccine comprising a first AGE antigen; and
administering a second vaccine comprising a second AGE antigen;
wherein the second AGE antigen is different from the first AGE antigen,
the juvenile disorder associated with inflammation is selected from the group consisting of muscular dystrophy, juvenile rheumatoid arthritis, and multiple sclerosis,
the juvenile disorder has an onset in individuals that have not completed puberty, and
the first AGE antigen and the second AGE antigen each independently comprise at least one protein or peptide that exhibits at least one AGE modification selected from the group consisting of carboxymethyllysine, carboxyethyllysine, pentosidine, pyrraline, FFI, and AFGP.

14. The method of claim 13, wherein the first AGE antigen comprises carboxymethyllysine conjugated with keyhole limpet hemocyanin (CML-KLH).

15. The method of claim 13, wherein the juvenile disorder associated with inflammation comprises muscular dystrophy.

16. The method of claim 13, wherein the juvenile disorder associated with inflammation comprises juvenile rheumatoid arthritis.

17. The method of claim 13, wherein the juvenile disorder associated with inflammation comprises multiple sclerosis.

18. The method of claim 13, wherein the subject is selected from the group consisting of humans, goats, sheep, cows, horses, dogs, and cats.

19. The method of claim 13, wherein the first vaccine comprises
(a) the first AGE antigen,
(b) a first adjuvant,
(c) optionally, a first preservative, and
(d) optionally, a first excipient; and
wherein the second vaccine comprises
(i) the second AGE antigen,
(ii) a second adjuvant,
(iii) optionally, a second preservative, and
(iv) optionally, a second excipient.

20. The method of claim 13, wherein the first AGE antigen and the second AGE antigen each independently comprise an AGE-modified protein or peptide selected from the group consisting of AGE-RNAse, AGE-human hemoglobin, AGE-human serum albumin, AGE-low density lipoprotein, AGE-collagen IV, AGE-antithrombin III, AGE-calmodulin, AGE-insulin, AGE-ceruloplasmin, AGE-collagen, AGE-cathepsin B, AGE-albumin, AGE-BSA, AGE-human serum albumin, AGE-ovalbumin, AGE-crystallin, AGE-plasminogen activator, AGE-endothelial plasma membrane protein, AGE-aldehyde reductase, AGE-transferrin, AGE-fibrin, AGE-copper/zinc SOD, AGE-apo B, AGE-fibronectin, AGE-pancreatic ribose, AGE-apo A-I and II, AGE-hemoglobin, AGE-Na$^+$/K$^+$-ATPase, AGE-plasminogen, AGE-myelin, AGE-lysozyme, AGE-immunoglobulin, AGE-red cell Glu transport protein, AGE-β-N-acetyl hexokinase, AGE-apo E, AGE-red cell membrane protein, AGE-aldose reductase, AGE-ferritin, AGE-red cell spectrin, AGE-alcohol dehydrogenase, AGE-haptoglobin, AGE-tubulin, AGE-thyroid hormone, AGE-fibrinogen, AGE-$β_2$-microglobulin, AGE-sorbitol dehydrogenase, AGE-$α_1$-antitrypsin, AGE-carbonate dehydratase, AGE-hexokinase, AGE-apo C-I, AGE-KLH and mixtures thereof.

21. The method of claim 13, wherein
the first vaccine and the second vaccine each are sterile, and
the first vaccine and the second vaccine each are in unit dosage form.

22. The method of claim 13, further comprising testing the patient to determine if the juvenile disorder associated with inflammation has been ameliorated, and
repeating the immunizing, if necessary.

* * * * *